United States Patent
Hinner et al.

(10) Patent No.: US 11,919,931 B2
(45) Date of Patent: Mar. 5, 2024

(54) ANTI-CANCER FUSION POLYPEPTIDE CAPABLE OF BINDING BOTH CD137 AND GLYPICAN-3 (GPC3)

(71) Applicant: Pieris Pharmaceuticals GmbH, Hallbergmoos (DE)

(72) Inventors: Marlon Hinner, Munich (DE); Rachida Siham Bel Aiba, Munich (DE); Christine Rothe, Dachau (DE); Shane Olwill, Freising (DE); Corinna Schlosser, Freising (DE)

(73) Assignee: Pieris Pharmaceuticals GMBH, Hallbergmoos (DE)

( * ) Notice: Subject to any disclaimer, the term of this patent is extended or adjusted under 35 U.S.C. 154(b) by 136 days.

(21) Appl. No.: 17/169,209

(22) Filed: Feb. 5, 2021

(65) Prior Publication Data
US 2021/0403516 A1   Dec. 30, 2021

Related U.S. Application Data

(62) Division of application No. 15/575,309, filed as application No. PCT/EP2016/061071 on May 18, 2016, now Pat. No. 10,913,778.

(30) Foreign Application Priority Data

May 18, 2015   (EP) ..................................... 15167927
Jan. 8, 2016   (EP) ..................................... 16150508

(51) Int. Cl.
| C07K 14/47 | (2006.01) |
| A61P 35/00 | (2006.01) |
| C07K 14/705 | (2006.01) |
| C07K 16/28 | (2006.01) |
| C07K 16/32 | (2006.01) |

(52) U.S. Cl.
CPC .............. *C07K 14/47* (2013.01); *A61P 35/00* (2018.01); *C07K 14/70575* (2013.01); *C07K 16/2878* (2013.01); *C07K 16/32* (2013.01); *C07K 2317/92* (2013.01); *C07K 2319/33* (2013.01)

(58) Field of Classification Search
CPC .............. C07K 14/47; C07K 14/70575; C07K 16/2878; C07K 16/32; C07K 2317/92; C07K 2319/33; A61P 35/00
See application file for complete search history.

(56) References Cited

U.S. PATENT DOCUMENTS 10,156,559 B2 * 12/2018 Olson ..................... A61P 29/00

OTHER PUBLICATIONS

Lee YL, et al. (Nov. 2011) J Pept Sci. 17(11):763-9. (doi: 10.1002/psc.1400. Epub Oct. 4, 2011).*
Wang J, et al. (Dec. 15, 2010) J Immunol. 185(12):7654-7662. (Published online Nov. 8, 2010. doi: 10.4049/jimmunol. 1000927).*
Skerra A. (Apr. 24, 2008) The FEBS Journal. 275(11):2677-2683. (https://doi.org/10.1111/j.1742-4658.2008.06439.x).*
Trinh R, et al. (Jan. 2004) Mol Immunol. 40(10):717-22. (doi: 10.1016/j.molimm.2003.08.006).*

* cited by examiner

*Primary Examiner* — Robert S Landsman
(74) *Attorney, Agent, or Firm* — Morgan, Lewis & Bockius LLP

(57) ABSTRACT

The disclosure provides a fusion polypeptide specific for both CD137 and GPC3, which fusion polypeptide can be useful for directing CD137 clustering and activation to GPC3-positive tumor cells. Such fusion polypeptide can be used in many pharmaceutical applications, for example, as anti-cancer agents and/or immune modulators for the treatment or prevention of human diseases such as a variety of tumors. The present disclosure also concerns methods of making the fusion polypeptide described herein as well as compositions comprising such fusion polypeptide. The present disclosure further relates to nucleic acid molecules encoding such fusion polypeptide and to methods for generation of such fusion polypeptide and nucleic acid molecules. In addition, the application discloses therapeutic and/or diagnostic uses of such fusion polypeptide as well as compositions comprising one or more of such fusion polypeptides.

6 Claims, 17 Drawing Sheets

Figure 3:
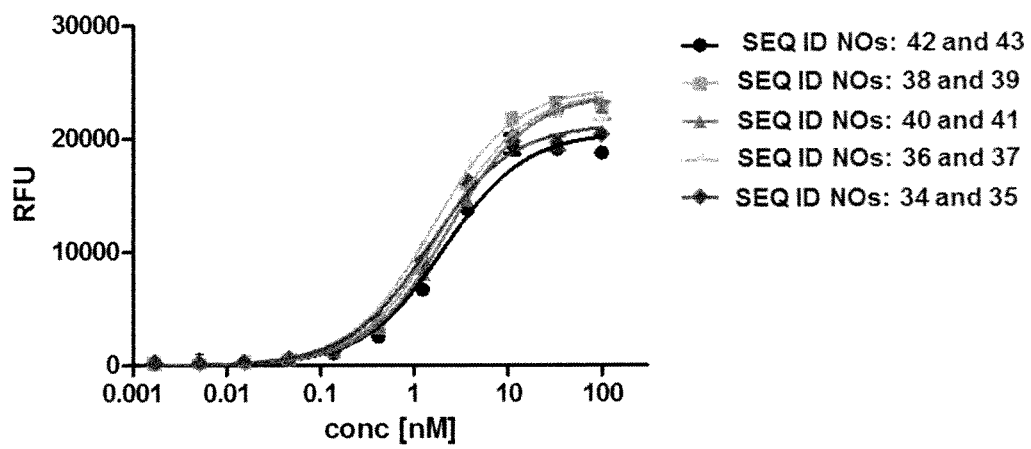

Specification includes a Sequence Listing.

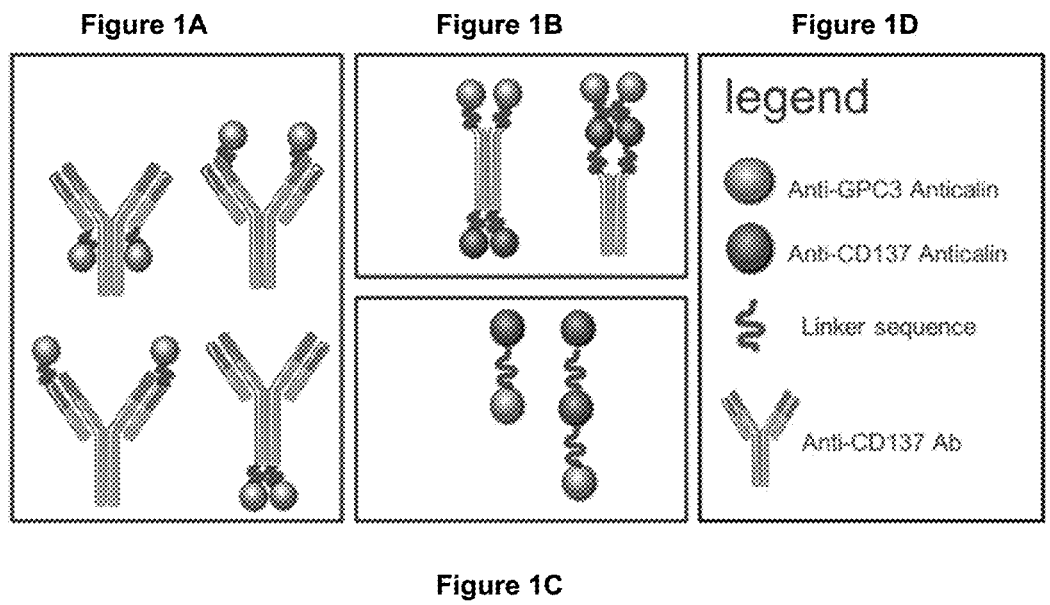
Figure 1A  Figure 1B  Figure 1D
Figure 1C
Figure 2
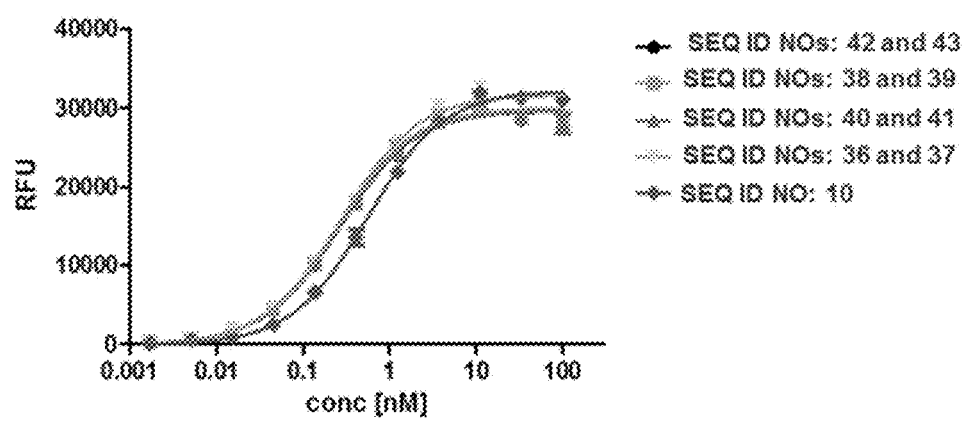

SEQ ID NO: 10

SEQ ID NOs: 36 and 37

SEQ ID NOs: 42 and 43

SEQ ID NOs: 38 and 39

SEQ ID NOs: 40 and 41

SEQ ID NO: 10

SEQ ID NOs: 36 and 37

SEQ ID NOs: 42 and 43

SEQ ID NOs: 38 and 39

SEQ ID NOs: 40 and 41

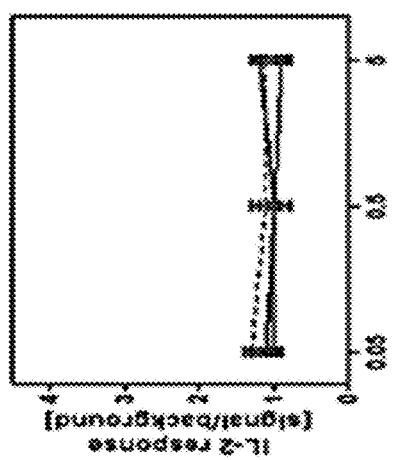
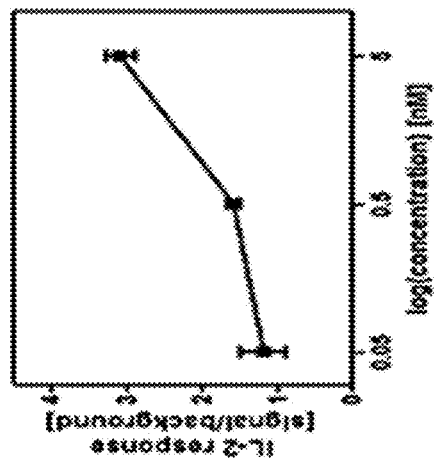
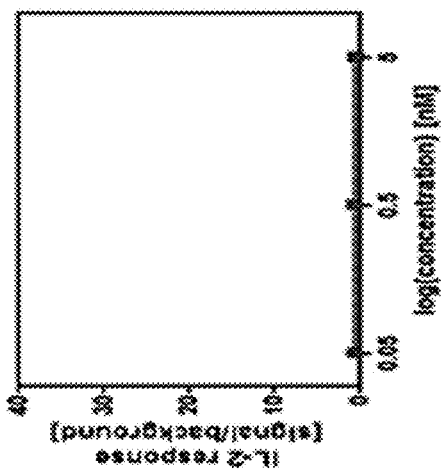
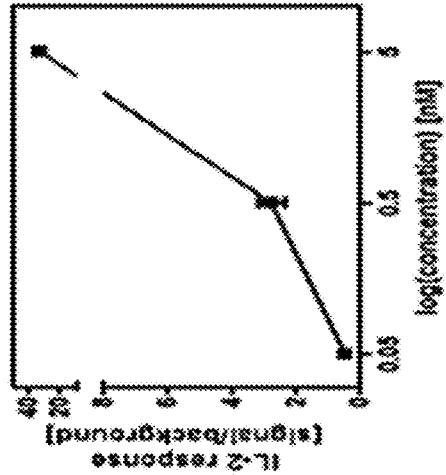
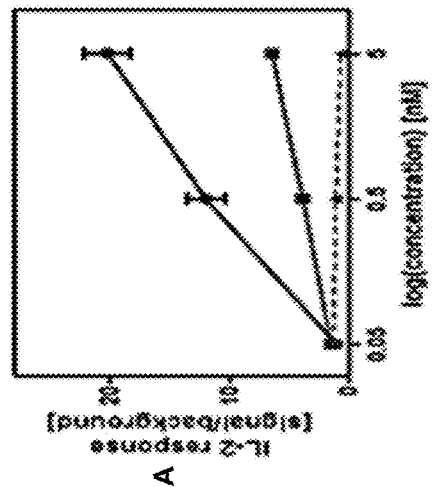
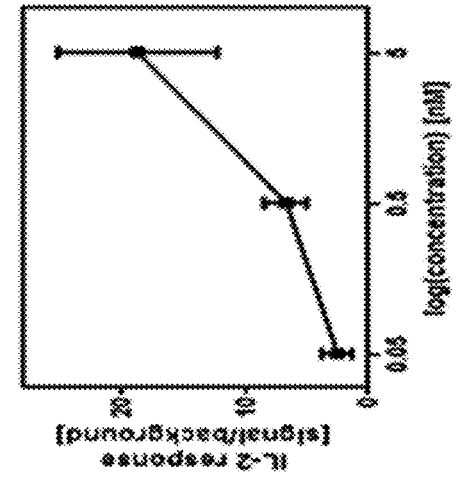
Figure 22A
Figure 22B

ANTI-CANCER FUSION POLYPEPTIDE CAPABLE OF BINDING BOTH CD137 AND GLYPICAN-3 (GPC3)

CROSS REFERENCE TO RELATED APPLICATIONS

This application is a divisional application of U.S. patent application Ser. No. 15/575,309, filed Nov. 17, 2017, now U.S. Pat. No. 10,913,778, which is a national stage entry of International Patent Application No. PCT/EP2016/061071, filed May 18, 2016, which claims priority to European Patent Application No. 16150508.6, filed Jan. 8, 2016, and European Patent Application No. 15167927.1, filed May 18, 2015.

I. BACKGROUND

Glypican-3 (GPC3) is an oncofetal antigen that belongs to the glypican family of glycosyl-phosphatidylinositol-anchored heparin sulfate proteoglycans. GPC3 is expressed in fetal liver and placenta during development and is down-regulated or silenced in normal adult tissues. Mutations and depletions in the GPC3 gene are responsible for the Simpson-Golabi-Behmel or Simpson dysmorphia syndrome in humans. GPC3 is expressed in various cancers and, in particular, hepatocellular carcinoma ("HCC"), melanoma, Merkel cell carcinoma, Wilm's tumor, and hepatoblastoma. (He, H. et al Applied Immunohistochem Mol Morphol. 17:40-6 (2009); Jakubovic and Jothy; Ex. Mol. Path. 82:184-189 (2007); Nakatsura and Nishimura, Biodrugs 19(2):71-77 (2005).). HCC is the third leading cause of cancer-related deaths worldwide. Each year, HCC accounts for about 1 million deaths. (Nakatsura and Nishimura, Biodrugs 19(2):71-77 (2005)).

Effective treatment against GPC3-expressed cancers such as HCC requires therapeutic compounds that target GPC3 and also produce anti-tumor effects.

CD137 is a co-stimulatory immune receptor and a member of the tumor necrosis factor receptor (TNFR) superfamily. It is mainly expressed on activated CD4+ and CD8+ T cells, activated B cells, and natural killer (NK) cells but can also be found on resting monocytes and dendritic cells (Li, S. Y. et al., Clin Pharmacol 2013 5(Suppl 1):47-53), or endothelial cells (Snell, L. M. et al., Immunol Rev 2011 November; 244(1):197-217). CD137 plays an important role in the regulation of immune responses and thus is a target for cancer immunotherapy. CD137 ligand (CD137L) is the only known natural ligand of CD137, and is constitutively expressed on several types of APC, such as activated B cells, monocytes, and splenic dendritic cells, and it can be induced on T lymphocytes.

CD137L is a trimeric protein that exists as a membrane-bound form and as a soluble variant. The ability of soluble CD137L to activate CD137 e.g. on CD137-expressing lymphocytes is limited, however, and large concentrations are required to elicit an effect (Wyzgol, A. et al., J Immunol 2009 Aug. 1; 183(3):1851-1861). The natural way of activation of CD137 is via the engagement of a CD137-positive cell with a CD137L-positive cell. CD137 activation is then thought to be induced by clustering through CD137L on the opposing cell, leading to signaling via TRAF1, 2 and 3 (Snell, L. M. et al., Immunol Rev 2011 November; 244(1): 197-217, Yao, S. et al., Nat Rev Drug Disc 2013 Feb.; 12(2):130-146) and further concomitant downstream effects in the CD137-positive T-cell. In the case of T-cells activated by recognition of their respective cognate targets, the effects elicited by costimulation of CD137 are a further enhanced activation, enhanced survival and proliferation, the production of pro-inflammatory cytokines and an improved capacity to kill.

The benefit of CD137 costimulation for the elimination of cancer cells has been demonstrated in a number of preclinical in-vivo models. The forced expression of CD137L on a tumor, for example, leads to tumor rejection (Melero, I. et al., Eur J Immunol 1998 Mar.; 28(3):1116-1121). Likewise, the forced expression of an anti-CD137 scFv on a tumor leads to a CD4+ T-cell and NK-cell dependent elimination of the tumor (Ye, Z. et al., Nat Med 2002 Apr.; 8(4):343-348, Zhang, H. et al., Mol Canc Ther 2006 Jan.; 5(1):149-155, Yang, Y. et al., Canc Res 2007 Mar. 1; 67(5):2339-2344). A systemically administered anti-CD137 antibody has also been demonstrated to lead to retardation of tumor growth (Martinet, O. et al., Gene Ther 2002 Jun.; 9(12):786-792).

It has been shown that CD137 is an excellent marker for naturally occurring tumor-reactive T cells in human tumors (Ye, Q. et al., Clin Canc Res: 2014 Jan. 1; 20(1):44-55), and that anti-CD137 antibodies can be employed to improve the expansion and activity of CD8+ melanoma tumor-infiltrating lymphocytes for the application in adoptive T-cell therapy (Chacon, J. A. et al., PloS One 2013 8(4):e60031).

The preclinical demonstration of the potential therapeutic benefit of CD137 costimulation has spurred the development of therapeutic antibodies targeting CD137, BMS-663513 (Jure-Kunkel, M. et al., U.S. Pat. No. 7,288,638) and PF-05082566 (Fisher, T. S. et al., Canc Immunol Immunother 2012 October; 61(10):1721-1733); both are currently in early clinical trials.

However, it has only recently been appreciated that a bivalent CD137-binder like an antibody may by itself not be sufficient to cluster CD137 on T-cells or NK-cells and lead to efficient activation, in analogy to the lack of activity of the trivalent soluble CD137L. In recent publications utilizing preclinical mouse models, in-vivo evidence has been presented that the mode of action of other anti-TNFR antibodies in fact requires the interaction of the antibodies via their Fc-part with Fc-gamma receptors on Fc-gamma-receptor expressing cells (Bulliard, Y. et al., J Exp Med 2013 Aug. 26; 210(9):1685-1693, Bulliard, Y. et al., Immunol Cell Biol 2014 July; 92(6):475-480). The mode of action of the antibodies currently in clinical development may therefore be dominated by a non-targeted clustering via Fc-gamma receptors which may be nearly randomly dependent on the presence of Fc-γ-expressing cells in the vicinity of the tumor.

Thus, there is unmet need for the generation of therapeutics that cluster and activate CD137 with a specific tumor-targeted mode of action.

To meet this unmet need, the present application, provides a novel approach of simultaneously engaging CD137 and tumor antigen GPC3 via a fusion polypeptide having the following properties:

(a) binding specificity for CD137; and
(b) binding specificity for GPC3;

This fusion polypeptide is designed to provide a tumor-target-dependent activation of CD137 on lymphocytes, via GPC3 expressed on tumor cells. Such a molecule is expected to further activate T-cells and/or NK cells that are located in the vicinity of a GPC3-positive tumor. Such a bispecific may display improved therapeutic effects over either anti-GPC3 or anti-CD137 antibodies.

II. DEFINITIONS

The following list defines terms, phrases, and abbreviations used throughout the instant specification. All terms listed and defined herein are intended to encompass all grammatical forms.

As used herein, unless otherwise specified, "CD137" means human CD137 and include variants, isoforms and species homologs of human Cd137. CD137 is also known as "4-1BB" or "tumor necrosis factor receptor superfamily member 9 (TNFRSF9)" or "induced by lymphocyte activation (ILA)". Human CD137 means a full-length protein defined by UniProt Q07011, a fragment thereof, or a variant thereof.

As used herein, unless otherwise specified, "GPC3" means human GPC3 and include variants, isoforms and species homologs of human GPC3. GPC3 is also known as "Glypican-3, "glypican proteoglycan 3," "GPC3, "OTTHUMP00000062492", "GTR2-2" "SGB," "DGSX", "SDYS", "SGBS", "OCI-5", and "SGBSI," which are used interchangeably. Human GPC3 means a full-length protein defined by UniProt P51654, a fragment thereof, or a variant thereof. As used herein, "detectable affinity" means the ability to bind to a selected target with an affinity constant of generally at least about $10^{-5}$ M or below. Lower affinities are generally no longer measurable with common methods such as ELISA and therefore of secondary importance.

As used herein, "binding affinity" of a protein of the disclosure (e.g. a mutein of a lipocalin) or a fusion polypeptide thereof to a selected target (in the present case, CD137 and/or GPC3), can be measured (and thereby KD values of a mutein-ligand complex be determined) by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Such methods are well established in the art and examples thereof are also detailed below.

It is also noted that the complex formation between the respective binder and its ligand is influenced by many different factors such as the concentrations of the respective binding partners, the presence of competitors, pH and the ionic strength of the buffer system used, and the experimental method used for determination of the dissociation constant KD (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective binder and its target/ligand) may vary within a certain experimental range, depending on the method and experimental setup that is used for determining the affinity of a particular lipocalin mutein for a given ligand. This means that there may be a slight deviation in the measured $K_D$ values or a tolerance range depending, for example, on whether the $K_D$ value was determined by surface plasmon resonance (Biacore), by competition ELISA, or by "direct ELISA."

As used herein, a "mutein," a "mutated" entity (whether protein or nucleic acid), or "mutant" refers to the exchange, deletion, or insertion of one or more nucleotides or amino acids, compared to the naturally occurring (wild-type) nucleic acid or protein "reference" scaffold. Said term also includes fragments of a mutein and variants as described herein. Lipocalin muteins of the present invention, fragments or variants thereof preferably retain the function of binding to CD137 and/or GPC3 as described herein.

The term "fragment" as used herein in connection with the muteins of the disclosure relates to proteins or peptides derived from full-length mature human tear lipocalin or human lipocalin 2 that are N-terminally and/or C-terminally shortened, i.e. lacking at least one of the N-terminal and/or C-terminal amino acids. Such fragments may include at least 10, more such as 20 or 30 or more consecutive amino acids of the primary sequence of the mature lipocalin and are usually detectable in an immunoassay of the mature lipocalin. In general, the term "fragment", as used herein with respect to the corresponding protein ligand 0D137 and/or GPC3 of a lipocalin mutein of the disclosure or of the combination according to the disclosure or of a fusion protein described herein, relates to N-terminally and/or C-terminally shortened protein or peptide ligands, which retain the capability of the full length ligand to be recognized and/or bound by a mutein according to the disclosure.

The term "mutagenesis" as used herein means that the experimental conditions are chosen such that the amino acid naturally occurring at a given sequence position of the mature lipocalin can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild-type protein. Such an insertion or deletion may be introduced independently from each other in any of the peptide segments that can be subjected to mutagenesis in the disclosure. In one exemplary embodiment of the disclosure, an insertion of several mutations may be introduced into the loop AB of the chosen lipocalin scaffold (cf. International Patent Application WO 2005/019256 which is incorporated by reference its entirety herein).

The term "random mutagenesis" means that no predetermined single amino acid (mutation) is present at a certain sequence position but that at least two amino acids can be incorporated with a certain probability at a predefined sequence position during mutagenesis.

"Identity" is a property of sequences that measures their similarity or relationship. The term "sequence identity" or "identity" as used in the present disclosure means the percentage of pair-wise identical residues—following (homologous) alignment of a sequence of a polypeptide of the disclosure with a sequence in question—with respect to the number of residues in the longer of these two sequences. Sequence identity is measured by dividing the number of identical amino acid residues by the total number of residues and multiplying the product by 100.

The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any lipocalin mutein of the disclosure).

The percentage of sequence homology or sequence identity can, for example, be determined herein using the program BLASTP, version blastp 2.2.5 (Nov. 16, 2002; cf. Altschul, S. F. et al. (1997) Nucl. Acids Res. 25, 3389-3402). In this embodiment the percentage of homology is based on the alignment of the entire polypeptide sequences (matrix: BLOSUM 62; gap costs: 11.1; cutoff value set to $10^{-3}$) including the propeptide sequences, preferably using the wild-type protein scaffold as reference in a pairwise comparison. It is calculated as the percentage of numbers of "positives" (homologous amino acids) indicated as result in the BLASTP program output divided by the total number of amino acids selected by the program for the alignment.

Specifically, in order to determine whether an amino acid residue of the amino acid sequence of a lipocalin (mutein) different from a wild-type lipocalin corresponds to a certain position in the amino acid sequence of a wild-type lipocalin, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a wild-type lipocalin can serve as "subject sequence" or "reference sequence", while the amino acid sequence of a lipocalin different from the wild-type lipocalin described herein serves as "query sequence". The terms "reference sequence" and "wild-type sequence" are used interchangeably herein. A preferred wild-type lipocalin is shown in SEQ ID NO: 1 (Tlc) or SEQ ID NO: 2 (NGAL), respectively. Dependent on whether a lipocalin mutein of the present invention is based on Tlc or NGAL, respectively, the corresponding wild-type lipocalin may be used as reference sequence or wild-type sequence.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of sequence identity. Those skilled in the art will recognize that several computer programs are available for determining sequence identity using standard parameters, for example Blast (Altschul, et al. (1997) Nucleic Acids Res. 25, 3389-3402), Blast2 (Altschul, et al. (1990) J. Mol. Biol. 215, 403-410), and Smith-Waterman (Smith, et al. (1981) J. Mol. Biol. 147, 195-197).

The term "variant" as used in the present disclosure relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. The term "variant", as used herein with respect to the corresponding protein ligand CD137 and/or GPC3 of a lipocalin mutein of the disclosure or of the combination according to the disclosure or of a fusion protein described herein, relates to CD137 or fragment thereof, respectively, that has one or more such as 1, 2, 3, 4, 5, 6, 7, 8, 9, 10, 12, 14, 16, 18, 20, 22, 24, 26, 28, 30, 40, 50, 60, 70, 80 or more amino acid substitutions, deletions and/or insertions in comparison to a wild-type CD137 or GPC3 protein, respectively, such as a CD137 or GPC3 reference protein as deposited with UniProt as described herein. A CD137 variant, respectively, has preferably an amino acid identity of at least 50%, 60%, 70%, 80%, 85%, 90% or 95% with a wild-type human CD137 or GPC3, such as a CD137 or GPC3 reference protein as deposited with UniProt as described herein.

By a "native sequence" lipocalin is meant a lipocalin that has the same amino acid sequence as the corresponding polypeptide derived from nature. Thus, a native sequence lipocalin can have the amino acid sequence of the respective naturally-occurring lipocalin from any organism, in particular a mammal. Such native sequence polypeptide can be isolated from nature or can be produced by recombinant or synthetic means. The term "native sequence" polypeptide specifically encompasses naturally-occurring truncated or secreted forms of the lipocalin, naturally-occurring variant forms such as alternatively spliced forms and naturally-occurring allelic variants of the lipocalin. A polypeptide "variant" means a biologically active polypeptide having at least about 50%, 60%, 70%, 80% or at least about 85% amino acid sequence identity with the native sequence polypeptide. Such variants include, for instance, polypeptides in which one or more amino acid residues are added or deleted at the N- or C-terminus of the polypeptide. Generally, a variant has at least about 70%, including at least about 80%, such as at least about 85% amino acid sequence identity, including at least about 90% amino acid sequence identity or at least about 95% amino acid sequence identity with the native sequence polypeptide. As an illustrative example, the first 4 N-terminal amino acid residues (His-His-Leu-Leu) and the last 2 C-terminal amino acid residues (Ser-Asp) can be deleted in a tear lipocalin (Tlc) mutein of the disclosure without affecting the biological function of the protein. In addition, as another illustrative example, certain amino acid residues can be deleted in a lipocalin 2 (NGAL) mutein of the disclosure without affecting the biological function of the protein, e.g. (Lys-Asp-Pro, positions 46-48).

The term "position" when used in accordance with the disclosure means the position of either an amino acid within an amino acid sequence depicted herein or the position of a nucleotide within a nucleic acid sequence depicted herein. To understand the term "correspond" or "corresponding" as used herein in the context of the amino acid sequence positions of one or more lipocalin muteins, a corresponding position is not only determined by the number of the preceding nucleotides/amino acids. Accordingly, the position of a given amino acid in accordance with the disclosure which may be substituted may vary due to deletion or addition of amino acids elsewhere in a (mutant or wild-type) lipocalin. Similarly, the position of a given nucleotide in accordance with the present disclosure which may be substituted may vary due to deletions or additional nucleotides elsewhere in a mutein or wild-type lipocalin 5'-untranslated region (UTR) including the promoter and/or any other regulatory sequences or gene (including exons and introns).

Thus, for a corresponding position in accordance with the disclosure, it is preferably to be understood that the positions of nucleotides/amino acids may differ in the indicated number than similar neighboring nucleotides/amino acids, but said neighboring nucleotides/amino acids, which may be exchanged, deleted, or added, are also comprised by the one or more corresponding positions.

In addition, for a corresponding position in a lipocalin mutein based on a reference scaffold in accordance with the disclosure, it is preferably to be understood that the positions of nucleotides/amino acids are structurally corresponding to the positions elsewhere in a (mutant or wild-type) lipocalin, even if they may differ in the indicated number, as appreciated by the skilled in light of the highly-conserved overall folding pattern among lipocalins.

The word "detect", "detection", "detectable" or "detecting" as used herein is understood both on a quantitative and a qualitative level, as well as a combination thereof. It thus includes quantitative, semi-quantitative and qualitative measurements of a molecule of interest.

A "subject" is a vertebrate, preferably a mammal, more preferably a human. The term "mammal" is used herein to refer to any animal classified as a mammal, including, without limitation, humans, domestic and farm animals, and zoo, sports, or pet animals, such as sheep, dogs, horses, cats, cows, rats, pigs, apes such as cynomolgus monkeys and etc., to name only a few illustrative examples. Preferably, the mammal herein is human.

An "effective amount" is an amount sufficient to effect beneficial or desired results. An effective amount can be administered in one or more administrations.

A "sample" is defined as a biological sample taken from any subject. Biological samples include, but are not limited to, blood, serum, urine, feces, semen, or tissue.

A "subunit" of a fusion polypeptide disclosed herein is defined as a stretch of amino acids of the polypeptide, which stretch defines a unique functional unit of said polypeptide such as provides binding motif towards a target.

A "fusion polypeptide" as described herein comprises two or more subunits, at least one of these subunits binds to GPC3 and a further subunit binds to CD137. Within the fusion polypeptide, these subunits may be linked by covalent or non-covalent linkage. Preferably, the fusion polypeptide is a translational fusion between the two or more subunits. The translational fusion may be generated by genetically engineering the coding sequence for one subunit in frame with the coding sequence of a further subunit. Both subunits may be interspersed by a nucleotide sequence encoding a linker. However, the subunits of a fusion polypeptide of the present disclosure may also be linked by a chemical linker.

A "linker" that may be comprised by a fusion polypeptide of the present disclosure links two or more subunits of a fusion polypeptide as described herein. The linkage can be covalent or non-covalent. A preferred covalent linkage is via a peptide bond, such as a peptide bond between amino acids. Accordingly, in a preferred embodiment said linker comprises of one or more amino acids, such as 1, 2, 3, 4, 5, 6, 7, 8, 9, 10, 11, 12, 13, 14, 15, 16, 17, 18, 19, 20 or more amino acids. Preferred linkers are described herein. Other preferred linkers are chemical linkers.

III. DESCRIPTIONS OF FIGURES

FIGS. 1A-D: provides an overview over the design of the fusion polypeptides described in this application, which are bispecific with regard to the targets GPC3 and CD137. Three different approaches were employed: in FIG. 1A the first set of fusion polypeptides is based on an antibody specific for CD137 (for example, the antibody of SEQ ID NOs: 34 and 35) and a lipocalin mutein specific for GPC3 (for example, the lipocalin mutein of SEQ ID NO: 10). The generated polypeptides are single fusions of the lipocalin mutein to either one of the four termini of the antibody. All fusions are linked by a linker such as a flexible (G4S)3 linker (for example, the linker of SEQ ID NO: 49); in FIG. 1B the second set of fusion polypeptides is based on two lipocalin muteins (for example, GPC3-specific lipocalin mutein of SEQ ID NO: 10 and CD137-specific lipocalin mutein of SEQ ID NO: 26), fused to an engineered IgG4-Fc fragment (SEQ ID NO: 73); and in FIG. 1C the third set of fusion proteins is based on two lipocalin muteins (for example, SEQ ID NO: 10 and SEQ ID NO: 26), linked by one or more linkers such as (G4S)2 linkers (for example, the linkers of SEQ ID NO: 48), whereby a GPC3-specific lipocalin mutein is fused to CD137-specific lipocalin mutein (for example, in SEQ ID NO: 46) or a GPC3-specific lipocalin mutein and two CD137-specific lipocalin muteins are fused together (for example, in SEQ ID NO: 47). FIG. 1D provides a legend identifying the symbols used in FIGS. 1A-C.

FIG. 2: provides a representative experiment in which the specificity of the fusion polypeptides of SEQ ID NOs: 36 and 37, SEQ ID NOs: 38 and 39, SEQ ID NOs: 40 and 41 and SEQ ID NOs: 42 and 43 and the lipocalin mutein of SEQ ID NO: 10 against the target GPC3 was determined. GPC3 was coated on a microtiter plate and the tested molecules were titrated. Bound molecules were detected via an HRP-labeled anti-human NGAL-specific antibody as described in Example 2. The data was fitted with a 1:1 binding model with EC50 value and the maximum signal as free parameters, and a slope that was fixed to unity. The resulting EC50 values are provided in Table 1.

FIG. 3: provides a representative experiment in which the specificity of the fusion polypeptides of SEQ ID NOs: 36 and 37, SEQ ID NOs: 38 and 39, SEQ ID NOs: 40 and 41 and the antibody of SEQ ID NOs: 34 and 35 against the target CD137 was determined. An Fc-fusion of human CD137 was coated on a microtiter plate, and the tested molecules were titrated. Bound molecules were detected via an HRP-labeled anti-human IgG Fc antibody as described in Example 3. The data was fitted with a 1:1 binding model with EC50 value and the maximum signal as free parameters, and a slope that was fixed to unity. The resulting EC50 values are provided in Table 2.

Figure 4:
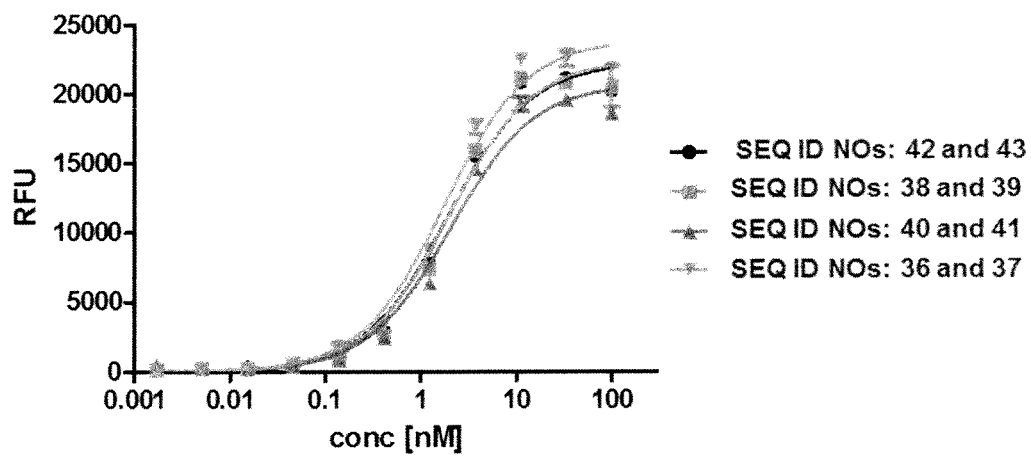

FIG. 4: provides a representative experiment in which the ability of the fusion polypeptides of SEQ ID NOs: 36 and 37, SEQ ID NOs: 38 and 39, SEQ ID NOs: 40 and 41 to bind both targets, GPC3 and CD137, simultaneously was determined. Recombinant CD137-Fc fusion protein was coated on a microtiter plate, followed by a titration of the fusion protein. Subsequently, a constant concentration of biotinylated human GPC3 was added, which was detected via HRP-labeled extravidin as described in Example 4. The data was fitted with a 1:1 binding model with EC50 value and the maximum signal as free parameters, and a slope that was fixed to unity. The resulting EC50 values are provided in Table 3.

Figure 5:
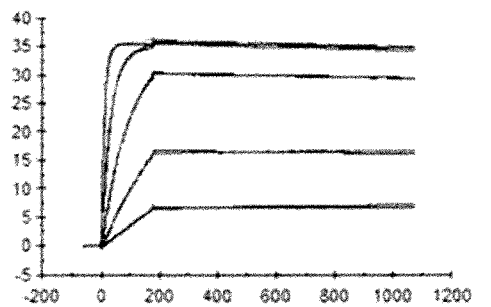
Figure 5:
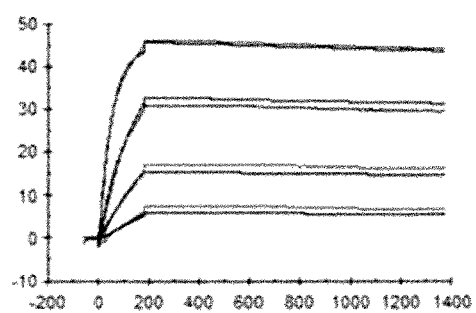
Figure 5:
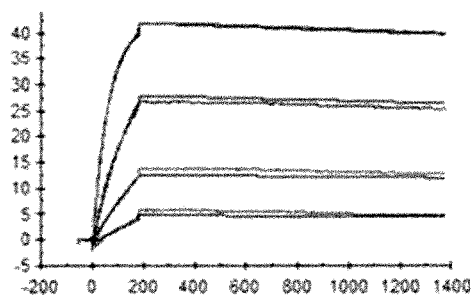
Figure 5:
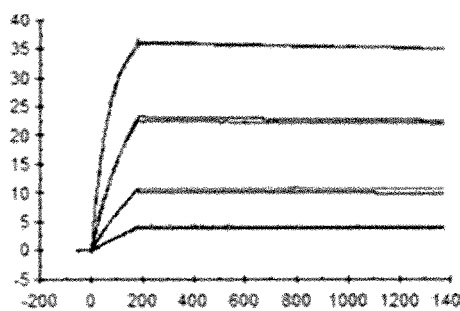
Figure 5:
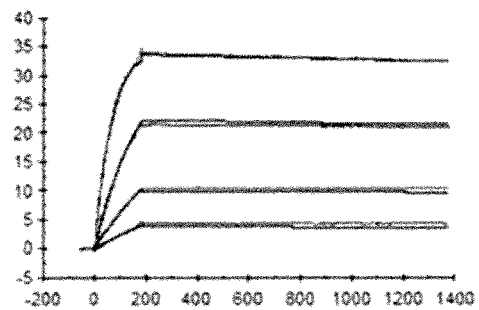

FIG. 5: provides a representative experiment in which the affinity of the fusion polypeptides of SEQ ID NOs: 36 and 37, SEQ ID NOs: 38 and 39, SEQ ID NOs: 40 and 41 and the lipocalin mutein SEQ ID NO: 10 towards the target GPC3 was determined through surface plasmon resonance (SPR). Biotinlated GPC3 was immobilized on sensor chip and binding of the fusion polypeptides and lipocalin mutein was analyzed at different concentrations as described in Example 5. The resulting $K_D$ values are provided in Table 4.

Figure 6:
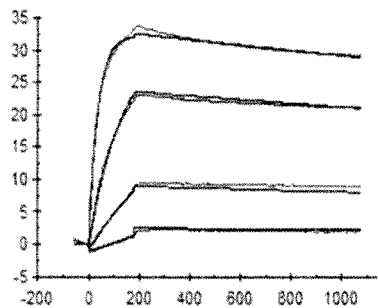
Figure 6:
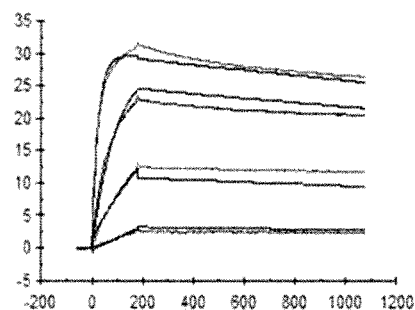
Figure 6:
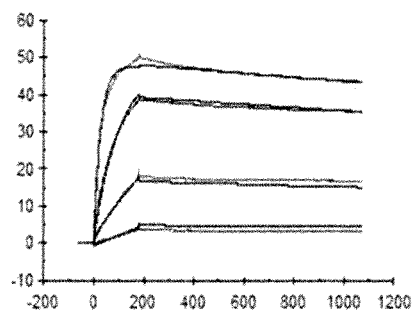
Figure 6:
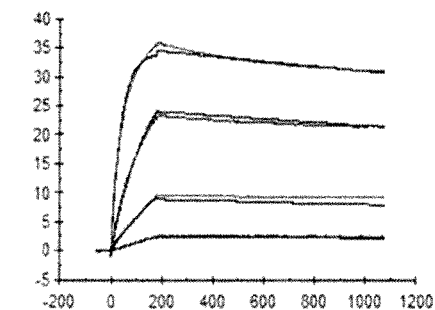
Figure 6:
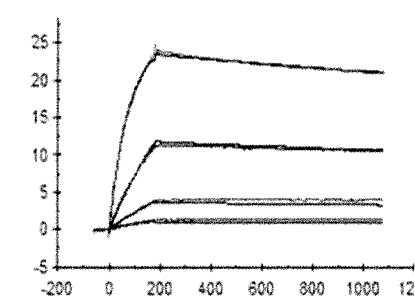

FIG. 6: provides a representative experiment in which the affinity of the fusion polypeptides of SEQ ID NOs: 36 and 37, SEQ ID NOs: 38 and 39, SEQ ID NOs: 40 and 41 and the antibody of SEQ ID NOs: 34 and 35 towards biotinylated CD137-Fc fusion was determined through surface plasmon resonance (SPR). Biotinlated CD137-Fc was immobilized on a sensor chip and binding of the fusion proteins was analyzed at different concentrations as described in Example 6. The resulting $K_D$ values are provided in Table 5.

Figure 7:
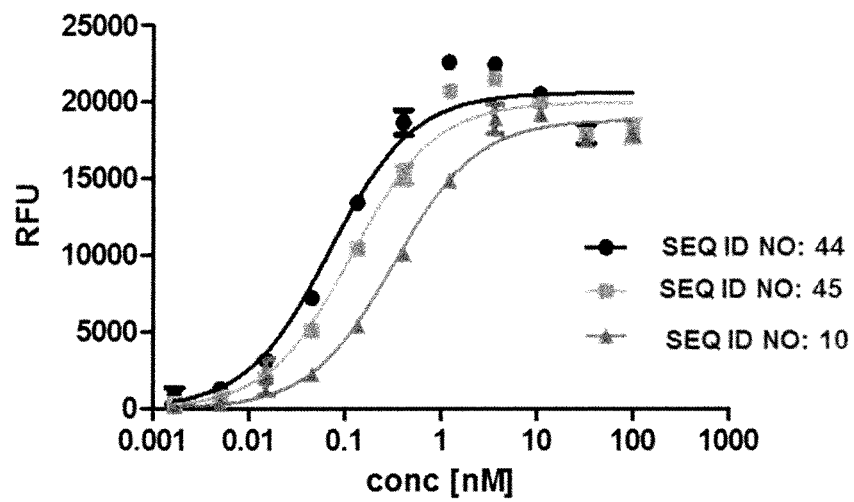

FIG. 7: provides a representative experiment in which the specificity of the lipocalin mutein-Fc fusion polypeptides of SEQ ID NO: 44 and SEQ ID NO: 45 and the lipocalin mutein of SEQ ID NO: 10 against the target GPC3 was determined. GPC3 was coated on a microtiter plate and the tested molecules were titrated. Bound molecules were detected via an HRP-labeled anti-human NGAL-specific antibody as described in Example 7. The data was fitted with a 1:1 binding model with EC50 value and the maximum signal as free parameters, and a slope that was fixed to unity. The resulting EC50 values are provided in Table 6.

Figure 8:
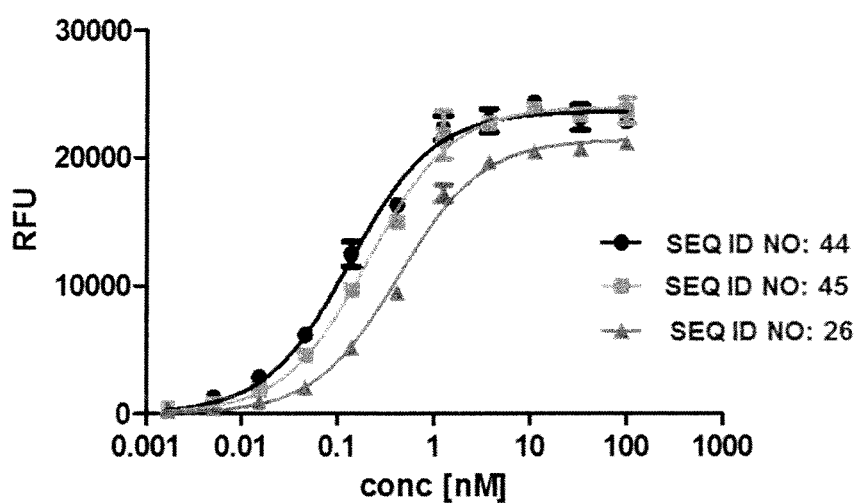

FIG. 8: provides a representative experiment in which the specificity of lipocalin mutein-Fc fusion polypeptides of SEQ ID NO: 44 and SEQ ID NO: 45 and the lipocalin mutein of SEQ ID NO: 26 against CD137 was determined. An Fc-fusion of human CD137 was coated on a microtiter plate, and the tested molecules were titrated. Bound molecules were detected via an HRP-labeled anti-human IgG Fc antibody as described in Example 8. The data was fitted with a 1:1 binding model with EC50 value and the maximum signal as free parameters, and a slope that was fixed to unity. The resulting EC50 values are provided in Table 7.

Figure 9:
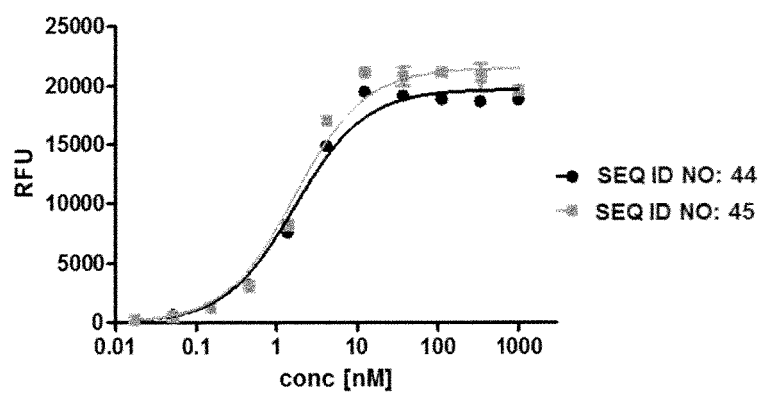

FIG. 9: provides a representative experiment in which the ability of lipocalin mutein-Fc fusion polypeptides of SEQ ID NO: 44 and SEQ ID NO: 45 to bind the targets, GPC3 and CD137, simultaneously was determined. Recombinant CD137-Fc fusion protein was coated on a microtiter plate, followed by a titration of the lipocalin mutein-Fc fusion polypeptides. Subsequently, a constant concentration of biotinylated human GPC3 was added, which was detected via HRP-labeled extravidin as described in Example 9. The data was fitted with a 1:1 binding model with EC50 value and the maximum signal as free parameters, and a slope that was fixed to unity. The resulting EC50 values are provided in Table 8.

Figure 10:
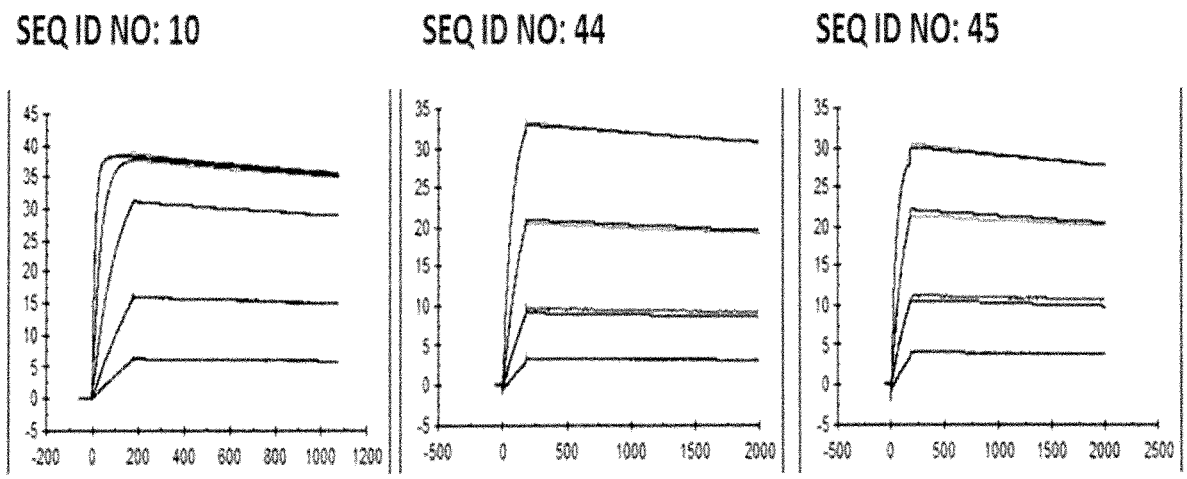

FIG. 10: provides a representative experiment in which the affinity of lipocalin mutein-Fc fusion polypeptides of SEQ ID NO: 44 and SEQ ID NO: 45 and the lipocalin mutein of SEQ ID NO: 10 towards the target GPC3 was determined through surface plasmon resonance (SPR). Biotinlated GPC3 was immobilized on a sensor chip and binding of the fusion polypeptides and lipocalin mutein was analyzed at different concentrations. The resulting $K_D$ values are provided in Table 9.

Figure 11:
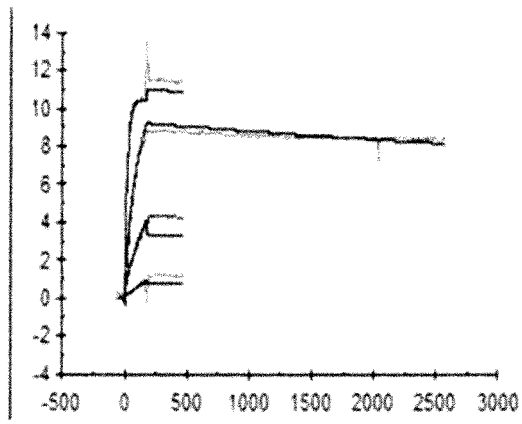
Figure 11:
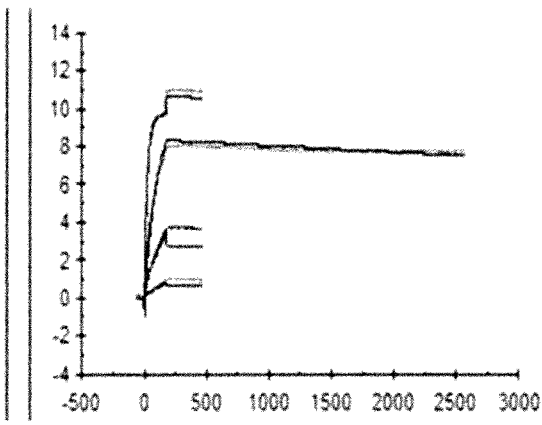

FIG. 11: provides a representative experiment in which the affinity of lipocalin mutein-Fc fusion polypeptides of SEQ ID NO: 44 and SEQ ID NO: 45 and the lipocalin mutein of SEQ ID NO: 26 towards biotinylated CD137-Fc was determined through surface plasmon resonance (SPR). Biotinlated CD137-Fc was immobilized on sensor chip and binding of the fusion polypeptides and lipocalin mutein was analyzed at different concentrations. The resulting $K_D$ values are provided in Table 10.

Figure 12:
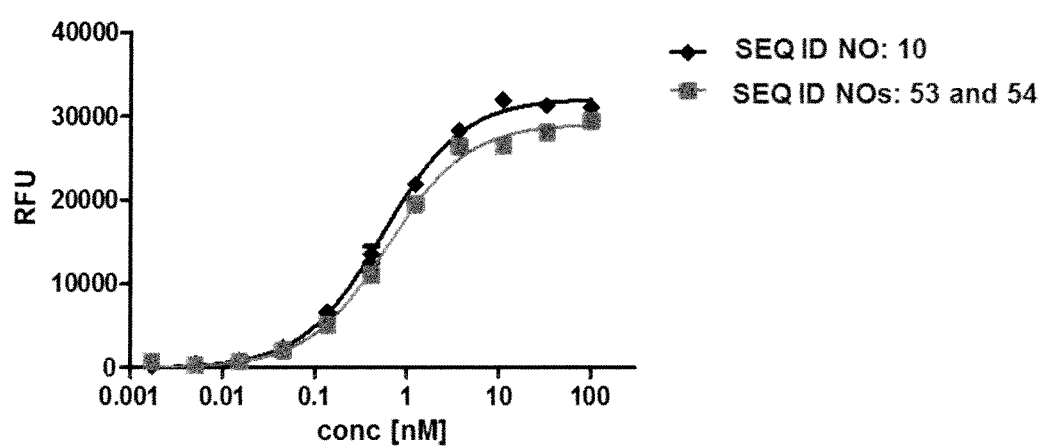

FIG. 12: provides a representative experiment in which the specificity of the fusion polypeptide of SEQ ID NOs: 53 and 54 and the lipocalin mutein of SEQ ID NO: 10 against the target GPC3 was determined. GPC3 was coated on a microtiter plate and the tested molecules were titrated. Bound molecules were detected via an HRP-labeled anti-human NGAL-specific antibody as described in Example 12. The data was fitted with a 1:1 binding model with EC50 value and the maximum signal as free parameters, and a slope that was fixed to unity. The resulting EC50 values are provided in Table 11.

Figure 13:
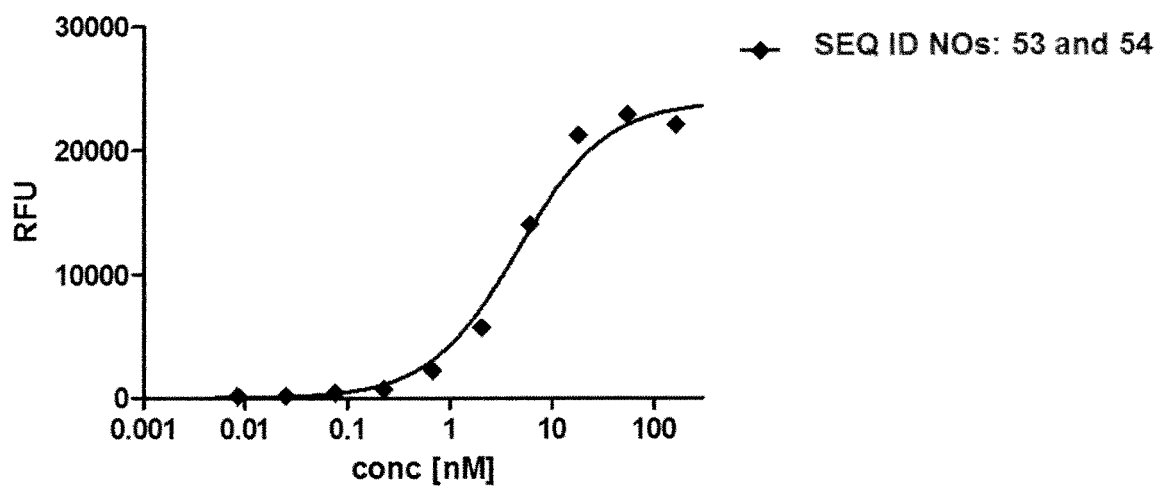

FIG. 13: provides a representative experiment in which the ability of the fusion polypeptide of SEQ ID NOs: 53 and 54 to bind both targets, GPC3 and CD137, simultaneously was determined. Recombinant CD137-Fc fusion protein was coated on a microtiter plate, followed by a titration of the fusion protein. Subsequently, a constant concentration of biotinylated human GPC3 was added, which was detected via HRP-labeled extravidin as described in Example 13. The data was fitted with a 1:1 binding model with EC50 value and the maximum signal as free parameters, and a slope that was fixed to unity.

Figure 14:
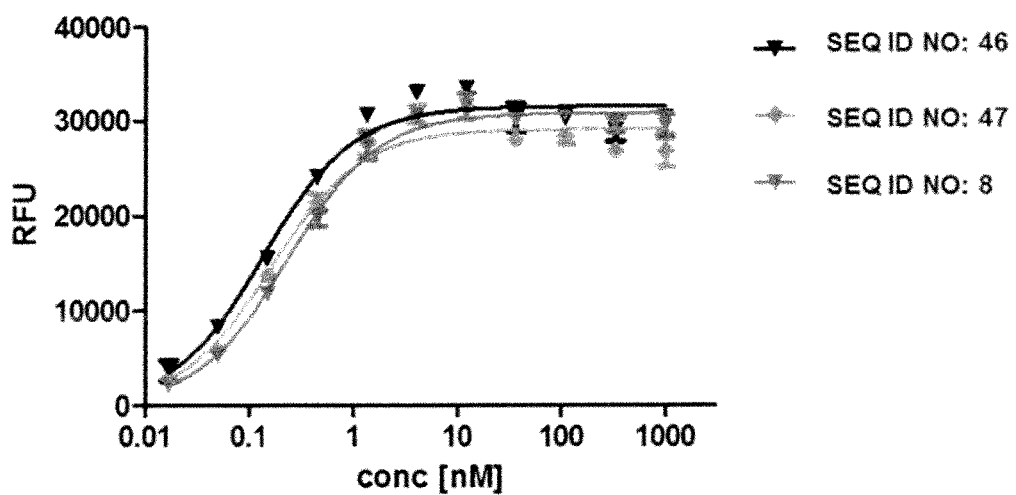

FIG. 14: provides a representative experiment in which the specificity of two bispecific fusion polypeptides SEQ ID NO: 46 and SEQ ID NO: 47 and the lipocalin mutein of SEQ ID NO: 8 against the target GPC3 was determined. GPC3 was coated on a microtiter plate and the tested molecules were titrated. Bound molecules were detected via an HRP-labeled human NGAL-specific antibody as described in Example 14. The data was fitted with a 1:1 binding model with EC50 value and the maximum signal as free parameters, and a slope that was fixed to unity. The resulting EC50 values are provided in Table 12.

Figure 15:
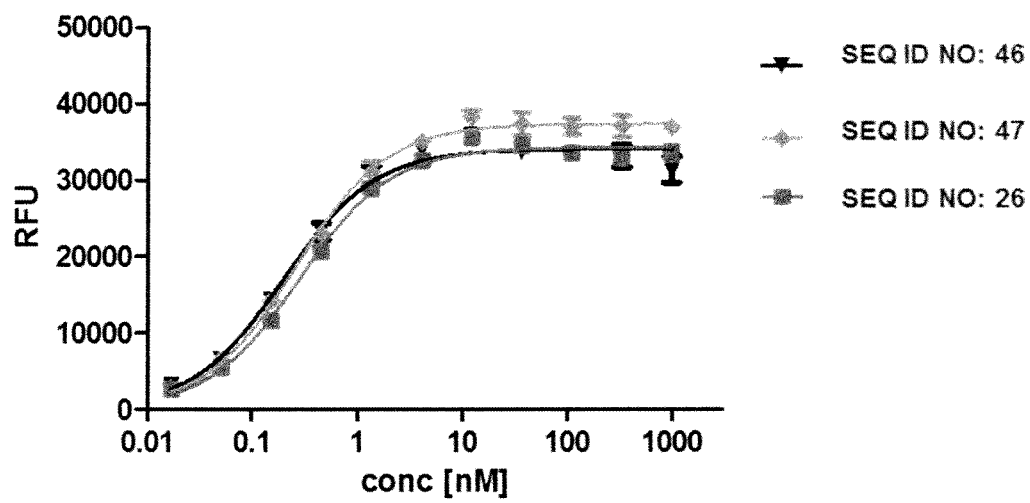

FIG. 15: provides a representative experiment in which the specificity of two bispecific fusion polypeptides of SEQ ID NO: 46 and SEQ ID NO: 47 and the lipocalin mutein of SEQ ID NO: 26 against the target CD137 was determined. An Fc-fusion of human CD137 was coated on a microtiter plate, and the tested molecules were titrated. Bound molecules were detected via an HRP-labeled anti-human IgG Fc antibody as described in Example 15. The data was fitted with a 1:1 binding model with EC50 value and the maximum signal as free parameters, and a slope that was fixed to unity. The resulting EC50 values are provided in Table 13.

Figure 16:
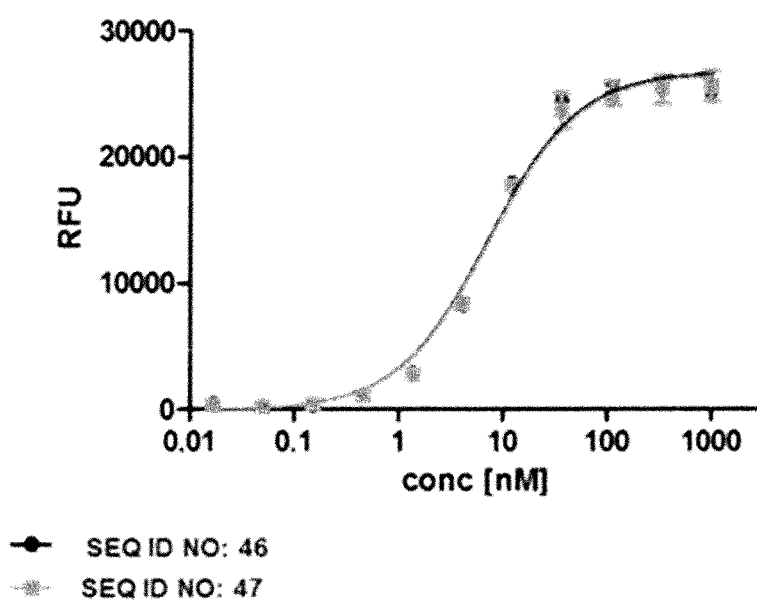

FIG. 16: provides a representative experiment in which the ability of two bispecific fusion polypeptides of SEQ ID NO: 46 and SEQ ID NO: 47 to bind the targets, GPC3 and CD137, simultaneously was determined. Recombinant CD137-Fc fusion protein was coated on a microtiter plate, followed by a titration of the fusion protein. Subsequently, a constant concentration of biotinylated human GPC3 was added, which was detected via HRP-labeled extravidin as described in Example 16. The data was fitted with a 1:1 binding model with EC50 value and the maximum signal as free parameters, and a slope that was fixed to unity. The resulting EC50 values are provided in Table 14.

Figure 17:
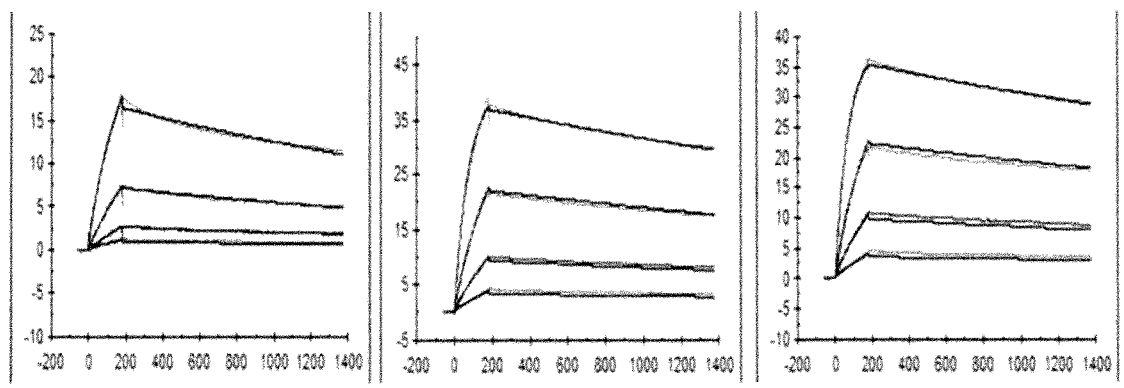

FIG. 17: provides a representative experiment in which the affinity of two bispecific fusion polypeptides of SEQ ID NO: 46 and SEQ ID NO: 47 and the lipocalin mutein of SEQ ID NO: 8 towards the target GPC3 was determined through surface plasmon resonance (SPR). Biotinylated GPC3 was immobilized on sensor chip and binding of the fusion polypeptides was analyzed at different concentrations. The resulting $K_D$ values are provided in Table 15.

Figure 18:
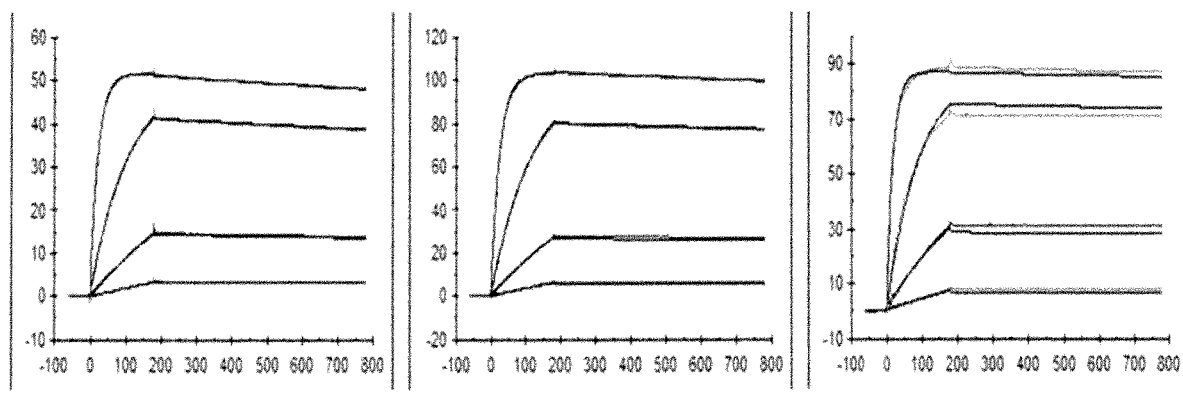

FIG. 18: provides a representative experiment in which the affinity of two bispecific fusion polypeptides of SEQ ID NO: 46 and SEQ ID NO: 47 and the lipocalin mutein SEQ ID NO: 26 towards CD137-Fc was determined through surface plasmon resonance (SPR). Human CD137-Fc was immobilized on a sensor chip and binding of the fusion proteins was analyzed at different concentrations. The resulting $K_D$ values are provided in Table 16.

Figure 19:
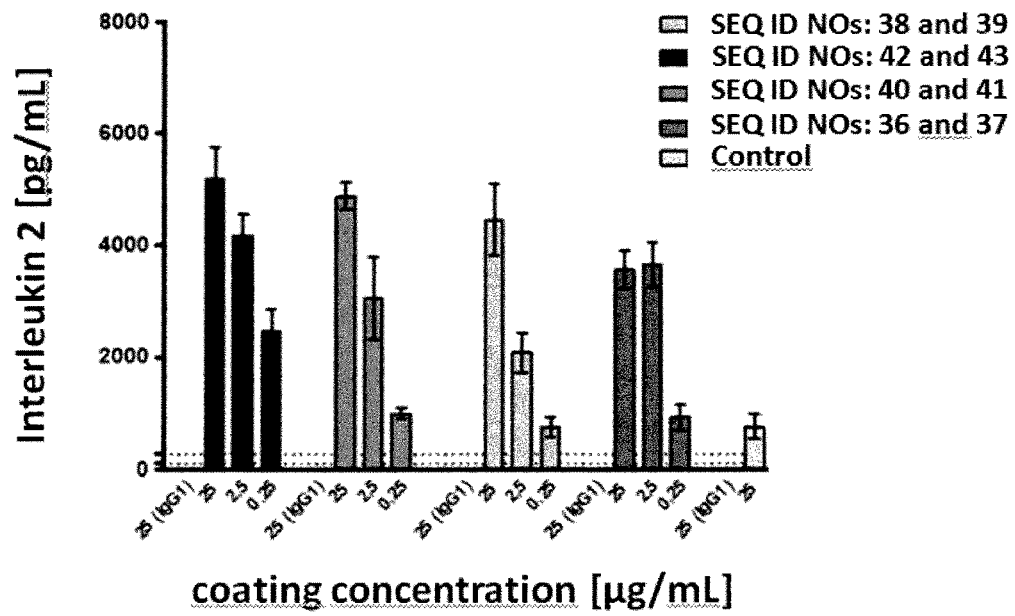

FIG. 19: provides a representative experiment in which the ability of the fusion polypeptides of SEQ ID NOs: 36 and 37, SEQ ID NOs: 38 and 39, SEQ ID NOs: 40 and 41 and SEQ ID NOs: 42 and 43 to co-stimulate T-cell responses when coated on a plastic culture dish was investigated. Fusion polypeptides at different concentrations were coated onto a plastic dish together with an anti-human CD3 antibody and purified T-cells were subsequently incubated on the coated surface in the presence of soluble anti-human CD28 antibody. Supernatant interleukin 2 (IL-2) levels were measured by electrochemiluminescence (ELC) assay as described in Example 19. As negative control, a human IgG4 isotype control was utilized.

Figure 20:
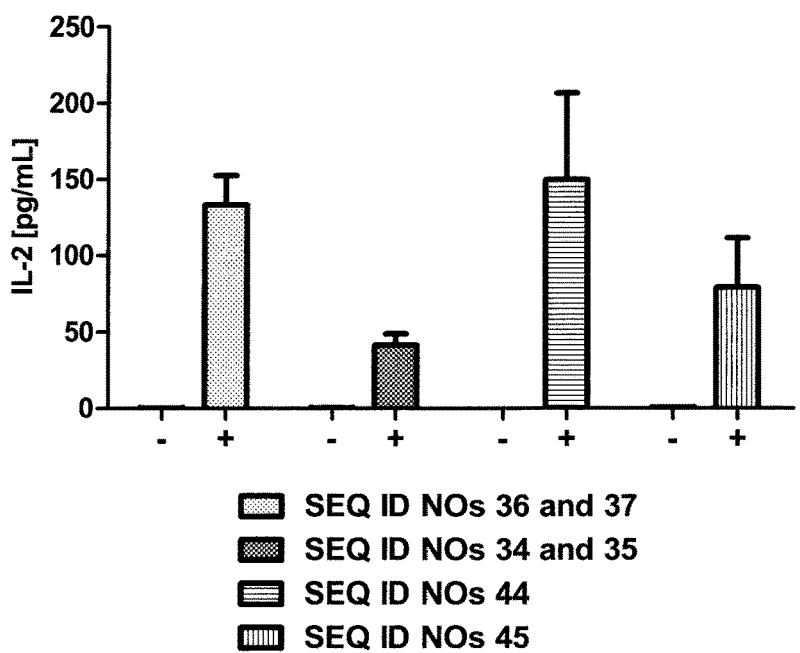

FIG. 20: provides a representative experiment in which the ability of the fusion polypeptides of SEQ ID NOs: 36 and 37, SEQ ID NOs: 44 and SEQ ID NOs: 45 to co-stimulate T-cell activation in a GPC3-target-dependent manner was investigated. As a control, we employed the monospecific, CD137-binding antibody of SEQ ID NOs: 34 and 35. In the experiment, an anti-human CD3 antibody (+) or an isotype control (−) were coated on a plastic culture dish, and subsequently GPC3-positive HepG2 cells were cultured on the dish overnight. The next day, purified T-cells were incubated on the coated surface in the presence of 1 µg/mL bispecific fusion polypeptides of SEQ ID NOs: 36 and 37, SEQ ID NOs: 44, SEQ ID NOs: 45 or the control antibody of SEQ ID NOs: 34 and 35. Supernatant interleukin 2 (IL-2) levels were measured by electrochemiluminescence (ELC) assay as described in Example 20.

Figure 21A:
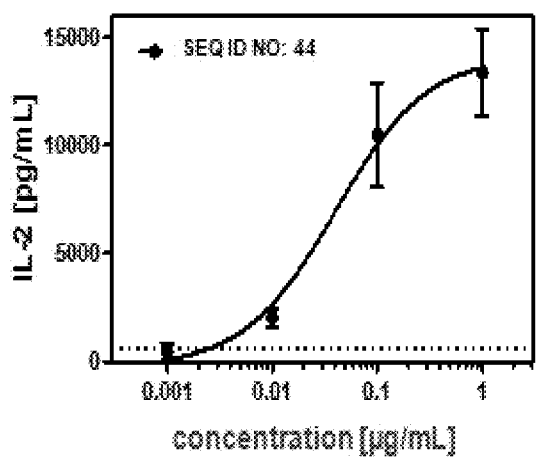
Figure 21B:
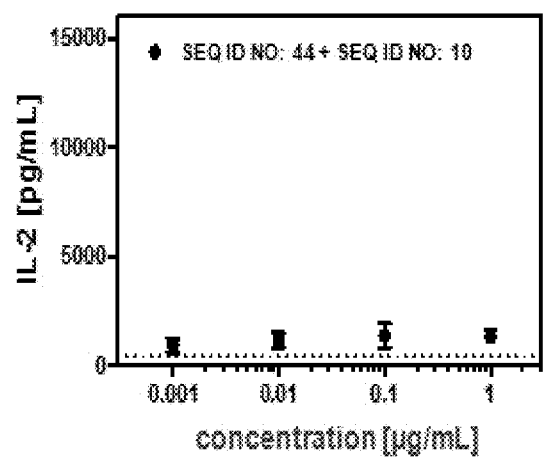
Figure 21C:
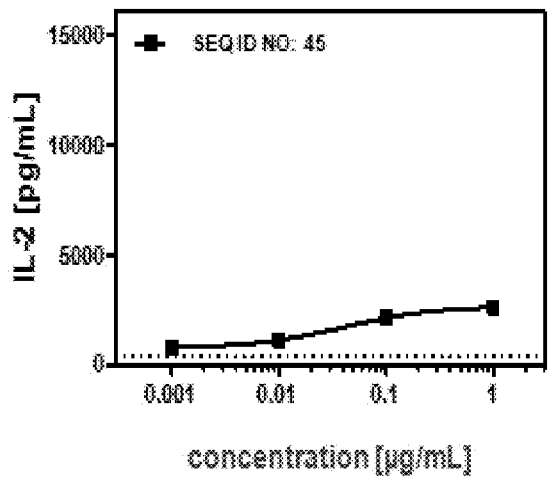
Figure 21D:
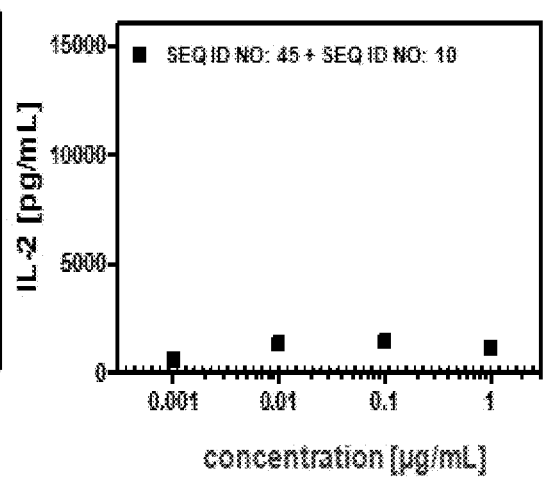

FIGS. 21A-D: provide a representative experiment in which the ability of the fusion polypeptides of SEQ ID NO: 44 and SEQ ID NO: 45 to co-stimulate T-cell activation in a GPC3-target-dependent manner was investigated. In the experiment, an anti-human CD3 antibody was coated on a plastic culture dish, and subsequently GPC3-positive Hep3B-cells were cultured on the dish overnight. The next day, purified T-cells were incubated on the coated surface in the presence of various concentrations of the bispecific fusion polypeptides of SEQ ID NO: 44 (FIG. 21A) and SEQ ID NO: 45 (FIG. 21C). Supernatant interleukin 2 (IL-2) were determined ELISA. To block the binding of the bispecific fusion polypeptides to GPC3, the experiment was also performed in the presence of an excess of SEQ ID NO: 10, both for SEQ ID NO: 44 (FIG. 21B) and SEQ ID NO: 45 (FIG. 21D). The data was fitted with a 1:1 binding model.

FIGS. 22A-B: provide a representative experiment in which the ability of the test articles to co-stimulate T-cell activation with different cell lines was investigated. Cell lines utilized were the GPC3 positive HepG2 and the GPC3 negative SKBR-3 and MCF7. In the experiment, an anti-human CD3 antibody was coated on a plastic culture dish, and subsequently the cell line under study was cultured on the dish overnight. The next day, purified T-cells were incubated on the coated surface for three days in the presence of various concentrations of the bispecific fusion polypeptides as follows: (FIG. 22A) SEQ ID NO: 44 (circles), SEQ ID NO: 45 (squares) or the control antibody trastuzumab (triangles). (FIG. 22B) Anti-CD137 antibody SEQ ID NOs: 74 and 75. Supernatant interleukin 2 levels were determined by an Electrochemoluminescence-based assay. The plotted relative IL-2 response corresponds to the ratio of the responses obtained in the presence and in the absence ("background") of test articles.

Figure 23:
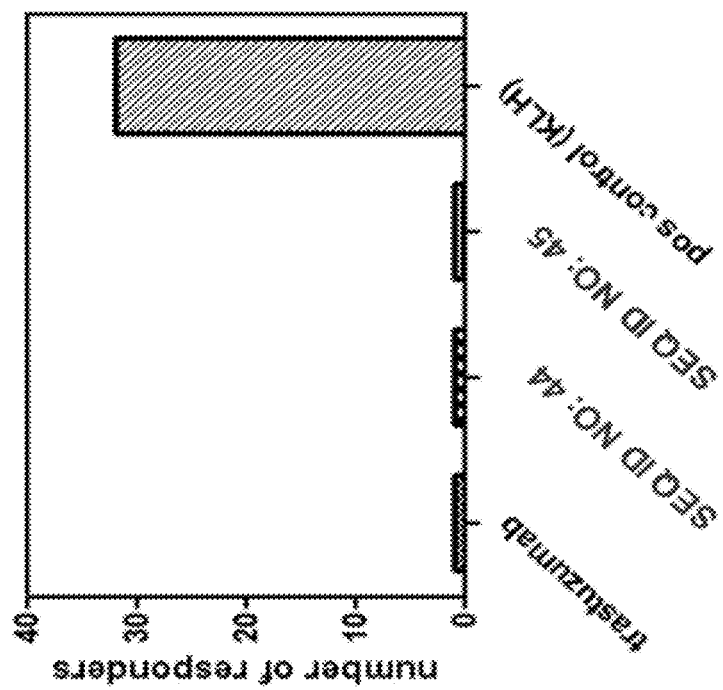
Figure 23:
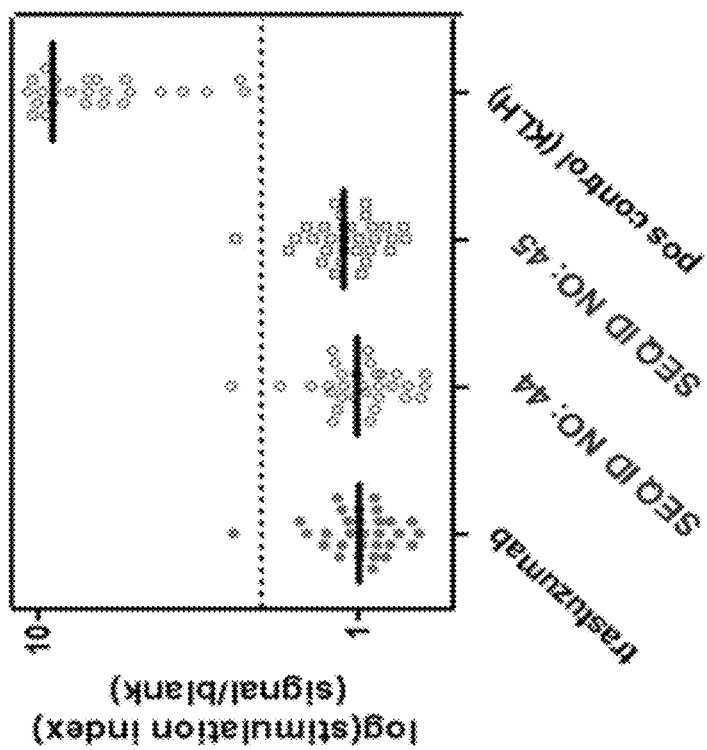

FIG. 23: provides the result of an in vitro T cell immunogenicity assessment of the bispecific fusion polypeptides, the control antibody of trastuzumab and the positive control keyhole limpet hemocyanine (KLH). The assay was performed using a PBMC-based format as described in Example 23, with 32 donors and human leukocyte antigen (HLA) allotypes reflective of the distribution in a global population: (A) Stimulation index (proliferation in the presence vs. absence of test article). The average responses are indicated as bars. The threshold that defines a responding donor (stimulation index>2) is indicated as a dotted line. (B) Number of responders.

Figure 24:
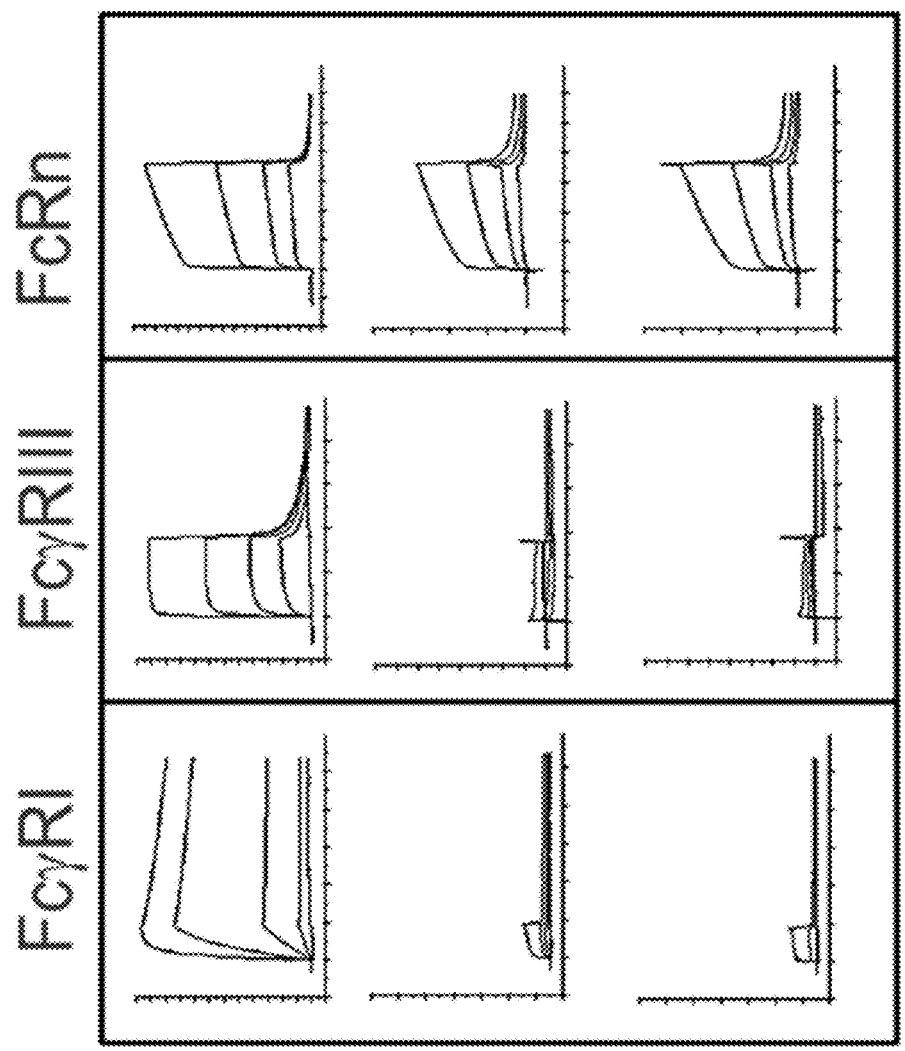

FIG. 24: provides a representative experiment on the affinity of polypeptides to FcgRI, FcgRIII and FcRn as described in Examples 24 and 25.

Figure 25:
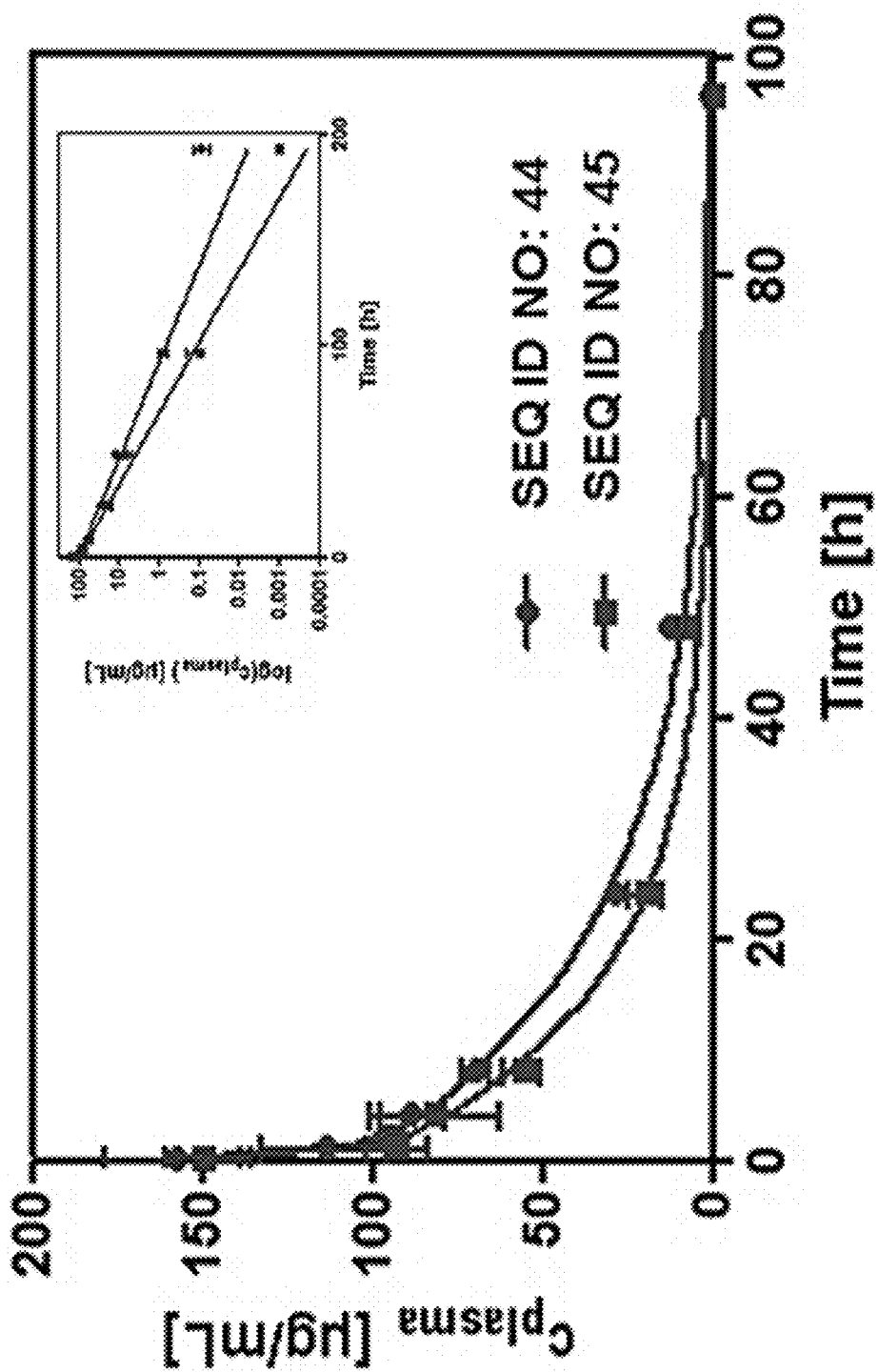

FIG. 25: provides the result of a pharmacokinetic analysis of the bispecific fusion polypeptides SEQ ID NO: 44 and SEQ ID NO: 45 in mice. Male CD-1 mice (3 mice per time point) were injected intravenously with fusion polypeptides at a dose of 10 mg/kg. Drug levels were detected using a sandwich ELISA detecting the full bispecific construct via the targets GPC3 and CD137. The data were fitted using a two-compartmental model.

Figure 26:
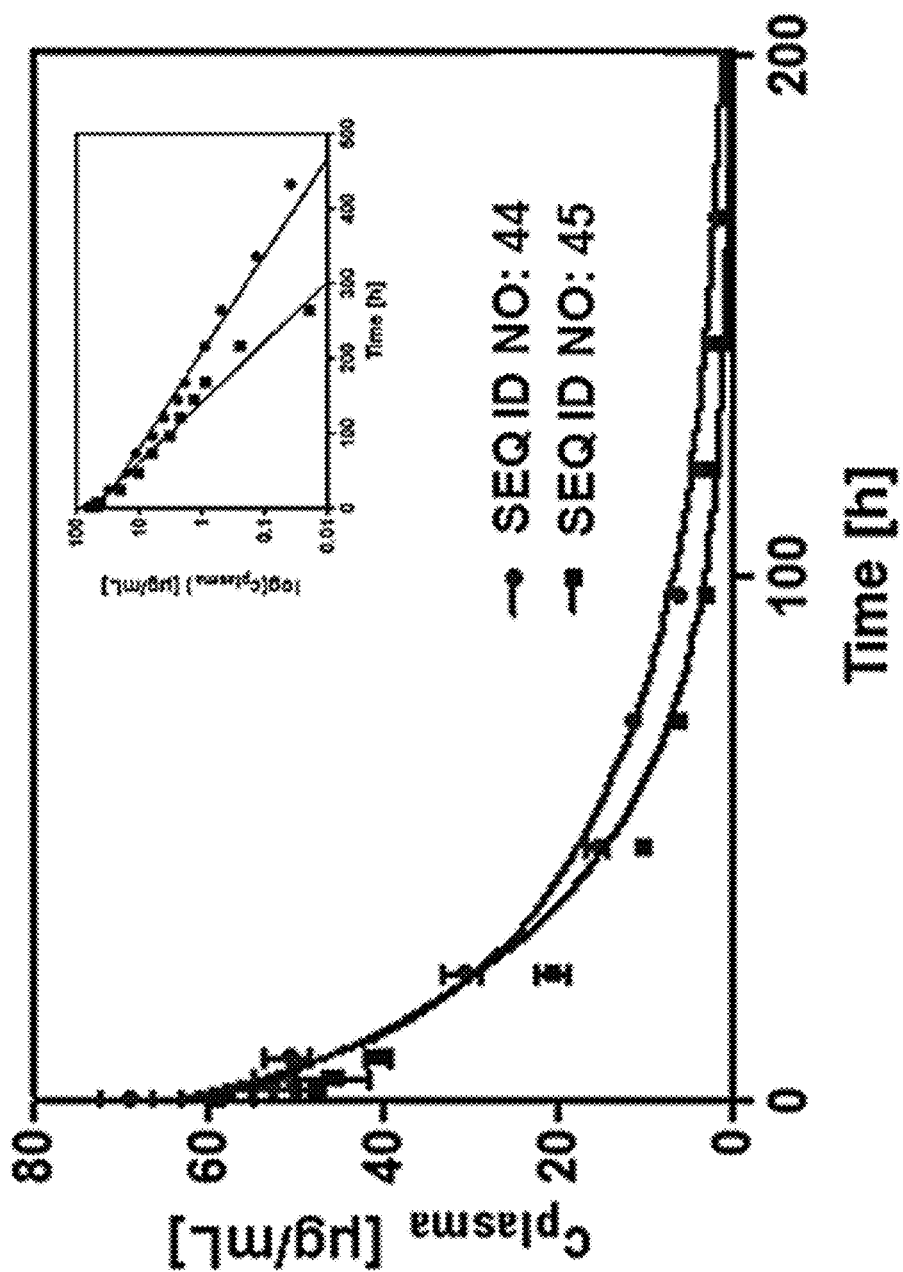

FIG. 26: provides the result of a pharmacokinetic analysis of the bispecific fusion polypeptides SEQ ID NO: 44 and SEQ ID NO: 45 in cynomolgus monkey. Male cynomolgus monkeys received test articles as an intravenous infusion of 60 minutes' duration at a dose of 3 mg/kg. Drug levels were detected using a Sandwich ELISA detecting the full bispecific construct via the targets GPC3 and CD137. The data were fitted using a two-compartmental model.

IV. DETAILED DESCRIPTION OF THE DISCLOSURE

In some embodiments, the fusion polypeptide contains at least two subunits in any order: a first subunit that comprises a full-length immunoglobulin, an antigen-binding domain thereof or a lipocalin mutein specific for GPC3 and a second subunit that comprises a full-length immunoglobulin, an antigen-binding domain thereof or a lipocalin mutein specific for CD137.

In some embodiments, the fusion polypeptide also may contain a third subunit. For instance, the polypeptide may contain a subunit specific for CD137. In some embodiments, said third subunit comprises a lipocalin mutein specific for CD137.

In some embodiments, one subunit can be linked to another subunit as essentially described in FIGS. 1A-D.

For example, one lipocalin mutein can be linked, via a peptide bond, to the C-terminus of the immunoglobulin heavy chain domain (VH), the N-terminus of the VH, the C-terminus of the immunoglobulin light chain (VL), and/or the N-terminus of the VL as depicted in FIG. 1A. In some particular embodiments, a lipocalin mutein subunit can be fused at its N-terminus and/or its C-terminus to an immunoglobulin subunit. For example, the lipocalin mutein may be linked via a peptide bond to the C-terminus of a heavy chain constant region (CH) and/or the C-terminus of a light chain constant region (CL) of the immunoglobulin. In some still further embodiments, the peptide bond may be a linker, particularly an unstructured (G4S)3 linker, for example, as shown in SEQ ID NO: 49.

As another illustrative example, one lipocalin mutein can be linked, via a peptide bond, to the C-terminus or N-terminus of an immunoglobulin-Fc fragment as depicted in FIG. 1B.

As an additional example, one lipocalin mutein can be linked, via a peptide bond, to one or more other lipocalin muteins, as depicted in FIG. 1C.

In this regard, one subunit may be fused at its N-terminus and/or its C-terminus to another subunit. For example, when one subunit comprises a full-length immunoglobulin, another subunit may be linked via a peptide bond to the N-terminus of the second subunit and the C-terminus of a heavy chain constant region (CH) of said immunoglobulin.

In some further embodiments, the third subunit may be linked via a peptide bond to the N-terminus of the third binding domain and the C-terminus of a light chain constant region (CL) of said immunoglobulin. In some still further embodiments, the peptide bond may be a linker, particularly an unstructured (G4S)3 linker, for example, as shown in SEQ ID NO: 49, or may be an unstructured (G4S)2 linker, for example, as shown in SEQ ID NO: 48.

In some embodiments, the third subunit is linked to the first subunit via a peptide bond to the N-terminus of the lipocalin mutein of the third subunit and the C-terminus of a light chain constant region (CL) of the immunoglobulin of the first subunit.

In some embodiments with respect to a fusion polypeptide of the disclosure, one of whose subunits comprises a full-length immunoglobulin, while the polypeptide is simultaneously engaging GPC3 and CD137, the Fc function of the Fc region of the full-length immunoglobulin to Fc receptor-positive cell may be preserved at the same time.

In some other embodiments with respect to a fusion polypeptide of the disclosure, one of whose subunits comprises a full-length immunoglobulin, while the polypeptide is simultaneously engaging GPC3 and CD137, the Fc function of the Fc region of the full-length immunoglobulin, i.e. binding to Fc gamma or FcRn receptor-positive cells, may be reduced or fully suppressed by protein engineering. This may be achieved, for example, by employing a backbone that shows low interaction with Fc-gamma or FcRn receptors such as IgG2 or IgG4. To reduce the residual binding to Fc-gamma receptors, mutations may be introduced into the IgG backbone such as a F234A mutation and/or a L235A mutation. In addition, regarding the IgG4 backbone, a S228P mutation may be introduced to minimize the exchange of IgG4 half-antibody. In some still further embodiments, an additional N297A mutation may be present in the immunoglobulin heavy chain of the fusion polypeptide in order to remove the natural glycosylation motif.

In some embodiments, resulting from the simultaneous binding to GPC3 on tumor cells and CD137 on the surface of effector cells from the immune system, such as T-cells or NK cells, the fusion polypeptides of the disclosure may exhibit GPC3-dependent effector-cell activation, whereby the effector cell of the immune system actively lyses the GPC3-expressing tumor cell.

In some additional embodiments, the fusion polypeptide is capable of demonstrating comparable or superior level of GPC3-dependent CD137 activation as the immunoglobulin included in such fusion polypeptide, for example, when measured in an assay demonstrating target-dependent tumor-infiltrating lymphocyte expansion ex-vivo as essentially described in Chacon, J. A. et al., PloS one 2013 8(4):e60031. In some additional embodiments, the fusion polypeptide is capable of demonstrating comparable or superior level of GPC3-dependent CD137 activation as the immunoglobulin included in such fusion polypeptide, for example, when measured in an in-vivo xenotransplant model of human hepatocellular carcinoma ("HCC"), melanoma, Merkel cell carcinoma, Wilm's tumor, and hepatoblastoma, in analogy to what is essentially described in Kohrt, H. et al, J Clin Invest. 2012 March; 122(3): 1066-75).

In some embodiments, the Fc portion of the immunoglobulin included in a fusion polypeptide of the disclosure may contribute to maintaining the serum levels of the fusion polypeptide, critical for its stability and persistence in the body. For example, when the Fc portion binds to Fc receptors on endothelial cells and on phagocytes, the fusion polypeptide may become internalized and recycled back to the blood stream, enhancing its half-life within body.

In some embodiments, the CD137-specific subunit included in a fusion polypeptide of the disclosure may be a lipocalin mutein that is specific for CD137, such as the lipocalin mutein of SEQ ID NO: 26. In some embodiments, the CD137-specific subunit included in a fusion polypeptide of the disclosure may be a full-length immunoglobulin or an antigen-binding domain thereof that is specific for CD137, such as a monoclonal antibody (e.g. the antibody of SEQ ID NOs: 34 and 35 or the antibody of SEQ ID NO: 51 and 52).

In some embodiments, the GPC3-specific subunit included in a fusion polypeptide of the disclosure may be a lipocalin mutein that is specific for GPC3, such as the lipocalin mutein of SEQ ID NO: 8 or the lipocalin mutein of SEQ ID NO: 10. In some embodiments, the CD137-specific subunit included in a fusion polypeptide of the disclosure may be a full-length immunoglobulin or an antigen-binding domain thereof that is specific for GPC3.

In some embodiments, in a fusion polypeptide of the disclosure, a CD137-specific subunit is fused to a GPC3-specific subunit.

In some more specific embodiments, the GPC3-specific subunit comprises a lipocalin mutein and the CD137-specific subunit comprises a monoclonal antibody.

In some further embodiments, the fusion polypeptide of the disclosure has two GPC3-specific subunits and one CD137-specific subunit. In some more specific embodiments, the GPC3-specific subunits each comprise a lipocalin mutein and the CD137-specific subunits each comprise a monoclonal antibody. In some further embodiments, the two GPC3-specific subunits are identical. In some still further embodiments, the three subunits are fused to each other as structurally depicted in FIG. 1A. In some embodiments, the fusion polypeptide comprises amino acid sequences selected from the group consisting of SEQ ID NOs of 36 and 37, 38 and 39, 40 and 41, or 42 and 43.

In some other specific embodiments, the GPC3-specific subunit comprises a lipocalin mutein and the CD137-specific subunit comprises a lipocalin mutein. In some further embodiments, the two subunits are fused to each other as structurally depicted in FIG. 1C. In some embodiments, the fusion polypeptide comprises amino acid sequence of SEQ ID NO: 46.

In some additional specific embodiments, the fusion polypeptide of the disclosure has two CD137-specific subunits and one GPC3-specific subunit. In some more specific embodiments, the GPC3-specific subunit comprises a lipocalin mutein and the CD137-specific subunits each comprise a lipocalin mutein. In some further embodiments, the two CD137-specific subunits are identical. In some further embodiments, the three subunits are fused to each other as structurally depicted in FIG. 1C. In some embodiments, the fusion polypeptide comprises amino acid sequence of SEQ ID NO: 47.

In some additional embodiments, in a fusion polypeptide of the disclosure, the GPC3-specific subunit comprises a lipocalin mutein and the CD137-specific subunit comprises a lipocalin mutein, and the two subunits are fused to an immunoglobulin-Fc fragment. In some further embodiments, the two subunits are fused to each to the immunoglobulin-Fc fragment as structurally depicted in FIG. 1B. In some particular embodiments, the immunoglobulin-Fc fragment is an IgG4-Fc fragment. In some additional embodiments, the IgG4-Fc fragment is engineered to have a S228P mutation and minimize IgG4 half-antibody exchange in-vitro and in-vivo. In some embodiments, the IgG4-Fc fragment has the amino acid sequence of SEQ ID NO: 73. In some embodiments, the fusion polypeptide comprises amino acid sequence of SEQ ID NO: 44 or of SEQ ID NO: 45.

In some embodiments, the immunoglobulin included in a fusion polypeptide of the disclosure has an IgG2 or IgG4 backbone. In some additional embodiments, the IgG4 backbone has any one of the following mutations selected from the group consisting of S228P, N297A, F234A and L235A. In some additional embodiments, the IgG2 backbone has any one of the following mutations selected from the group consisting of N297A, F234A and L235A.

In some embodiments, the fusion polypeptide may be able to bind CD137 with an EC50 value of at least about 5 nM or even lower, such as about 1 nM or lower, about 0.6 nM or lower, about 0.5 nM or lower, about 0.4 nM or lower, or about 0.3 nM or lower, for example, when the polypeptide is measured in an ELISA assay essentially as described in Example 3, Example 8 or Example 15.

In some embodiments, a fusion polypeptide of the disclosure may be able to bind CD137 with an EC50 value at least as good as or superior to the EC50 value of the lipocalin mutein specific for CD137 as included in such fusion polypeptide, such as the lipocalin mutein of SEQ ID NO: 26, or the antibody specific for CD137 as included in such fusion polypeptide, such as the antibody of SEQ ID NOs: 34 and 35 or the antibody of SEQ ID NOs: 51 and 52, for example, when said lipocalin mutein or antibody and the polypeptide are measured in an ELISA assay essentially as described in Example 8 or Example 15.

In some embodiments, the fusion polypeptide may be able to bind CD137 with an affinity by a $K_D$ of at least about 5 nM or even lower, such as about 1 nM or lower, about 0.6 nM or lower, about 0.5 nM or lower, about 0.3 nM or lower, about 200 pM or lower, about 150 pM or lower, about 100 pM or lower, or about 70 pM or lower, or about 2 pM or lower for example, when measured by Surface plasmon resonance (SPR) analysis as essentially described in Example 6, Example 11, or Example 18.

In another aspect, the fusion polypeptide may be able to bind GPC3 with an EC50 value of at least about 5 nM or even lower, such as about 1 nM or lower, about 0.6 nM or lower, about 0.5 nM or lower, about 0.4 nM or lower, about 0.3 nM or lower, or about 0.2 nM or lower, for example, when the polypeptide is measured in an ELISA assay essentially as described in Example 2, Example 7, Example 12 or Example 14.

In some embodiments, a fusion polypeptide of the disclosure may be able to bind GPC3 with an EC50 value comparable to the EC50 value of the lipocalin mutein specific for GPC3 as included in such fusion polypeptide, such as the lipocalin mutein of SEQ ID NO: 8 or the lipocalin mutein of SEQ ID NO: 10, for example, when said lipocalin mutein and the fusion polypeptide are measured in as ELISA assay essentially as described in Example 7, Example 12 or Example 14.

In some embodiments, the fusion polypeptide may be able to bind GPC3 with an affinity by a $K_D$ of at least about 5 nM or even lower, such as about 1 nM, about 0.3 nM, about 100 pM, about 50 pM or lower, about 20 pM or lower, or about 10 pM or lower, for example, when measured by Surface plasmon resonance (SPR) analysis as essentially described in Example 5, Example 10, or Example 17.

In some embodiments, the fusion polypeptides of the disclosure specific for both CD137 and GPC3 may be capable of simultaneously binding of CD137 and GPC3, for example, when said fusion polypeptide is measured in an ELISA assay essentially described in Example 4, Example 9, Example 13 or Example 16.

In some embodiments, the fusion polypeptides of the disclosure specific for both CD137 and GPC3 may be capable of simultaneously binding of CD137 and GPC3, with an EC50 value of at least about 10 nM or even lower, such as about 8 nM or lower, about 5 nM or lower, about 2.5 nM or lower, about 2 nM or lower, or about 1.5 nM or lower, for example, for example, when said fusion polypeptide is measured in an ELISA assay essentially described in Example 4, Example 9, Example 13 or Example 16.

In some embodiments, the fusion polypeptides of the disclosure specific for both CD137 and GPC3 may be capable of co-stimulating T-cell responses in a functional T-cell activation assay essentially described in Example 19. In some embodiments, the fusion polypeptides of the disclosure may be able to induce IL-2 production in the presence of stimulation of the T-cells in a functional T-cell activation assay essentially described in Example 19 and may even demonstrate a tendency towards stronger IL-2 induction at higher coating concentrations. In some embodiments, the fusion polypeptides of the disclosure do not induce IL-2 production in the absence of anti-CD3 stimulation of the T-cells in a functional T-cell activation assay essentially described in Example 19. In some further embodiments, the fusion polypeptides of the disclosure specific for both CD137 and GPC3 may be capable of co-stimulating the activation of T-cells stimulated with an anti-CD3 and an anti-CD28 antibody at suboptimal concentrations in a functional T-cell activation assay essentially described in Example 19.

In some embodiments, the fusion polypeptides of the disclosure specific for both CD137 and GPC3 may be capable of co-stimulating T-cell responses in a functional T-cell activation assay essentially described in Example 20. In some embodiments, the fusion polypeptides of the disclosure may be able to induce IL-2 production in a functional T-cell activation assay essentially described in Example 20. In some embodiments, the fusion polypeptides of the disclosure may be capable of co-stimulating T-cell activation in a GPC3 target-dependent manner in a functional T-cell activation assay essentially described in Example 20.

A. Exemplary Immunoglobulins as Included in the Fusion Polypeptides.

In some embodiments, with respect to the fusion polypeptide, the first binding domain comprises a full-length immunoglobulin or an antigen-binding domain thereof specific for GPC3 or CD137. The immunoglobulin, for example, may be IgG1, IgG2 or IgG4. In further embodiments, the immunoglobulin is a monoclonal antibody against GPC3 or CD137. An illustrative example of a GPC3-binding immunoglobulin is GC33 (Cancer Sci. 2014 April; 105(4):455-62.). Illustrative examples of CD137-binding antibodies are BMS-663513 (Jure-Kunkel, M. et al., U.S. Pat. No. 7,288,638) and PF-05082566 (Fisher, T. S. et al., Canc Immunol Immunother 2012 October; 61(10):1721-1733).

B. Exemplary GPC3-Specific Lipocalin Muteins as Included in the Fusion Polypeptides.

One aspect of the current disclosure provides a lipocalin mutein that is capable of binding human Glypican-3 (GPC3) with an affinity measured by a KD of about 1 nM or lower. More preferably, the mutein can have an affinity measured by a KD of about 1 nM or 0.2 nM or lower.

In another embodiment, the disclosure relates to a lipocalin mutein, wherein said mutein comprises at one or more positions corresponding to position 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of hNGAL (SEQ ID NO: 2) a substitution, preferably a substitution as described herein.

In particular embodiments, the mutein of the disclosure comprises at least 1, 2, 3, 4, 5, 6, 7, 8, 9, 10, 11, 12, 13, 14, 15, 16, 17, 18, 19 or 20, or even more such as 21, 22, 23, 24, 25 and 26, substitutions at a sequence position corresponding to sequence position 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of mature hNGAL (SEQ ID NO: 2).

In further particular embodiments, a lipocalin mutein according to the current disclosure comprises an amino acid sequence selected from the group consisting of SEQ ID NOs: 4-17. In another embodiment, the mutein has at least 70% identity to the sequence of mature hNGAL (SEQ ID NO: 2). Preferably, said mutein comprises 1, 2, 3, 4, 5, 6, 7, 8, 9, 10, 11, 12, 13, 14, 15, 16, 17, 18, 19 or 20, or even more such as 21, 22, 23, 24, 25 and 26, mutated amino acid residues at the sequence positions 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of mature hNGAL (SEQ ID NO: 2).

In some additional embodiments, in order to facilitate expression in eukaryotic cells, the natural N-glycosylation site Asn at position 65 of the linear polypeptide sequence of mature hNGAL (SEQ ID NO: 2) is removed at the corresponding sequence position of a lipocalin mutein according to the current disclosure, for example, by the mutation from Asn to Asp at position 65. Furthermore, it is preferred that N-glycosylation sites (Asn-X-Ser/Thr) do not exist on a lipocalin mutein according to the current disclosure.

In some other embodiments, a lipocalin mutein according to the current disclosure does not comprise a mutation at the sequence position corresponding to sequence position 28 of the linear polypeptide sequence of mature hNGAL (SEQ ID NO: 2), for example, in order to further optimize stability.

In another embodiment, the mutein of the current disclosure is an antagonist of a GPC3.

As used herein, a lipocalin mutein of the disclosure "specifically binds" a target (here, GPC3) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

Likewise, in another aspect, the disclosure relates to an hNGAL mutein, wherein said mutein comprises at one or more positions corresponding to position 36, 40, 41, 49, 52, 68, 70, 72, 73, 77, 79, 81, 96, 100, 103, 106, 125, 127, 132, and/or 134 of the linear polypeptide sequence of mature hNGAL (SEQ ID NO: 2) a substitution, preferably a substitution as described herein.

In an alternative aspect, present disclosure relates to a polypeptide comprising an hNGAL mutein, wherein the hNGAL mutein comprises at 1, 2, 3, 4, 5, 6, 7, 8, 9, 10, 11, 12, 13, 14, 15, 16, 17, 18, 19, or 20 or even more, such as 21, 22, 23, 24, 25 and 26, amino acid positions corresponding to positions 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of mature hNGAL (SEQ ID NO: 2) a substitution, preferably a substitution as described herein.

Similarly, the disclosure relates to a lipocalin mutein derived from hNGAL having a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin is effective to bind GPC3 as given non-natural target with detectable affinity. Advantageously, the lipocalin mutein comprises at 1, 2, 3, 4, 5, 6, 7, 8, 9, 10, 11, 12, 13, 14, 15, 16, 17, 18, 19 or 20 amino acid position(s) corresponding to the amino acid at position 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of hNGAL (SEQ ID NO: 1) a substitution, preferably a substitution as described herein. The present disclosure also relates to nucleic acids encoding these proteins.

Given the above, a skilled artisan is thus readily in a position to determine which amino acid position mutated in hNGAL as described herein corresponds to an amino acid of a scaffold other than hNGAL. Specifically, a skilled artisan can align the amino acid sequence of a mutein as described herein, in particular an hNGAL mutein of the disclosure with the amino acid sequence of a different mutein to determine which amino acid(s) of said mutein correspond(s) to the respective amino acid(s) of the amino acid sequence of said different lipocalin. More specifically, a skilled artisan can thus determine which amino acid of the amino acid sequence of said different lipocalin corresponds to the amino acid at position(s) 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of hNGAL (SEQ ID NO: 2).

Proteins of present disclosure, which are directed against or specific for GPC3, include any number of specific-binding protein muteins that are based on a defined protein scaffold. As used herein, a "mutein," a "mutated" entity (whether protein or nucleic acid) or "mutant" refers to the exchange, deletion, or insertion of one or more nucleotides or amino acids, respectively, compared to the naturally occurring (wild-type) nucleic acid or protein "reference" scaffold. Preferably, the number of nucleotides or amino acids, respectively, that is exchanged, deleted or inserted is 1, 2, 3, 4, 5, 6, 7, 8, 9, 10, 11, 12, 13, 14, 15, 16, 17, 18, 19, 20 or even more such as 21, 22, 23, 24, 25 and 26. However, it is preferred that a mutein of present disclosure is still capable of binding GPC3.

In some preferred embodiments, a mutein according to the disclosure binds human or mouse GPC3 with a $K_D$ of about 1 nM or less, including 0.5 nM or less, 0.3 nM or less, and or 0.2 nM or less. A mutein of the disclosure may specifically bind one or more continuous, discontinuous or conformation epitope(s) of the mature, folded bioactive form of GPC3.

The binding affinity of a protein of present disclosure (e.g. a mutein of a lipocalin) to a selected target (in the present case, GPC3), can be measured (and thereby $K_D$ values of a mutein-ligand complex be determined) by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Such methods are well established in the art and examples thereof are also detailed below.

The amino acid sequence of a mutein of the disclosure may have a high sequence identity to mature human Lipocalin 2. In this context, a protein of present disclosure may have at least 70%, at least 75%, at least 80%, at least 82%, at least 85%, at least 87%, at least 90% identity, including at least 95% identity to a protein selected from the group consisting of the sequence of SEQ ID NO: 2 such a mutein of an amino acid sequence selected from the group consisting of SEQ ID NOs: 4-17.

The disclosure also includes structural homologues of the proteins selected from the group consisting of the sequence of SEQ ID NOs: 4-17, which have an amino acid sequence homology or sequence identity of more than about 60%, preferably more than 65%, more than 70%, more than 75%, more than 80%, more than 85%, more than 90%, more than 92% and most preferably more than 95% in relation thereto.

In line with the above, a mutein of the disclosure preferably acts as an antagonist of GPC3. In some embodiments, a mutein of the disclosure may act as an antagonist of GPC3 by inhibiting the ability of the GPC3 molecule to bind to or otherwise interact with its cognate ligand.

In yet another aspect, the present disclosure includes muteins of human Lipocalin 2 that specifically bind GPC3. In this sense, GPC3 can be regarded a non-natural ligand of wild type human Lipocalin 2, where "non-natural ligand" refers to a compound that does not bind to human Lipocalin 2 under physiological conditions. By engineering wild type lipocalins such as human Lipocalin 2 with mutations at certain positions, the present inventors have demonstrated that high affinity and high specificity for a non-natural ligand is possible. In one aspect at least at 1, 2, 3, 4, 5, 6, 7, 8, 9, 10, 11, 12, 13, 14, 15, 16, 17, 18, 19, and/or 20 nucleotide triplet(s) encoding for any of the sequence positions 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of a mature human Lipocalin 2 (SEQ ID NO: 2), a random mutagenesis can be carried out by allowing substitution at these positions by a subset of nucleotide triplets.

Further, the lipocalins can be used to generate muteins that have a mutated amino acid residue at any one or more, including at least at any two, three, four, five, six, seven, eight, nine, ten, eleven, twelve, thirteen, fourteen, fifteen, sixteen, seventeen, eighteen, nineteen or twenty, of the sequence positions of the sequence positions corresponding to the sequence positions 36, 40, 41, 49, 52, 65, 68, 70, 72, 73, 77, 79, 81, 87, 96, 100, 103, 105, 106, 125, 127, 132, 134, 136 and/or 175 of the linear polypeptide sequence of a mature human Lipocalin 2 (SEQ ID NO: 2).

A substitution at sequence position 36 may for example be a substitution Leu 36→Val or Arg. A substitution at sequence position 40 may for example be a substitution Ala 40→Leu, Val or Gly. A substitution at sequence position 41 may for example be a substitution Ile 41→Leu, Arg, Met, Gly or Ala. A substitution at sequence position 49 may for example be a substitution Gln 49→Pro or Leu. A substitution at sequence position 52 may for example be a substitution Tyr 52→Arg or Trp. A substitution at sequence position 68 may for example be a substitution Asn 65→Asp. A substitution at sequence position 68 may for example be a substitution Ser 68→Val, Gly, Asn or Ala. A substitution at sequence position 70 may for example be a substitution Leu 70→Arg, Ser, Ala or Val. A substitution at sequence position 72 may for example be a substitution Arg 72→Asp, Trp, Ala, or Gly. A substitution at sequence position 73 may for example be a substitution Lys 73→Gly, Arg, Asn, Glu or Ser. A substitution at sequence position 76 may for example be a substitution Cys 76→Val or Ile. A substitution at sequence position 77 may for example be a substitution Asp 77→His, Met, Val, Leu, Thr or Lys. A substitution at sequence position 79 may for example be a substitution Trp 79→Lys, Ser or Thr. A substitution at sequence position 81 may for example be a substitution Arg 81→Gly. A substitution at sequence position 81 may for example be a substitution Cys 87→Ser. A substitution at sequence position 96 may for example be a substitution Asn 96→Arg, Asp, Gln or Pro. A substitution at sequence position 100 may for example be a substitution Tyr 100→Gly, Glu, Pro or Gln. A substitution at sequence position 103 may for example be a substitution Leu 103→Glu, Gln, Asn, Gly, Ser or Tyr. A substitution at sequence position 106 may for example be a substitution Ser 105→Ala. A substitution at sequence position 106 may for example be a substitution Tyr 106→Asn, Ser or Thr. A substitution at sequence position 125 may for example be a substitution Lys 125→Glu. A substitution at sequence position 127 may for example be a substitution Ser 127→Arg or Tyr. A substitution at sequence position 132 may for example be a substitution Tyr 132→Trp or Ile. A substitution at sequence position 134 may for example be a substitution Lys 134 f Ala or Phe. A substitution at sequence position 134 may for example be a substitution Thr 136 f Ile. A substitution at sequence position 175 may for example be a substitution Cys 175 f Ala. Noteworthy, any of the amino acids that substitute the corresponding amino acid in the reference sequence can be exchanged by a corresponding conservative amino acid. In particular, conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

In one embodiment, a mutein of present disclosure, which binds to GPC3 includes the following amino acid replacements:

(a) Leu 36→Val; Ile 41→Leu; Gln 49→Leu; Tyr 52→Arg; Asn 65→Asp; Ser 68→Val; Leu 70→Ser; Arg 72→Trp; Lys 73→Arg; Asp 77→His; Trp 79→Lys; Arg 81→Gly; Cys 87→Ser; Asn 96→Asp; Tyr 100→Gly; Leu 103→Gln; Tyr 106→Asn; Lys 125→Glu; Ser 127→Arg; Tyr 132→Trp; Lys 134→Ala;

(b) Leu 36→Val; Ala 40→Val; Ile 41→Arg; Gln 49→Pro; Tyr 52→Arg; Asn 65→Asp; Ser 68→Gly; Leu 70→Ser; Lys 73→Gly; Asp 77→His; Trp 79→Lys; Arg 81→Gly; Cys 87→Ser; Asn 96→Asp; Tyr 100→Gly; Leu 103→Glu; Tyr 106→Asn; Lys 125→Glu; Ser 127→Arg; Tyr 132→Trp; Lys 134→Phe;

(c) Leu 36→Val; Ala 40→Gly; Ile 41→Met; Gln 49→Leu; Tyr 52→Arg; Asn 65→Asp; Leu 70→Ala; Lys 73→Asn; Asp 77→His; Trp 79→Lys; Arg 81→Gly; Cys 87→Ser; Asn 96→Gln; Tyr 100→Gly; Leu 103→Glu; Tyr 106→Asn; Lys 125→Glu; Ser 127→Arg; Tyr 132→Trp; Lys 134→Phe;

(d) Leu 36→Arg; Ala 40→Val; Ile 41→Gly; Gln 49→Pro; Tyr 52→Trp; Asn 65→Asp; Ser 68→Asn; Leu 70→Arg; Arg 72→Ala; Lys 73→Arg; Asp 77→Leu; Trp 79→Ser; Arg 81→Gly; Cys 87→Ser; Asn 96→Gln; Tyr 100→Glu; Leu 103→Asn; Ser 105→Ala; Tyr 106→Asn; Lys 125→Glu; Ser 127→Tyr; Tyr 132→Ile; Lys 134→Phe; Thr 136→Ile;

(e) Leu 36→Arg; Ala 40→Val; Ile 41→Gly; Gln 49→Pro; Tyr 52→Trp; Asn 65→Asp; Ser 68→Asn; Leu 70→Arg; Arg 72→Ala; Lys 73→Arg; Asp 77→Thr; Trp 79→Ser; Arg 81→Gly; Cys 87→Ser; Asn 96→Gln; Tyr 100→Glu; Leu 103→Gly; Ser 105→Ala; Tyr 106→Asn; Lys 125→Glu; Ser 127→Tyr; Tyr 132→Ile; Lys 134→Phe; Thr 136→Ile;

(f) Leu 36→Arg; Ala 40→Gly; Ile 41→Ala; Gln 49→Pro; Tyr 52→Trp; Asn 65→Asp; Ser 68→Asn; Leu 70→Arg; Arg 72→Ala; Lys 73→Arg; Asp 77→Val; Trp 79→Ser; Arg 81→Gly; Cys 87→Ser; Asn 96→Pro; Tyr 100→Glu; Leu

103→Asn; Ser 105→Ala; Tyr 106→Ser; Lys 125→Glu; Ser 127→Tyr; Tyr 132→Ile; Lys 134→Phe; Thr 136→Ile;
(g) Leu 36→Arg; Ala 40→Val; Ile 41→Ala; Gln 49→Pro; Tyr 52→Arg; Asn 65→Asp; Ser 68→Ala; Leu 70→Arg; Arg 72→Ala; Lys 73→Arg; Asp 77→Leu; Trp 79→Ser; Arg 81→Gly; Cys 87→Ser; Asn 96→Arg; Tyr 100→Glu; Leu 103→Tyr; Ser 105→Ala; Tyr 106→Asn; Lys 125→Glu; Ser 127→Tyr; Tyr 132→Ile; Lys 134→Phe; Thr 136→Ile;
(h) Leu 36→Arg; Ala 40→Val; Ile 41→Ala; Gln 49→Pro; Tyr 52→Arg; Asn 65→Asp; Ser 68→Asn; Leu 70→Val; Arg 72→Ala; Lys 73→Gly; Asp 77→Lys; Trp 79→Ser; Arg 81→Gly; Cys 87→Ser; Asn 96→Arg; Tyr 100→Pro; Leu 103→Asn; Ser 105→Ala; Tyr 106→Asn; Lys 125→Glu; Ser 127→Tyr; Tyr 132→Ile; Lys 134→Phe; Thr 136→Ile;
(i) Leu 36→Arg; Ala 40→Leu; Ile 41→Gly; Gln 49→Pro; Tyr 52→Trp; Asn 65→Asp; Ser 68→Asn; Leu 70→Arg; Arg 72→Ala; Lys 73→Arg; Asp 77→Met; Trp 79→Ser; Arg 81→Gly; Cys 87→Ser; Asn 96→Gln; Tyr 100→Glu; Leu 103→Ser; Ser 105→Ala; Tyr 106→Asn; Lys 125→Glu; Ser 127→Tyr; Tyr 132→Ile; Lys 134→Phe;
(j) Leu 36→Arg; Ala 40→Val; Ile 41→Gly; Gln 49→Pro; Tyr 52→Trp; Asn 65→Asp; Ser 68→Asn; Leu 70→Arg; Arg 72→Ala; Lys 73→Gly; Cys 76→Val; Asp 77→Lys; Trp 79→Thr; Arg 81→Gly; Cys 87→Ser; Asn 96→Gln; Tyr 100→Glu; Leu 103→Asn; Ser 105→Ala; Tyr 106→Thr; Lys 125→Glu; Ser 127→Tyr; Tyr 132→Ile; Lys 134→Phe; Cys 175→Ala;
(k) Leu 36→Arg; Ala 40→Val; Ile 41→Gly; Gln 49→Pro; Tyr 52→Arg; Asn 65→Asp; Ser 68→Gly; Leu 70→Arg; Arg 72→Gly; Lys 73→Glu; Cys 76→Ile; Asp 77→Lys; Trp 79→Ser; Arg 81→Gly; Cys 87→Ser; Asn 96→Gln; Tyr 100→Gln; Leu 103→Asp; Ser 105→Ala; Tyr 106→Thr; Lys 125→Glu; Ser 127→Tyr; Tyr 132→Ile; Lys 134→Phe; Thr 136→Ile; Cys 175→Ala; or
(l) Leu 36→Arg; Ala 40→Val; Ile 41→Gly; Gln 49→Pro; Tyr 52→Arg; Asn 65→Asp; Ser 68→Gly; Leu 70→Arg; Arg 72→Asp; Lys 73→Ser; Cys 76→Val; Asp 77→Thr; Trp 79→Ser; Arg 81→Gly; Cys 87→Ser; Asn 96→Gln; Tyr 100→Glu; Leu 103→Asn; Ser 105→Ala; Tyr 106→Thr; Lys 125→Glu; Ser 127→Tyr; Tyr 132→Ile; Lys 134→Phe; Thr 136→Ile; Cys 175→Ala.

The numbering is preferably in relation to the linear polypeptide sequence of mature hNGAL (SEQ ID NO: 2). Accordingly, given the teaching of the disclosure, a skilled artisan can readily determine which amino acids in the preferred reference sequence of mature hNGAL (SEQ ID NO: 2) correspond to those described above in (a) to (l); so as to mutate said amino acids in the reference sequence.

C. Exemplary CD137-Specific Lipocalin Muteins as Included in the Fusion Polypeptides.

In one aspect, the present disclosure provides human lipocalin muteins that bind CD137 and useful applications therefor. The disclosure also provides methods of making CD137 binding proteins described herein as well as compositions comprising such proteins. CD137 binding proteins of the disclosure as well as compositions thereof may be used in methods of detecting CD137 in a sample or in methods of binding of CD137 in a subject. No such human lipocalin muteins having these features attendant to the uses provided by present disclosure have been previously described.

Another embodiment of the current disclosure provides a lipocalin mutein that is capable of activating downstream signaling pathways of CD137 by binding to CD137.

In one embodiment, the present disclosure provides CD137-binding human tear lipocalin muteins.

In this regard, the disclosure provides one or more Tlc muteins that are capable of binding CD137 with an affinity measured by a KD of about 300 nM or lower and even about 100 nM or lower.

In some embodiments, such Tlc mutein comprises a mutated amino acid residue at one or more positions corresponding to positions 5, 26-31, 33-34, 42, 46, 52, 56, 58, 60-61, 65, 71, 85, 94, 101, 104-106, 108, 111, 114, 121, 133, 148, 150 and 153 of the linear polypeptide sequence of the mature human tear lipocalin (SEQ ID NO: 1).

In some particular embodiments, such Tlc mutein may contain a mutated amino acid residue at one or more positions corresponding to positions 26-34, 55-58, 60-61, 65, 104-106 and 108 of the linear polypeptide sequence of the mature human tear lipocalin.

In further particular embodiments, such Tlc mutein may further include a mutated amino acid residue at one or more positions corresponding to positions 101, 111, 114 and 153 of the linear polypeptide sequence of the mature human tear lipocalin.

In other particular embodiments, the Tlc may contain a mutated amino acid residue at one or more positions corresponding to positions 5, 26-31, 33-34, 42, 46, 52, 56, 58, 60-61, 65, 71, 85, 94, 101, 104-106, 108, 111, 114, 121, 133, 148, 150 and 153 of the linear polypeptide sequence of the mature human tear lipocalin.

In some further embodiments, the Tlc mutein may comprise at least 1, 2, 3, 4, 5, 6, 7, 8, 9, 10, 11, 12, 13, 14, 15, 16, 17, 18, 19, 20, 21, 22, 23, 24, 25, 26 or even more, mutated amino acid residues at one or more sequence positions corresponding to sequence positions 5, 26-31, 33-34, 42, 46, 52, 56, 58, 60-61, 65, 71, 85, 94, 101, 104-106, 108, 111, 114, 121, 133, 148, 150 and 153 of the linear polypeptide sequence of the mature human tear lipocalin and wherein said polypeptide binds CD137, in particular human CD137.

In some still further embodiments, the disclosure relates to a polypeptide, wherein said polypeptide is a Tlc mutein, in comparison with the linear polypeptide sequence of the mature human tear lipocalin, comprising at least 1, 2, 3, 4, 5, 6, 7, 8, 9, 10, 11, 12 or even more, mutated amino acid residues at the sequence positions 526-34, 55-58, 60-61, 65, 104-106 and 108 and wherein said polypeptide binds CD137, in particular human CD137.

In some embodiments, a lipocalin mutein according to the disclosure may include at least one amino acid substitution of a native cysteine residue by e.g. a serine residue. In some embodiments, a Tlc mutein according to the disclosure includes an amino acid substitution of a native cysteine residue at positions 61 and/or 153 by another amino acid such as a serine residue. In this context it is noted that it has been found that removal of the structural disulfide bond (on the level of a respective nave nucleic acid library) of wild-type tear lipocalin that is formed by the cysteine residues 61 and 153 (cf. Breustedt, et al., 2005, supra) may provide tear lipocalin muteins that are not only stably folded but are also able to bind a given non-natural ligand with high affinity. In some particular embodiments, the Tlc mutein according to the disclosure includes the amino acid substitutions Cys 61→Ala, Phe, Lys, Arg, Thr, Asn, Gly, Gln, Asp, Asn, Leu, Tyr, Met, Ser, Pro or Trp and Cys 153→Ser or Ala. Such a substitution has proven useful to prevent the formation of the naturally occurring disulphide bridge linking Cys 61 and Cys 153, and thus to facilitate handling of the mutein. However, tear lipocalin muteins that binds CD137 and that have the disulphide bridge formed between Cys 61 and Cys 153 are also part of the present disclosure.

In some embodiments, the elimination of the structural disulde bond may provide the further advantage of allowing for the (spontaneous) generation or deliberate introduction of non-natural artificial disulfide bonds into muteins of the disclosure, thereby increasing the stability of the muteins. For example, in some embodiments, either two or all three of the cysteine codons at position 61, 101 and 153 are replaced by a codon of another amino acid. Further, in some embodiments, a Tlc mutein according to the disclosure includes an amino acid substitution of a native cysteine residue at position 101 by a serine residue or a histidine residue.

In some embodiments, a mutein according to the disclosure includes an amino acid substitution of a native amino acid by a cysteine residue at positions 28 or 105 with respect to the amino acid sequence of mature human tear lipocalin.

Further, in some embodiments, a mutein according to the disclosure includes an amino acid substitution of a native arginine residue at positions 111 by a proline residue. Further, in some embodiments, a mutein according to the disclosure includes an amino acid substitution of a native lysine residue at positions 114 by a tryptophan residue or a glutamic acid.

In some embodiments, a CD137-binding Tlc mutein according to the disclosure includes, at one or more positions corresponding to positions 5, 26-31, 33-34, 42, 46, 52, 56, 58, 60-61, 65, 71, 85, 94, 101, 104-106, 108, 111, 114, 121, 133, 148, 150 and 153 of the linear polypeptide sequence of the mature human tear lipocalin (SEQ ID NO: 1), one or more of the following mutated amino acid residues: Ala 5→Val or Thr; Arg 26→Glu; Glu 27→Gly; Phe 28→Cys; Pro 29→Arg; Glu 30→Pro; Met 31→Trp; Leu 33→Ile; Glu 34→Phe; Thr 42→Ser; Gly 46→Asp; Lys 52→Glu; Leu 56→Ala; Ser 58→Asp; Arg 60→Pro; Cys 61→Ala; Lys 65→Arg or Asn; Thr 71→Ala; Val 85→Asp; Lys 94→Arg or Glu; Cys 101→Ser; Glu 104→Val; Leu 105→Cys; His 106→Asp; Lys 108→Ser; Arg 111→Pro; Lys 114→Trp; Lys 121→Glu; Ala 133→Thr; Arg 148→Ser; Ser 150→Ile and Cys 153→Ser. In some embodiments, a Tlc mutein according to the disclosure includes two or more, such as 3, 4, 5, 6, 7, 8, 9, 10, 11, 12, even more such as 13, 14, 15, 16, 17, 18, 19, 20, 21, 22, 23, 24, 25, 26 or all mutated amino acid residues at these sequence positions of the mature human tear lipocalin.

In some additional embodiments, the Tlc mutein binding CD137 includes one of the following sets of amino acid substitutions in comparison with the linear polypeptide sequence of the mature human tear lipocalin:

1. Arg 26→Glu; Glu 27→Gly; Phe 28→Cys; Pro 29→Arg; Glu 30→Pro; Met 31→Trp; Leu 33→Ile; Glu 34→Phe; Leu 56→Ala; Ser 58→Asp; Arg 60→Pro; Cys 61→Ala; Cys 101→Ser; Glu 104→Val; Leu 105→Cys; His 106→Asp; Lys 108→Ser; Arg 111→Pro; Lys 114→Trp; Cys 153→Ser;

2. Ala 5→Thr; Arg 26→Glu; Glu 27→Gly; Phe 28→Cys; Pro 29→Arg; Glu 30→Pro; Met 31→Trp; Leu 33→Ile; Glu 34→Phe; Leu 56→Ala; Ser 58→Asp; Arg 60→Pro; Cys 61→Ala; Lys 65→Arg; Val 85→Asp; Cys 101→Ser; Glu 104→Val; Leu 105→Cys; His 106→Asp; Lys 108→Ser; Arg 111→Pro; Lys 114→Trp; Lys 121→Glu; Ala 133 Thr; Cys 153→Ser; 157→Pro;

3. Arg 26→Glu; Glu 27→Gly; Phe 28→Cys; Pro 29→Arg; Glu 30→Pro; Met 31→Trp; Leu 33→Ile; Glu 34→Phe; Leu 56→Ala; Ser 58→Asp; Arg 60→Pro; Cys 61→Ala; Lys 65→Asn; Lys 94→Glu; Cys 101→Ser; Glu 104→Val; Leu 105→Cys; His 106→Asp; Lys 108→Ser; Arg 111→Pro; Lys 114→Trp; Lys 121→Glu; Ala 133→Thr; Cys 153→Ser;

4. Ala 5→Val; Arg 26→Glu; Glu 27→Gly; Phe 28→Cys; Pro 29→Arg; Glu 30→Pro; Met 31→Trp; Leu 33→Ile; Glu 34→Phe; Leu 56→Ala; Ser 58→Asp; Arg 60→Pro; Cys 61→Ala; Lys 65→Arg; Lys 94→Glu; Cys 101→Ser; Glu 104→Val; Leu 105→Cys; His 106→Asp; Lys 108→Ser; Arg 111→Pro; Lys 114→Trp; Lys 121→Glu; Ala 133→Thr; Cys 153→Ser; 157→Pro;

5. Arg 26→Glu; Glu 27→Gly; Phe 28→Cys; Pro 29→Arg; Glu 30→Pro; Met 31→Trp; Leu 33→Ile; Glu 34→Phe; Thr 42→Ser; Leu 56→Ala; Ser 58→Asp; Arg 60→Pro; Cys 61→Ala; Cys 101→Ser; Glu 104→Val; Leu 105→Cys; His 106→Asp; Lys 108→Ser; Arg 111→Pro; Lys 114→Trp; Ser 150→Ile; Cys 153→Ser; 157→Pro;

6. Arg 26→Glu; Glu 27→Gly; Phe 28→Cys; Pro 29→Arg; Glu 30→Pro; Met 31→Trp; Leu 33→Ile; Glu 34→Phe; Lys 52→Glu; Leu 56→Ala; Ser 58→Asp; Arg 60→Pro; Cys 61→Ala; Thr 71→Ala; Cys 101→Ser; Glu 104→Val; Leu 105→Cys; His 106→Asp; Lys 108→Ser; Arg 111→Pro; Lys 114→Trp; Ala 133→Thr; Arg 148→Ser; Ser 150→Ile; Cys 153→Ser; 157→Pro; or 7. Ala 5→Thr; Arg 26→Glu; Glu 27→Gly; Phe 28→Cys; Pro 29→Arg; Glu 30→Pro; Met 31→Trp; Leu 33→Ile; Glu 34→Phe; Gly 46→Asp; Leu 56→Ala; Ser 58→Asp; Arg 60→Pro; Cys 61→Ala; Thr 71→Ala; Cys 101→Ser; Glu 104→Val; Leu 105→Cys; His 106→Asp; Lys 108→Ser; Arg 111→Pro; Lys 114→Trp; Ser 150→Ile; Cys 153→Ser; 157→Pro.

In the residual region, i.e. the region differing from sequence positions 5, 26-31, 33-34, 42, 46, 52, 56, 58, 60-61, 65, 71, 85, 94, 101, 104-106, 108, 111, 114, 121, 133, 148, 150 and 153, a Tlc mutein of the disclosure may include the wild-type (natural) amino acid sequence outside the mutated amino acid sequence positions.

In still further embodiments, a Tlc mutein according to the current disclosure has at least 70% sequence identity or at least 70% sequence homology to the sequence of the mature human tear lipocalin (SEQ ID NO: 1).

A Tlc mutein according to the present disclosure can be obtained by means of mutagenesis of a naturally occurring form of human tear lipocalin. In some embodiments of the mutagenesis, a substitution (or replacement) is a conservative substitution. Nevertheless, any substitution—including non-conservative substitution or one or more from the exemplary substitutions below—is envisaged as long as the lipocalin mutein retains its capability to bind to CD137, and/or it has a sequence identity to the then substituted sequence in that it is at least 60%, such as at least 65%, at least 70%, at least 75%, at least 80%, at least 85% or higher sequence identity to the amino acid sequence of the mature human tear lipocalin (SWISS-PROT Data Bank Accession Number P31025).

In another aspect, the present disclosure relates to novel, specific-binding hNGAL muteins directed against or specific for CD137.

In this regard, the disclosure provides one or more hNGAL muteins that are capable of binding CD137 with an affinity measured by a KD of 200 nM or lower, about 140 nM or lower, about 50 nM or lower, and even about 10 nM or lower. More preferably, the hNGAL muteins can have an affinity measured by a KD of about 5 nM or lower.

In some embodiments, an hNGAL mutein of the disclosure includes at one or more positions corresponding to positions 28, 36, 40-41, 49, 52, 65, 68, 70, 72-73, 77, 79, 81, 83, 87, 94, 96, 100, 103, 106, 125, 127, 132 and 134 of the linear polypeptide sequence of the mature hNGAL (SEQ ID NO: 2) a substitution.

In particular embodiments, a lipocalin mutein of the disclosure comprises at least 1, 2, 3, 4, 5, 6, 7, 8, 9, 10, 11, 12, 13, 14, 15, 16, 17, 18, 19, 20, 21, or even more, substitution(s) at a sequence position corresponding to sequence position 28, 36, 40-41, 49, 52, 65, 68, 70, 72-73, 77, 79, 81, 83, 87, 94, 96, 100, 103, 106, 125, 127, 132 and 134 of the linear polypeptide sequence of the mature hNGAL (SWISS-PROT Data Bank Accession Number P80188; SEQ ID NO: 2). Preferably, it is envisaged that the disclosure relates to a lipocalin mutein which comprises, in addition to one or more substitutions at positions corresponding to positions 36, 87 and/or 96 of the linear polypeptide sequence of the mature human NGAL, at one or more positions corresponding to positions 28, 40-41, 49, 52, 65, 68, 70, 72-73, 77, 79, 81, 83, 94, 100, 103, 106, 125, 127, 132 and 134 of the linear polypeptide sequence of the mature hNGAL a substitution.

In some still further embodiments, the disclosure relates to a polypeptide, wherein said polypeptide is an hNGAL mutein, in comparison with the linear polypeptide sequence of the mature hNGAL (SWISS-PROT Data Bank Accession Number P80188; SEQ ID NO: 2), comprising at least 1, 2, 3, 4, 5, 6, 7, 8, 9, 10, 11, 12, 13, 14, 15, 16, 17, 18, 19, 20, 21, or even more, mutated amino acid residues at the sequence positions 28, 36, 40-41, 49, 52, 65, 68, 70, 72-73, 77, 79, 81, 87, 96, 100, 103, 106, 125, 127, 132 and 134, and wherein said polypeptide binds CD137, in particular human CD137.

In some embodiments, a CD137-binding hNGAL mutein of the disclosure includes, at any one or more of the sequence positions 28, 36, 40-41, 49, 52, 65, 68, 70, 72-73, 77, 79, 81, 83, 87, 94, 96, 100, 103, 106, 125, 127, 132 and 134 of the linear polypeptide sequence of the mature hNGAL (SEQ ID NO: 2), one or more of the following mutated amino acid residues: Gln 28→His; Leu 36→Gln; Ala 40→Ile; Ile 41→Arg or Lys; Gln 49→Val, Ile, His, Ser or Asn; Tyr 52→Met; Asn 65→Asp; Ser 68→Met, Ala or Gly; Leu 70→Ala, Lys, Ser or Thr; Arg 72→Asp; Lys 73→Asp; Asp 77→Met, Arg, Thr or Asn; Trp 79→Ala or Asp; Arg 81→Met, Trp or Ser; Phe 83→Leu; Cys 87→Ser; Leu 94→Phe; Asn 96→Lys; Tyr 100→Phe; Leu 103→His; Tyr 106→Ser; Lys 125→Phe; Ser 127→Phe; Tyr 132→Glu and Lys 134→Tyr.

In some embodiments, an hNGAL mutein of the disclosure includes two or more, such as 3, 4, 5, 6, 7, 8, 9, 10, 11, 12, even more such as 13, 14, 15, 16, 17, 18, 19, 20, 21, 22, 23, 24 or all mutated amino acid residues at these sequence positions of the mature hNGAL.

In some additional embodiments, an hNGAL mutein of the disclosure, which binds to CD137 includes the following amino acid replacements in comparison with the linear polypeptide sequence of the mature hNGAL:
  (a) Gln 28→His; Leu 36→Gln; Ala 40→Ile; Ile 41→Lys; Gln 49→Asn; Tyr 52→Met; Ser 68→Gly; Leu 70→Thr; Arg 72→Asp; Lys 73→Asp; Asp 77→Thr; Trp 79→Ala; Arg 81→Ser; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;
  (b) Gln 28→His; Leu 36→Gln; Ala 40→Ile; Ile 41→Arg; Gln 49→Ile; Tyr 52→Met; Asn 65→Asp; Ser 68→Met; Leu 70→Lys; Arg 72→Asp; Lys 73→Asp; Asp 77→Met; Trp 79→Asp; Arg 81→Trp; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;
  (c) Gln 28→His; Leu 36→Gln; Ala 40→Ile; Ile 41→Arg; Gln 49→Asn; Tyr 52→Met; Asn 65→Asp; Ser 68→Ala; Leu 70→Ala; Arg 72→Asp; Lys 73→Asp; Asp 77→Thr; Trp 79→Asp; Arg 81→Trp; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;
  (d) Gln 28→His; Leu 36→Gln; Ala 40→Ile; Ile 41→Lys; Gln 49→Asn; Tyr 52→Met; Asn 65→Asp; Ser 68→Ala; Leu 70→Ala; Arg 72→Asp; Lys 73→Asp; Asp 77→Thr; Trp 79→Asp; Arg 81→Trp; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;
  (e) Gln 28→His; Leu 36→Gln; Ala 40→Ile; Ile 41→Lys; Gln 49→Ser; Tyr 52→Met; Asn 65→Asp; Ser 68→Gly; Leu 70→Ser; Arg 72→Asp; Lys 73→Asp; Asp 77→Thr; Trp 79→Ala; Arg 81→Met; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;
  (f) Gln 28→His; Leu 36→Gln; Ala 40→Ile; Ile 41→Lys; Gln 49→Val; Tyr 52→Met; Asn 65→Asp; Ser 68→Gly; Leu 70→Thr; Arg 72→Asp; Lys 73→Asp; Asp 77→Arg; Trp 79→Asp; Arg 81→Ser; Cys 87→Ser; Leu 94→Phe; Asn 96→Lys; Tyr 100→Phe; Leu 103→His; Tyr 106→Ser; Lys 125→Phe; Ser 127→Phe; Tyr 132 Glu; Lys 134→Tyr;
  (g) Gln 28→His; Leu 36→Gln; Ala 40→Ile; Ile 41→Arg; Gln 49→His; Tyr 52→Met; Asn 65→Asp; Ser 68→Gly; Leu 70→Thr; Arg 72→Asp; Lys 73→Asp; Asp 77→Thr; Trp 79→Ala; Arg 81→Ser; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;
  (h) Gln 28→His; Leu 36→Gln; Ala 40→Ile; Ile 41→Lys; Gln 49→Asn; Tyr 52→Met; Asn 65→Asp; Ser 68→Gly; Leu 70→Thr; Arg 72→Asp; Lys 73→Asp; Asp 77→Thr; Trp 79→Ala; Arg 81→Ser; Phe 83→Leu; Cys 87→Ser; Leu 94→Phe; Asn 96→Lys; Tyr 100→Phe; Leu 103→His; Tyr 106→Ser; Lys 125→Phe; Ser 127→Phe; Tyr 132→Glu; Lys 134→Tyr; or
  (i) Gln 28→His; Leu 36→Gln; Ala 40→Ile; Ile 41→Arg; Gln 49→Ser; Tyr 52→Met; Asn 65→Asp; Ser 68→Ala; Leu 70→Thr; Arg 72→Asp; Lys 73→Asp; Asp 77→Asn; Trp 79→Ala; Arg 81→Ser; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr.

In the residual region, i.e. the region differing from sequence positions 28, 36, 40-41, 49, 52, 65, 68, 70, 72-73, 77, 79, 81, 83, 87, 94, 96, 100, 103, 106, 125, 127, 132 and 134, an hNGAL mutein of the disclosure may include the wild-type (natural) amino acid sequence outside the mutated amino acid sequence positions.

In another embodiment, the hNGAL mutein has at least 70% or even higher sequence identity to the amino acid sequence of the mature human lipocalin 2 (SWISS-PROT Data Bank Accession Number P80188).

In further particular embodiments, a CD137-binding lipocalin mutein according to the current disclosure comprises an amino acid sequence selected from the group consisting of SEQ ID NOs: 18-33 or a fragment or variant thereof.

The amino acid sequence of a CD137-binding lipocalin mutein of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 18-33.

The disclosure also includes structural homologues of a lipocalin mutein having an amino acid sequence selected from the group consisting of SEQ ID NOs: 18-33, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said mutein.

D. Exemplary Uses, Applications and Production of the Fusion Polypeptides.

In some embodiments, fusion polypeptides of the disclosure may produce synergistic effect through dual-targeting of CD137 and GPC3.

Numerous possible applications for the fusion polypeptides of the disclosure, therefore, exist in medicine.

In one aspect, the disclosure relates to the use of the fusion polypeptides disclosed herein for detecting CD137 and GPC3 in a sample as well as a respective method of diagnosis.

In another aspect, the disclosure features the use of one or more fusion polypeptides disclosed herein or of one or more compositions comprising such polypeptides for simultaneously binding of CD137 and GPC3.

The present disclosure also involves the use of one or more fusion polypeptides as described for complex formation with CD137 and GPC3.

Therefore, in a still further aspect of the disclosure, the disclosed one or more fusion polypeptides are used for the detection of CD137 and GPC3. Such use may include the steps of contacting one or more said fusion polypeptides, under suitable conditions, with a sample suspected of containing CD137 and GPC3, thereby allowing formation of a complex between the fusion polypeptides and CD137 and GPC3, and detecting the complex by a suitable signal. The detectable signal can be caused by a label, as explained above, or by a change of physical properties due to the binding, i.e. the complex formation, itself. One example is surface plasmon resonance, the value of which is changed during binding of binding partners from which one is immobilized on a surface such as a gold foil.

The fusion polypeptides disclosed herein may also be used for the separation of CD137 and GPC3. Such use may include the steps of contacting one or more said fusion polypeptides, under suitable conditions, with a sample supposed to contain CD137 and GPC3, thereby allowing formation of a complex between the fusion polypeptides and CD137 and GPC3, and separating the complex from the sample.

In still another aspect, the present disclosure features a diagnostic or analytical kit comprising a fusion polypeptide according to the disclosure.

In addition to their use in diagnostics, in yet another aspect, the disclosure contemplates a pharmaceutical composition comprising a fusion polypeptide of the disclosure and a pharmaceutically acceptable excipient.

Furthermore, the present disclosure provides fusion polypeptides that simultaneously bind CD137 and GPC3 for use as anti-cancer agents and immune modulators. As such the fusion polypeptides of the present disclosure are envisaged to be used in a method of treatment or prevention of human diseases such as a variety of tumors including hepatocellular carcinoma ("HOC"), melanoma, Merkel cell carcinoma, Wilm's tumor, and hepatoblastoma. Accordingly, also provided are methods of treatment or prevention of human diseases such as a variety of tumors including hepatocellular carcinoma ("HCC"), melanoma, Merkel cell carcinoma, Wilm's tumor, and hepatoblastoma in a subject in need thereof, comprising administering to said subject a therapeutically effective amount of one or more fusion polypeptides of the disclosure.

By simultaneously targeting tumor cells where GPC3 is expressed, such as hepatocellular carcinoma ("HCC"), melanoma, Merkel cell carcinoma, Wilm's tumor, and hepatoblastoma, and activating natural killer (NK) cells in the host innate immune system adjacent to such tumor cells or T-cells of the adaptive immune system, the fusion polypeptide of the disclosure may increase targeted anti-tumor lymphocyte cell activity, enhance anti-tumor immunity and, at the same time, have a direct inhibiting effect on tumor growth, thereby produce synergistic anti-tumor results. In addition, via locally inhibiting oncogene activity and inducing cell-mediated cytotoxicity by NK cells and/or T-cells, the fusion polypeptide of the disclosure may reduce side effects of effector lymphocytes towards healthy cells, i.e. off-target toxicity.

In T cells CD137-mediated signaling leads to the recruitment of TRAF family members and activation of several kinases, including ASK-1, MKK, MAPK3/MAPK4, p38, and JNK/SAPK. Kinase activation is then followed by the activation and nuclear translocation of several transcription factors, including ATF-2, Jun, and NF-κB. In addition to augmenting suboptimal TCR-induced proliferation, CD137-mediated signaling protects T cells, and in particular, CD8+ T cells from activation-induced cell death (AICD).

The present disclosure encompasses the use of a fusion polypeptide of the disclosure or a composition comprising such fusion polypeptide for costimulating T-cells, and/or activating downstream signaling pathways of CD137 when engaging tumor cells where GPC3 is expressed such as hepatocellular carcinoma ("HOC"), melanoma, Merkel cell carcinoma, Wilm's tumor, and hepatoblastoma.

The present disclosure also features a method of costimulating T-cells and/or activating downstream signaling pathways of CD137 when engaging tumor cells where GPC3 is expressed, such as hepatocellular carcinoma ("HCC"), melanoma, Merkel cell carcinoma, Wilm's tumor, and hepatoblastoma, comprising applying one or more fusion polypeptide s of the disclosure or of one or more compositions comprising such fusion polypeptides.

Furthermore, the present disclosure involves a method of activating downstream signaling pathways of CD137 when engaging tumor cells where GPC3 is expressed, hepatocellular carcinoma ("HCC"), melanoma, Merkel cell carcinoma, Wilm's tumor, and hepatoblastoma, comprising applying one or more fusion polypeptides of the disclosure or of one or more compositions comprising such fusion polypeptides.

The present disclosure also contemplates a method of inducing T lymphocyte proliferation when engaging tumor cells where GPC3 is expressed, hepatocellular carcinoma ("HCC"), melanoma, Merkel cell carcinoma, Wilm's tumor, and hepatoblastoma, comprising applying one or more fusion polypeptides of the disclosure or of one or more compositions comprising such fusion polypeptides.

The present disclosure encompasses the use of a fusion polypeptide of the disclosure or a composition comprising such fusion polypeptide for directing CD137 clustering and activation on T-cells to tumor cells where GPC3 is expressed, such as hepatocellular carcinoma ("HCC"), melanoma, Merkel cell carcinoma, Wilm's tumor, and hepatoblastoma.

In another embodiment, the present disclosure also relates to nucleic acid molecules (DNA and RNA) that include nucleotide sequences encoding the fusion polypeptides disclosed herein. In yet another embodiment, the disclosure encompasses a host cell containing said nucleic acid molecule. Since the degeneracy of the genetic code permits substitutions of certain codons by other codons specifying the same amino acid, the disclosure is not limited to a specific nucleic acid molecule encoding a fusion polypeptide as described herein but encompasses all nucleic acid molecules that include nucleotide sequences encoding a functional polypeptide. In this regard, the present disclosure also relates to nucleotide sequences encoding the fusion polypeptides of the disclosure.

In some embodiments, a nucleic acid molecule encoding a lipocalin mutein disclosed in this application, such as DNA, may be "operably linked" to another nucleic acid molecule encoding an immunoglobulin of the disclosure to allow expression of a fusion polypeptide disclosed herein. In this regard, an operable linkage is a linkage in which the sequence elements of one nucleic acid molecule and the sequence elements of another nucleic acid molecule are connected in a way that enables expression of the fusion polypeptide as a single polypeptide.

The disclosure also relates to a method for the production of a or a fusion polypeptide of the disclosure is produced starting from the nucleic acid coding for the polypeptide or any subunit therein by means of genetic engineering methods. In some embodiments, the method can be carried out in vivo, the polypeptide can, for example, be produced in a bacterial or eukaryotic host organism and then isolated from this host organism or its culture. It is also possible to produce a fusion polypeptide of the disclosure in vitro, for example by use of an in vitro translation system.

When producing the fusion polypeptide in vivo, a nucleic acid encoding such polypeptide is introduced into a suitable bacterial or eukaryotic host organism by means of recombinant DNA technology (as already outlined above). For this purpose, the host cell is first transformed with a cloning vector that includes a nucleic acid molecule encoding a fusion polypeptide as described herein using established standard methods. The host cell is then cultured under conditions, which allow expression of the heterologous DNA and thus the synthesis of the corresponding polypeptide. Subsequently, the polypeptide is recovered either from the cell or from the cultivation medium.

In one embodiment of the disclosure, the method includes subjecting at least one nucleic acid molecule encoding hNGAL to mutagenesis at nucleotide triplets coding for at least one, sometimes even more, of the sequence positions corresponding to the sequence positions 28, 40-52, 60, 68, 65, 70, 71-81, 87, 89, 96, 98, 100-106, 114, 118, 120, 125-137 and 145 of the linear polypeptide sequence of hNGAL (SEQ ID NO: 2).

In addition, in some embodiments, the naturally occurring disulphide bond between Cys 76 and Cys 175 may be removed in hNGAL muteins of the disclosure. Accordingly, such muteins can be produced in a cell compartment having a reducing redox milieu, for example, in the cytoplasm of Gram-negative bacteria.

The disclosure also includes nucleic acid molecules encoding the lipocalin muteins of the disclosure, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the lipocalin muteins.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, such as a promoter sequence. In some embodiments a nucleic acid molecule of the disclosure includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the disclosure can also be part of a vector or any other kind of cloning vehicle, such as a plasmid, a phagemid, a phage, a baculovirus, a cosmid or an artificial chromosome.

In one embodiment, the nucleic acid molecule is included in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a fusion polypeptide as described herein, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding a fusion polypeptide as described herein (for example, SEQ ID NOs: 20 and 31), and in particular a cloning vector containing the coding sequence of such a polypeptide can be transformed into a host cell capable of expressing the gene. Transformation can be performed using standard techniques. Thus, the disclosure is also directed to a host cell containing a nucleic acid molecule as disclosed herein.

The transformed host cells are cultured under conditions suitable for expression of the nucleotide sequence encoding a fusion polypeptide of the disclosure. Suitable host cells can be prokaryotic, such as *Escherichia coli* (*E. coli*) or *Bacillus subtilis*, or eukaryotic, such as *Saccharomyces cerevisiae*, *Pichia pastoris*, SF9 or High5 insect cells, immortalized mammalian cell lines (e.g., HeLa cells or CHO cells) or primary mammalian cells.

In some embodiments where a lipocalin mutein of the disclosure, including as comprised in in a fusion polypeptide disclosed herein, includes intramolecular disulphide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmic reticulum of eukaryotic cells and usually favors the formation of structural disulphide bonds.

In some embodiments, it is also possible to produce a fusion polypeptide of the disclosure in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8.).

In some embodiments, a fusion polypeptide of the disclosure as described herein may be not necessarily generated or produced only by use of genetic engineering. Rather, such polypeptide can also be obtained by chemical synthesis such as Merrifield solid phase polypeptide synthesis or by in vitro transcription and translation. It is, for example, possible that promising mutations are identified using molecular modeling and then to synthesize the wanted (designed) mutein or polypeptide in vitro and investigate the binding activity for a target of interest. Methods for the solid phase and/or solution phase synthesis of proteins are well known in the art (see e.g. Bruckdorfer, T. et al. (2004) *Curr. Pharm. Biotechnol.* 5, 29-43).

In another embodiment, a fusion polypeptide of the disclosure may be produced by in vitro transcription/translation employing well-established methods known to those skilled in the art.

The skilled worker will appreciate methods useful to prepare fusion polypeptides contemplated by the present disclosure but whose protein or nucleic acid sequences are not explicitly disclosed herein. As an overview, such modifications of the amino acid sequence include, e.g., directed mutagenesis of single amino acid positions in order to simplify sub-cloning of a polypeptide gene or its parts by incorporating cleavage sites for certain restriction enzymes. In addition, these mutations can also be incorporated to further improve the affinity of a fusion polypeptide for its targets (e.g. CD137 and GPC3). Furthermore, mutations can be introduced to modulate certain characteristics of the polypeptide such as to improve folding stability, serum stability, protein resistance or water solubility or to reduce aggregation tendency, if necessary. For example, naturally occurring cysteine residues may be mutated to other amino acids to prevent disulphide bridge formation.

Additional objects, advantages, and features of this disclosure will become apparent to those skilled in the art upon examination of the following Examples and the attached Figures thereof, which are not intended to be limiting. Thus, it should be understood that although the present disclosure is specifically disclosed by exemplary embodiments and optional features, modification and variation of the disclosures embodied therein herein disclosed may be resorted to by those skilled in the art, and that such modifications and variations are considered to be within the scope of this disclosure.

V. EXAMPLES

Example 1: Expression and Analysis of Antibody-Lipocalin Mutein Fusion Polypeptides We used three approaches to generate bispecific constructs that can bind the targets, GPC3 and CD137, at the same time.

In the first approach, we generated antibody-lipocalin mutein fusion polypeptides based on the CD137-specific antibody, for example, having the heavy and light chains provided by SEQ ID NOs: 34 and 35, and the GPC3 lipocalin mutein, for example, of SEQ ID NO: 10. An unstructured, protease-insensitive (G4S)3 linker (SEQ ID NO: 49) was used to fuse the proteins to each other in all cases. The different formats that were designed are shown in FIG. 1A. The variants generated are fusions of the lipocalin mutein to either one of the four termini of the antibody, which contains an IgG4 backbone mutated to minimize half-antibody exchange (S228P mutation, see SEQ ID NO: 34): SEQ ID NOs: 36 and 37, SEQ ID NOs: 38 and 39, SEQ ID NOs: 40 and 41, SEQ ID NOs: 42 and 43.

In the second approach, we generated fusions of two lipocalin muteins (SEQ ID NO: 10 binding GPC3 and SEQ ID NO: 26 binding CD137) to an engineered IgG4-Fc fragment (SEQ ID NO: 73) which contains a S228P mutation to minimize IgG4 half-antibody exchange in-vitro and in-vivo (cf. Silva 2015) as well as F234A and L235A mutations to reduce Fc-gamma receptor interactions (Alegre 1992). The resulting fusion polypeptides (SEQ ID NO: 44 and SEQ ID NO: 45) are structurally depicted in FIG. 1B.

The constructs of the first and second approaches were generated by gene synthesis and cloned into a mammalian expression vector. They were then transiently expressed in CHO cells. The concentration of antibody-lipocalin mutein fusion polypeptides and IgG4Fc-lipocalin mutein fusion polypeptides in the cell culture medium was measured using a ForteBio ProteinA sensor (Pall Corp.) and quantified using a human IgG1 standard (data not shown).

In the third approach, we generated fusions of two lipocalin muteins (SEQ ID NO: 10 and SEQ ID NO: 26), linked by one or more (G4S)2 linkers (SEQ ID NO: 48), and using two different designs as depicted in FIG. 1C. In the first design, SEQ ID NO: 26 was C-terminally fused to SEQ ID NO: 10, resulting the fusion polypeptide of SEQ ID NO: 46; in the second design, two copies of SEQ ID NO: 26 were C-terminally fused to SEQ ID NO: 10, resulting the fusion polypeptide of SEQ ID NO: 47. The constructs contained a Strep-tag (SEQ ID NO: 50) for affinity chromatography purification. The constructs were cloned using standard methods and expressed in E. coli utilizing periplasmic secretion.

The antibody-lipocalin mutein fusion polypeptides and the IgG4Fc fragment-lipocalin mutein fusion polypeptides were purified using Protein A chromatography followed by size-exclusion chromatography (SEC) in 10 mM histidine pH 5.5 150 mM NaCl or PBS, pH7.4. After SEC purification the fractions containing monomeric protein were pooled and analyzed again using analytical SEC. According to this analysis, the fusion polypeptides were fully monomeric without detectable multimeric species or aggregates (data not shown).

Example 2: Specificity of Fusion Polypeptides Towards GPC3

We employed an ELISA assay to determine the specificity of the fusion polypeptides of SEQ ID NOs: 36 and 37, SEQ ID NOs: 38 and 39, SEQ ID NOs: 40 and 41 and SEQ ID NOs: 42 and 43 to recombinant human GPC3 (R&D Systems #2119-GP-050/CF). The target was dissolved in PBS (1 pg/mL) and coated overnight on microtiter plates at 4° C. The plate was washed after each incubation step with 100 µL PBS supplemented with 0.1% (v/v) Tween 20 (PBS-T) five times. The plates were blocked with 2% BSA (w/v) in PBS-T for 1 h at room temperature and subsequently washed. Different concentrations of the lipocalin mutein (SEQ ID NO: 10) or the fusion polypeptides were added to the wells and incubated for 1 h at room temperature, followed by a wash step. Bound fusion protein or lipocalin mutein was detected after incubation with 1:1000 diluted anti-human NGAL antibody conjugated to HRP in PBS-T supplemented with 2% (w/v) BSA (PBS-TB). After an additional wash step, fluorogenic HRP substrate (QuantaBlu, Thermo) was added to each well and the fluorescence intensity was detected using a fluorescence microplate reader.

The result of the experiment is depicted in FIG. 2, together with the fit curves resulting from a 1:1 binding sigmoidal fit, where the EC50 value and the maximum signal were free parameters, and the slope was fixed to unity. The resulting EC50 values are provided in Table 1, including the errors of the sigmoidal fit of the data, which is the case for all data summarized in tables herein. The observed EC50 values are in a similar range for all antibody-lipocalin mutein fusion polypeptides (0.25-0.28 nM), all slightly better than the lipocalin mutein (SEQ ID NO: 10), which was at 0.55 nM. The experiment shows that when included in fusion polypeptides described above the lipocalin mutein can be fused to either one of the four termini of the antibody without a loss in activity towards GPC3.

TABLE 1

| ELISA data for GPC3 binding | |
| --- | --- |
| Name | EC50 GPC3 [nM] |
| SEQ ID NOs: 42 and 43 | 0.27 ± 0.03 |
| SEQ ID NOs: 40 and 41 | 0.25 ± 0.02 |
| SEQ ID NOs: 38 and 39 | 0.26 ± 0.02 |
| SEQ ID NOs: 36 and 37 | 0.28 ± 0.02 |
| SEQ ID NO: 10 | 0.55 ± 0.03 |

Example 3: Specificity of Fusion Polypeptides Towards Human CD137

We employed an ELISA assay to determine the specificity of the fusion polypeptides of SEQ ID NOs: 36 and 37, SEQ ID NOs: 38 and 39, SEQ ID NOs: 40 and 41 and SEQ ID NOs: 42 and 43 to recombinant CD137-Fc fusion protein (#838-4B-100, R&D Systems). The antibody of SEQ ID NOs: 34 and 35 served as the positive control. The target was dissolved in PBS (1 pg/mL) and coated overnight on microtiter plates at 4° C. The plate was washed after each incubation step with 100 µL PBS-T five times. The plates were blocked with 2% BSA (w/v) in PBS-T for 1 h at room temperature and subsequently washed. Different concentrations of the CD137-specific antibody or the fusion polypeptides were added to the wells and incubated for 1 h at room temperature, followed by a wash step. Bound fusion protein was detected after incubation for 1 h at room temperature with 1:5000 diluted mouse anti-human IgG Fab antibody conjugated to HRP (Jackson Laboratories) in PBS-TB. After an additional wash step, fluorogenic HRP substrate (QuantaBlu, Thermo) was added to each well and the fluorescence intensity was detected using a fluorescence microplate reader.

The result of the experiment is depicted in FIG. 3, together with the fit curves resulting from a 1:1 binding sigmoidal fit, where the EC50 value and the maximum signal were free parameters, and the slope was fixed to unity. The resulting EC50 values are provided in Table 2. The observed EC50 values for all tested molecules were very similar and ranged from 1.5 nM to 2.3 nM. The experiment shows that when included in fusion polypeptides described the antibody can be fused with the lipocalin mutein at either one of the four termini of the antibody without a loss in activity towards CD137.

TABLE 2

| ELISA data for CD137 binding | |
| --- | --- |
| Name | EC50 CD137 [nM] |
| SEQ ID NOs: 42 and 43 | 2.1 ± 0.03 |
| SEQ ID NOs: 40 and 41 | 2.0 ± 0.02 |
| SEQ ID NOs: 38 and 39 | 2.3 ± 0.02 |
| SEQ ID NOs: 36 and 37 | 1.6 ± 0.02 |
| SEQ ID NOs: 34 and 35 | 1.5 ± 0.03 |

Example 4: Demonstration of Simultaneous Target Binding of Fusion Polypeptides in an ELISA-Based Setting In order to demonstrate the simultaneous binding of the fusion polypeptides of SEQ ID NOs: 36 and 37, SEQ ID NOs: 38 and 39, SEQ ID NOs: 40 and 41 and SEQ ID NOs: 42 and 43 to both GPC3 and CD137, a dual-binding ELISA format was used. Recombinant human CD137-Fc fusion protein (R&D Systems) in PBS (1 pg/mL) was coated overnight on microtiter plates at 4° C. The plate was washed five times after each incubation step with 100 µL PBS-T. The plates were blocked with 2% BSA (w/v) in PBS-T for 1 h at room temperature and subsequently washed again. Different concentrations of the fusion polypeptides were added to the wells and incubated for 1 h at room temperature, followed by a wash step. Subsequently, biotinylated human GPC3 was added at a constant concentration of 1 pg/mL in PBS-TB for 1 h. After washing, Extravidin-HRP (Sigma- Adrich, 1:5000 in PBS-TB) was added to the wells for 1 h. After an additional wash step, fluorogenic HRP substrate (QuantaBlu, Thermo) was added to each well and the fluorescence intensity was detected using a fluorescence microplate reader.

The result of the experiment is depicted in FIG. 4, together with the fit curves resulting from a 1:1 binding sigmoidal fit, where the EC50 value and the maximum signal were free parameters, and the slope was fixed to unity. The resulting EC50 values are provided in Table 3. All fusion polypeptides showed clear binding signals with EC50 values ranging from 1.7-2.1 nM, demonstrating that the fusion polypeptides are able to engage GPC3 and CD137 simultaneously.

TABLE 3

ELISA data for simultaneous target binding

| Name | EC50 Dual binding [nM] |
|---|---|
| SEQ ID NOs: 42 and 43 | 1.92 ± 0.27 |
| SEQ ID NOs: 40 and 41 | 1.97 ± 0.32 |
| SEQ ID NOs: 38 and 39 | 2.06 ± 0.36 |
| SEQ ID NOs: 36 and 37 | 1.74 ± 0.25 |

Example 5: Affinity of Antibody and Fusion Polypeptides to Human GPC3

Binding affinities of the lipocalin mutein of SEQ ID NO: 10 and the fusion polypeptides of SEQ ID NOs: 36 and 37, SEQ ID NOs: 38 and 39, SEQ ID NOs: 40 and 41 as well as SEQ ID NOs: 42 and 43 to recombinant human GPC3 (R&D Systems #2119-GP-050/CF) were determined by Surface Plasmon Resonance (SPR) using a Biacore T200 instrument (GE Healthcare). In the SPR affinity assay, biotinylated GPC3 was captured on a sensor chip ("CAP chip") using the Biotin CAPture Kit (GE Healthcare): sensor Chip CAP is pre-immobilized with an ssDNA oligo. Undiluted Biotin CAPture Reagent (streptavidin conjugated with the complementary ss-DNA oligo) was applied at a flow rate of 2 μL/min for 300 s. For analysis of the lipocalin mutein, biotinylated GPC3 at a concentration of 1 pg/mL was used and 0.25 pg/mL of biotinylated GPC3 for the fusions proteins. The biotinylated GPC3 was applied for 300 s at a flow rate of 5 μL/min. GPC3 was biotinylated by incubation with EZ-Link® NHS-PEG4-Biotin (5-fold molar excess (Thermo Scientific)) during two hours at room temperature. The excess of non-reacted biotin reagent was removed by loading the reaction mixture onto a Zeba™ Spin Desalting Plate (Thermo Scientific). The reference channel was loaded with Biotin CAPture Reagent only.

To determine the affinity, GCP3 was immobilized on the chip surface and four different concentrations (11.1, 3.7, 1.2 and 0.4 nM) of each tested agent (fusion polypeptides or lipocalin mutein) were prepared in running buffer (10 mM HEPES, 150 mM NaCl, 0.05% v/v Surfactant P20, 3 mM EDTA, pH 7.4 (GE Healthcare)) and applied to the chip surface. Applying a flow rate of 30 μL/min, the sample contact time was 180 s and dissociation time was 1200 s. All measurements were performed at 25° C. Regeneration of the Sensor Chip CAP surface was achieved with an injection of 6 M guanidinium-HCl with 0.25 M NaOH followed by an extra wash with running buffer and a stabilization period of 120 s. Prior to the protein measurements three regeneration cycles were performed for conditioning purposes. Data were evaluated with Biacore T200 Evaluation software (V 2.0). Double referencing was used and the 1:1 Binding model was used to fit the raw data.

The data is depicted in FIG. 5, and the fit results are summarized in Table 4. From the data it can be concluded that the fusion polypeptides bind GPC3 with affinities that are very similar to the lipocalin mutein of SEQ ID NO: 10. Apparent binding affinities were in the range of 17-30 pM for the fusion polypeptides and the apparent binding affinity was 12 pM for the lipocalin mutein of SEQ ID NO: 10.

TABLE 4

Binding affinities for GPC3

| Name | $K_D$ [pM] |
|---|---|
| SEQ ID NO: 10 | 12 |
| SEQ ID NOs: 36 and 37 | 24 |
| SEQ ID NOs: 42 and 43 | 30 |
| SEQ ID NOs: 40 and 41 | 17 |
| SEQ ID NOs: 38 and 39 | 20 |

Example 6: Affinity of Antibody and Fusion Polypeptides to Human CD137

Binding affinities of the antibody of SEQ ID NOs: 34 and 35 and the fusion polypeptides of SEQ ID NOs: 36 and 37, SEQ ID NOs: 38 and 39, SEQ ID NOs: 40 and 41 and SEQ ID NOs: 42 and 43 to recombinant human CD137-Fc fusion protein (#838-4B-100, R&D Systems) were determined by Surface Plasmon Resonance (SPR) in analogy to Example 5. Briefly, biotinylated CD137-Fc was captured on a sensor chip CAP and four dilutions (20, 5, 1.3 and 0.3 nM) of each tested agent (fusion protein or SEQ ID NOs: 34 and 35) were prepared in running buffer and applied to the chip surface. Applying a flow rate of 30 μL/min, the sample contact time was 180 s and dissociation time was 600 s. All measurements were otherwise performed and analyzed as described in Example 5.

The results are summarized in Table 5. The data shows that the fusion polypeptides bind CD137 with affinities that are very similar to the antibody. Apparent binding affinities were in the range of 71-179 pM for the fusion proteins and the apparent binding affinity was 92 pM for the antibody 20H4.9 (SEQ ID NOs: 34 and 35).

TABLE 5

Binding affinities for CD137

| Name | $K_D$ [pM] |
|---|---|
| SEQ ID NOs: 34 and 35 | 92 |
| SEQ ID NOs: 36 and 37 | 71 |
| SEQ ID NOs: 42 and 43 | 62 |
| SEQ ID NOs: 40 and 41 | 101 |
| SEQ ID NOs: 38 and 39 | 179 |

Example 7: Specificity of Lipocalin Mutein Fc-Fusion Polypeptides Towards GPC3

We employed an ELISA assay as described in Example 2 to determine the specificity of the fusion polypeptides, SEQ ID NO: 44 and SEQ ID NO: 45, to recombinant human GPC3.

The result of the experiment is depicted in FIG. 7, together with the fit curves resulting from a 1:1 binding sigmoidal fit, where the EC50 value and the maximum signal were free parameters, and the slope was fixed to unity. The resulting EC50 values are provided in Table 6. The observed EC50 values for the lipocalin mutein Fc-fusion polypeptides were both better than for the GPC3-binding lipocalin mutein (SEQ ID NO: 10).

TABLE 6

ELISA data for GPC3 binding

| Name | EC50 GPC3 [nM] |
|---|---|
| SEQ ID NO: 44 | 0.07 ± 0.04 |
| SEQ ID NO: 45 | 0.12 ± 0.02 |
| SEQ ID NO: 10 | 0.32 ± 0.04 |

Example 8: Specificity of Lipocalin Mutein Fc-Fusion Polypeptides Towards Human CD137

We employed an ELISA assay to determine the specificity of the lipocalin mutein Fc-fusion polypeptides of SEQ ID NO: 44 and SEQ ID NO: 45 to recombinant CD137-Fc fusion polypeptide as described in Example 3.

The result of the experiment is depicted in FIG. 8, together with the fit curves resulting from a 1:1 binding sigmoidal fit, where the EC50 value and the maximum signal were free parameters, and the slope was fixed to unity. The resulting EC50 values are provided in Table 7. The observed EC50 values for the lipocalin mutein Fc-fusion polypeptides were both better than the observed EC50 value for the CD137-binding lipocalin mutein (SEQ ID NO: 26).

TABLE 7

ELISA data for CD137 binding

| Name | EC50 CD137 [nM] |
|---|---|
| SEQ ID NO: 44 | 0.13 ± 0.01 |
| SEQ ID NO: 45 | 0.21 ± 0.01 |
| SEQ ID NO: 26 | 0.43 ± 0.03 |

Example 9: Demonstration of Simultaneous Target Binding of Lipocalin Mutein Fc-Fusion Polypeptides in an ELISA-Based Setting In order to demonstrate the simultaneous binding of the fusion polypeptides of SEQ ID NO: 44 and SEQ ID NO: 45 to GPC3 and CD137, a dual-binding ELISA format was used in analogy to Example 4.

The result of the experiment is depicted in FIG. 9, together with the fit curves resulting from a 1:1 binding sigmoidal fit, where the EC50 value and the maximum signal were free parameters, and the slope was fixed to unity. The resulting EC50 values are provided in Table 8. Both fusion polypeptides showed clear binding signals with EC50 values close to 1.7 nM, demonstrating that the fusion polypeptides are able to engage GPC3 and CD137 simultaneously.

TABLE 8

ELISA data for simultaneous target binding

| Name | EC50 Dual binding [nM] |
|---|---|
| SEQ ID NO: 44 | 1.72 ± 0.26 |
| SEQ ID NO: 45 | 1.70 ± 0.30 |

Example 10: Affinity of Antibody and Fusion Polypeptides to Human GPC3

Binding affinities of the GPC3-binding lipocalin mutein of SEQ ID NO: 10 and the fusion polypeptides of SEQ ID NO: 44 and SEQ ID NO: 45 to recombinant human GPC3 were determined by Surface Plasmon Resonance as described in Example 5.

The data is depicted in FIG. 10, and the fitted $K_D$ values are summarized in Table 9. The data shows that the fusion polypeptides bind GPC3 with affinities that are very similar to the lipocalin mutein. Apparent binding affinities are 23 pM and 29 pM for the fusion polypeptides, respectively, compared to the apparent binding affinity of 33 pM for the lipocalin mutein.

TABLE 9

Binding affinities for GPC3

| Name | $K_D$ [pM] |
|---|---|
| SEQ ID NO: 10 | 33 |
| SEQ ID NO: 44 | 29 |
| SEQ ID NO: 45 | 23 |

Example 11: Affinity of Antibody and Fusion Polypeptides to Human CD137

Binding affinities of the CD137-binding lipocalin mutein of SEQ ID NO: 26 and the fusion polypeptides of SEQ ID NO: 44 and SEQ ID NO: 45 to recombinant human CD137-Fc fusion protein were determined in analogy to Example 6.

The data is depicted in FIG. 11 for the fusion polypeptides of SEQ ID NO: 44 and SEQ ID NO: 45 and the fitted $K_D$ values for all tested molecules are in Table 10. The data shows that the fusion polypeptides bind CD137 with affinities of 1 nM or 1.1 nM, respectively, superior to the $K_D$ value of the lipocalin mutein, which has a value of 2.3 nM.

TABLE 10

Binding affinities for CD137

| Name | $K_D$ [nM] |
|---|---|
| SEQ ID NO: 26 | 2.3 |
| SEQ ID NO: 44 | 1.1 |
| SEQ ID NO: 45 | 1.0 |

Example 12: Specificity of Fusion Polypeptide Towards GPC3

We generated an additional fusion polypeptide based on the CD137-binding antibody of SEQ ID NOs: 51 and 52 and the GPC3-binding lipocalin mutein of SEQ ID NO: 10. The lipocalin mutein was C-terminally fused to the heavy chain using a (G4S)3 linker to resulting the fusion polypeptide of SEQ ID NOs: 53 and 54.

We employed an ELISA assay as described in Example 2 to determine the specificity of the fusion polypeptide of SEQ ID NOs: 53 and 54 to recombinant human GPC3.

The result of the experiment is depicted in FIG. 12, together with the fit curves resulting from a 1:1 binding sigmoidal fit, where the EC50 value and the maximum signal were free parameters, and the slope was fixed to unity. The resulting EC50 values are provided in Table 11. The EC50 towards GPC3 is comparable for the fusion polypeptide and the lipocalin mutein. The data shows that when included in the fusion polypeptide the lipocalin mutein can be fused to the antibody without a loss of activity towards GPC3.

TABLE 11

ELISA data for GPC3 binding

| Name | EC50 GPC3 [nM] |
|---|---|
| SEQ ID NOs: 53 and 54 | 0.62 ± 0.05 |
| SEQ ID NO: 10 | 0.55 ± 0.03 |

Example 13: Demonstration of Simultaneous Target Binding of Fusion Polypeptide in an ELISA-Based Setting In order to demonstrate the simultaneous binding of the fusion polypeptides of SEQ ID NOs: 53 and 54 to both GPC3 and CD137, a dual-binding ELISA format was used in analogy to Example 4.

The result of the experiment is depicted in FIG. 13, together with the fit curves resulting from a 1:1 binding sigmoidal fit, where the EC50 value and the maximum signal were free parameters, and the slope was fixed to unity. The fusion polypeptide showed clear binding signals with an EC50 value of 4.66±0.65 nM, demonstrating that the polypeptide is able to engage GPC3 and CD137 simultaneously.

Example 14: Specificity of Fusion Polypeptides Towards GPC3

We employed an ELISA assay as described in Example 2 to determine the specificity of the bispecific fusion polypeptides of SEQ ID NO: 46 and SEQ ID NO: 47 as well as the lipocalin mutein of SEQ ID NO: 8 to recombinant human GPC3.

The result of the experiment is depicted in FIG. 14, together with the fit curves resulting from a 1:1 binding sigmoidal fit, where the EC50 value and the maximum signal were free parameters, and the slope was fixed to unity. The resulting EC50 values are provided in Table 12. The EC50 values for the fusion polypeptides are at least as good as or even superior to the EC50 value of the lipocalin mutein. The data demonstrate that when included in the two fusion polypeptides the lipocalin mutein can be fused to the antibody without a loss in activity towards GPC3.

TABLE 12

ELISA data for GPC3 binding

| Name | EC50 GPC3 [nM] |
|---|---|
| SEQ ID NO: 46 | 0.14 ± 0.02 |
| SEQ ID NO: 47 | 0.16 ± 0.03 |
| SEQ ID NO: 8 | 0.24 ± 0.02 |

Example 15: Specificity of Fusion Polypeptides Towards Human CD137

We employed an ELISA assay to determine the specificity of bispecific polypeptides of SEQ ID NO: 46 and SEQ ID NO: 47 as well as the lipocalin mutein of SEQ ID NO: 26 to recombinant CD137-Fc fusion protein as described in Example 3.

The result of the experiment is plotted in FIG. 15, together with the fit curves resulting from a 1:1 binding sigmoidal fit, where the EC50 value and the maximum signal were free parameters, and the slope was fixed to unity. The resulting EC50 values are provided in Table 13. The EC50 values for the fusion polypeptides are at least as good as or even superior to the EC50 value of the lipocalin mutein. The data demonstrate that when included in the two fusion polypeptides the antibody can be fused to the lipocalin mutein without a loss in activity towards CD137.

TABLE 13

ELISA data for CD137 binding

| Name | EC50 CD137 [nM] |
|---|---|
| SEQ ID NO: 46 | 0.20 ± 0.02 |
| SEQ ID NO: 47 | 0.26 ± 0.01 |
| SEQ ID NO: 26 | 0.28 ± 0.02 |

Example 16: Demonstration of Simultaneous Target Binding of Fusion Polypeptides in an ELISA-Based Setting In order to demonstrate the simultaneous binding of bispecific polypeptides of SEQ ID NO: 46 and SEQ ID NO: 47 to GPC3 and CD137, a dual-binding ELISA format was used in analogy to Example 4.

The result of the experiment is depicted in FIG. 16, together with the fit curves resulting from a 1:1 binding sigmoidal fit, where the EC50 value and the maximum signal were free parameters, and the slope was fixed to unity. Both fusion polypeptides showed clear binding signals with EC50 values of 7.3-7.5 nM, demonstrating that both fusion polypeptides are able to engage GPC3 and CD137 simultaneously.

TABLE 14

ELISA data for simultaneous target binding

| Name | EC50 Dual binding [nM] |
|---|---|
| SEQ ID NO: 46 | 7.30 ± 0.94 |
| SEQ ID NO: 47 | 7.47 ± 0.79 |

Example 17: Affinity of Fusion Polypeptides to Human GPC3

Binding affinities of the GPC3-binding lipocalin mutein and the bispecific polypeptides of SEQ ID NO: 46 and SEQ ID NO: 47 to recombinant human GPC3 and recombinant human CD137 were determined by Surface Plasmon Resonance on a Biacore T200 instrument (GE Healthcare) using HBS-EP+(1x; BR-1006-69; GE Healthcare) as running buffer, in analogy to the procedure described in Example 5.

The Biotin CAPture Kit (GE Healthcare) was used to immobilize biotinylated bispecific polypeptides on the chip surface. The bispecific polypeptides were biotinylated using standard NHS chemistry. Undiluted Biotin CAPture Reagent (streptavidin conjugated with ss-DNA oligo) was captured on a Sensor Chip CAP with the pre-immobilized complementary ss-DNA oligo. Thereafter, biotinylated muteins at 1 pg/ml were applied for 300 s at a flow rate of 5 µL/min.

GPC3 was applied in four concentrations (300 nM, 100 nM, 33 nM and 11 nM) at a flow rate of 30 µL/min. The GPC3 was injected with for 180 s and the subsequent dissociation time was set to of 1200 s. Regeneration of the chip surface was achieved by injecting 6 M Guanidinium-HCl+0.25 M NaOH (120 s) with a flow rate of 10 µL/min. Injection of regeneration solutions was followed by an extra wash step with HBS-EP+(1x; BR-1006-69; GE Healthcare) running buffer and a stabilization period of 120 s.

The data were double-referenced by subtraction of the corresponding signals measured for the control channel (loaded with Biotin CAPture reagent only) and by subtraction of buffer injections from the binding responses. Association rate constant $k_a$ and dissociation rate constant $k_d$ for the binding reaction were determined using Biacore T200 Evaluation Software V2.0 for data processing and kinetic fitting.

The respective sensorgrams are shown in FIG. 17. The results are summarized in Table 15. The data shows that the bispecific polypeptides bind GPC3 with affinities of 4.3 nM (SEQ ID NO: 46) and 3.5 nM (SEQ ID NO: 47), respectively.

TABLE 15

Binding affinities for GPC3

| Name | $K_D$ [nM] |
| --- | --- |
| SEQ ID NO: 46 | 4.3 |
| SEQ ID NO: 47 | 3.5 |

Example 18: Affinity of Fusion Polypeptides to Human CD137

Binding affinities of the CD137-binding lipocalin mutein and the bispecific polypeptides of SEQ ID NO: 46 and SEQ ID NO: 47 to recombinant human CD137-Fc fusion protein (#838-4B-100, R&D Systems) were determined by Surface Plasmon Resonance using a Biacore T200 instrument (GE Healthcare) in analogy to Example 6. Prior to the SPR affinity assay, a CM5 sensor chip was derivatized with an anti-human Fc antibody using the Human Antibody Capture Kit (GE Healthcare #BR-1008-39) according to the manufacturer's instructions.

To determine the affinity, human CD137-Fc fusion protein was immobilized on the chip at a concentration of 0.25 mg/lm at a flow rate of 10 µL/min and a contact time of 180. Four different concentrations (1000 nM, 200 nM, 40 nM and 8 nM) of the bispecific polypeptides were prepared in running buffer (10 mM HEPES, 150 mM NaCl, 0.05% v/v Surfactant P20, 3 mM EDTA, pH 7.4 (GE Healthcare)) and applied to the chip surface. Applying a flow rate of 30 µL/min, the sample contact time was 180 s and dissociation time was 600 s. All measurements were performed at 25° C. Regeneration of the sensor chip surface was achieved with an injection of 10 mM glycine pH 1.7 followed by an extra wash with running buffer and a stabilization period of 120 s. Prior to the protein measurements three regeneration cycles were performed for conditioning purposes. Data were evaluated with Biacore T200 Evaluation software (V 2.0). Double referencing was used and the 1:1 Binding model was used to fit the raw data.

The results are shown in FIG. 18 and summarized in Table 16. The data shows that the bispecific polypeptides bind CD137 with affinities that are at least as good as the affinity of the lipocalin mutein towards CD137.

TABLE 16

Binding affinities for CD137

| Name | $K_D$ [pM] |
| --- | --- |
| SEQ ID NO: 26 | 2.3 |
| SEQ ID NO: 46 | 1.6 |
| SEQ ID NO: 47 | 0.6 |

Example 19: Functional T-Cell Activation Assay Using Coated Fusion Polypeptides

We employed a T-cell activation assay to assess the ability of the fusion polypeptides of SEQ ID NOs: 36 and 37, SEQ ID NOs: 38 and 39, SEQ ID NOs: 40 and 41 and SEQ ID NOs: 42 and 43 to co-stimulate T-cell responses. For this purpose, fusion polypeptides at different concentrations were coated onto a plastic dish together with an anti-human CD3 antibody (OKT3, eBioscience) and purified T-cells were subsequently incubated on the coated surface in the presence of soluble anti-human CD28 antibody (Clone 28.2; eBioscience). As the readout, we measured supernatant interleukin 2 (IL-2) levels. As negative control, a human IgG4 isotype as negative control was utilized. In the following, we provide a detailed description of the experiment.

Human peripheral blood mononuclear cells (PBMC) from healthy volunteer donors were isolated from buffy coats by centrifugation through a Polysucrose density gradient (Biocoll® 1.077 g/mL from Biochrom), following Biochrom's protocols. The T lymphocytes were isolated from the resulting PBMC using a Pan T-cell purification Kit (Miltenyi Biotec GmbH) and the manufacturer's protocols. Purified T-cells were resuspended in a buffer consisting of 90% FCS and 10% DMSO, immediately frozen down using liquid nitrogen and stored in liquid nitrogen until further use. For the assay, T cells were thawed for 16 h and cultivated in culture media (RPMI 1640, Life Technologies) supplemented with 10% FCS and 1% Penicillin-Streptomycin (Life Technologies).

The following procedure was performed using triplicates for each experimental condition. Flat-bottom tissue culture plates were coated overnight at 4° C. using 200 µL of a mixture of 0.5 pg/mL anti-CD3 antibody and a dilution series of the fusion polypeptides of SEQ ID NOs: 36 and 37, SEQ ID NOs: 38 and 39, SEQ ID NOs: 40 and 41, and SEQ ID NOs: 42 and 43 (25 µg/mL, 2.5 µg/mL, and 0.25 µg/mL) or of the IgG4 isotype negative control (25 µg/mL). In another setting with same experimental condition, the fusion polypeptides were coated together with an IgG1 isotype (as a further negative control) instead of the anti-CD3 antibody. The following day, wells were washed twice with PBS, and 100 µL of the T-cell suspension (corresponding to $5 \times 10^4$ T cells) in culture media supplemented with 2 µg/mL anti-hCD28 antibody was added to each well. Plates were covered with a gas permeable seal (4titude) and incubated at 37° C. in a humidified 5% $CO_2$ atmosphere for 3 days. Subsequently, IL-2 concentration in the supernatant, as well as cell proliferation, were assessed.

Human IL-2 levels in the pooled cell culture supernatants were quantified using the IL-2 DuoSet DuoSet kit from R&D Systems. The procedure was carried out as described below. In the first step, a 384 well plate was coated at room temperature for 2 h with 1 μg/mL "Human IL-2 Capture Antibody" (R&D System) diluted in PBS. Subsequently, wells were washed 5 times with 80 μl PBS-T (PBS containing 0.05% Tween20) using a Biotek EL405 select CW washer (Biotek). After 1 h blocking in PBS-T additionally containing 1% casein (w/w), pooled supernatant and a concentration series of an IL-2 standard diluted in culture medium were incubated in the 384-well plate overnight at 4° C. To allow for detection and quantitation of captured IL-2, a mixture of 100 ng/mL biotinylated goat anti-hI L-2-Bio detection antibody (R&D System) and 1μg/mL Sulfotag-labelled streptavidin (Mesoscale Discovery) were added in PBS-T containing 0.5% casein and incubated at room temperature for 1 h. After washing, 25 μL reading buffer was added to each well and the electrochemiluminescence (ECL) signal of every well was read using a Mesoscale Discovery reader. Analysis and quantification were performed using Mesoscale Discovery software.

The result of the experiment is depicted in FIG. 19. For all four fusion polypeptides (SEQ ID NOs: 36 and 37, SEQ ID NOs: 38 and 39, SEQ ID NOs: 40 and 41 and SEQ ID NOs: 42 and 43), there is a clear induction of IL-2 production by the employed T-cells, compared to the negative control isotype IgG4. The data further shows a tendency towards stronger IL-2 induction at higher coating concentrations of the polypeptide fusions. In the absence of anti-CD3 stimulation of the T-cells, the fusion polypeptides did not induce IL-2 production by the T-cells. This demonstrates that the fusion polypeptides are capable of co-stimulating the activation of T-cells stimulated with an anti-CD3 and an anti-CD28 antibody at suboptimal concentrations.

Example 20: Functional T-Cell Activation Assay Using Tumor Cell Bound Fusions Polypeptides We employed a target-cell dependent T-cell activation assay to assess the ability of the fusion polypeptides of SEQ ID NOs: 36 and 37, SEQ ID NO: 44 and SEQ ID NO: 45 capable of binding CD137 and GPC3 at the same time—to co-stimulate T-cell responses when immobilized on a GPC3-positive cell line. As a negative control, we employed the monospecific, CD137-binding antibody of SEQ ID NOs: 34 and 35. In the experiment, an anti-human CD3 antibody (OKT3, eBioscience) was coated on a plastic culture dish, and subsequently GPC3-positive HepG2 cells were cultured on the dish overnight. The next day, purified T-cells were incubated on the coated surface in the presence of 1 μg/mL fusion polypeptides of SEQ ID NOs: 36 and 37, SEQ ID NO: 44, and SEQ ID NO: 45 or the control antibody of SEQ ID NOs: 34 and 35. As readout, we measured supernatant interleukin 2 (IL-2)) levels. In the following, the experiment is described in detail.

Human peripheral blood mononuclear cells (PBMC) from healthy volunteer donors were isolated from buffy coats by centrifugation through a Polysucrose density gradient (Biocoll® 1.077 g/mL from Biochrom), following Biochrom's protocols. The T lymphocytes were isolated from the resulting PBMC using a Pan T-cell purification Kit (Miltenyi Biotec GmbH) and the manufacturer's protocols. Purified T-cells were resuspended in a buffer consisting of 90% FCS and 10% DMSO, immediately frozen down using liquid nitrogen and stored in liquid nitrogen until further use. For the assay, T cells were thawed for 16 h and cultivated in culture media (RPMI 1640, Life Technologies) supplemented with 10% FCS and 1% Penicillin-Streptomycin (Life Technologies).

The following procedure was performed using triplicates for each experimental condition. Flat-bottom tissue culture plates were pre-coated or not for 1 h at 37° C. using 200 μL of 0.25 μg/mL anti-CD3 antibody. Wells were subsequently washed twice with PBS. $1.25 \times 10^4$ HepG2 tumor cells per well were plated and allowed to adhere overnight at 37° C. in a humidified 5% $CO_2$ atmosphere. The HepG2 cells had before been grown in culture under standard conditions, detached using Accutase and resuspended in culture media. On the next days, tumor cells were treated 2 hours at 37° C. with mitomycin C (Sigma Aldrich) at the concentration of 10μg/ml in order to block their proliferation. Plates were washed twice with PBS, and 100 μL of the T-cell suspension (corresponding to $5 \times 10^4$ T cells) and the fusion polypeptides or negative control at a concentration of 1 μg/mL were added to each well. Plates were covered with a gas permeable seal (4titude) and incubated at 37° C. in a humidified 5% $CO_2$ atmosphere for 3 days. Subsequently, IL-2 concentration in the supernatant were assessed as described below.

Human IL-2 levels in the cell culture supernatants were quantified using the IL-2 DuoSet kit from R&D Systems. The procedure is carried out and described in the following. In the first step, a 384 well plate was coated at room temperature for 2 h with 1 μg/mL "Human IL-2 Capture Antibody" (R&D System) diluted in PBS. Subsequently, wells were washed 5 times with 80 μl PBS-T (PBS containing 0.05% Tween20) using a Biotek EL405 select CW washer (Biotek). After 1 h blocking in PBS-T additionally containing 1% casein (w/w), pooled supernatant and a concentration series of an IL-2 standard diluted in culture medium were incubated in the 384-well plate overnight at 4° C. To allow for detection and quantitation of captured IL-2, a mixture of 100 ng/mL biotinylated goat anti-hIL-2-Bio detection antibody (R&D System) and 1μg/mL Sulfotag-labelled streptavidin (Mesoscale Discovery) were added in PBS-T containing 0.5% casein and incubated at room temperature for 1 h. After washing, 25 μL reading buffer was added to each well and the electrochemiluminescence (ECL) signal of every well was read using a Mesoscale Discovery reader. Analysis and quantification were performed using Mesoscale Discovery software.

The result of the experiment is depicted in FIG. 20. For the three fusion polypeptides of SEQ ID NOs: 36 and 37, SEQ ID NO: 44, and SEQ ID NO: 45, there is a clear induction of IL-2 production by the employed T-cells, compared to the control antibody of SEQ ID NOs: 34 and 35. This shows that the fusion polypeptides of the disclosure are capable of co-stimulating T-cell activation in a target-dependent manner, as evidenced by that the GPC3-binding fusion polypeptides exhibit higher levels of IL-2 production than the control antibody.

Example 21: Functional T-Cell Activation Assay Using Tumor Cell Bound Fusions Polypeptides with and without Blockade of Bispecific Binding We employed a target-cell dependent T-cell activation assay, similar to the experiment described in Example 20, to assess the ability of the fusion polypeptides of SEQ ID NO: 44 and SEQ ID NO: 45 capable of binding CD137 and GPC3 at the same time—to co-stimulate T-cell responses when bound to a GPC3-positive cell line. As a control, the experiment was performed in the presence of an excess of the monospecific, GPC3-binding Anticalin of SEQ ID NO:

10 in order to displace the bispecific constructs SEQ ID NO: 44 or SEQ ID NO: 45 from binding to the GPC3-positive cells. In the experiment, an anti-human CD3 antibody (OKT3, eBioscience) was coated on a plastic culture dish, and subsequently GPC3-positive Hep3B cells were cultured on the dish overnight. The next day, purified T-cells were incubated on the coated surface in the presence of four concentrations of the fusion polypeptides of SEQ ID NO: 44 and SEQ ID NO: 45 (1μg/mL, 0.1 μg/mL, 0.01 μg/mL, 0.001 μg/mL). In parallel, the experiment was performed with the addition of an excess of SEQ ID NO: 10 (1 mg/mL). As a readout, we measured supernatant interleukin 2 (IL-2) levels. In the following, the experiment is described in detail.

Human peripheral blood mononuclear cells (PBMC) from healthy volunteer donors were isolated from buffy coats by centrifugation through a Polysucrose density gradient (Biocoll® 1.077 g/mL from Biochrom), following Biochrom's protocols. The T lymphocytes were isolated from the resulting PBMC using a Pan T-cell purification Kit (Miltenyi Biotec GmbH) and the manufacturer's protocols. The purified T cells were cultivated in culture media (RPMI 1640, Life Technologies) supplemented with 10% FCS and 1% Penicillin-Streptomycin (Life Technologies).

The following procedure was performed using triplicates for each experimental condition. Flat-bottom tissue culture plates were pre-coated for 1 h at 37° C. using 200 μL of 0.25 μg/mL anti-CD3 antibody. Wells were subsequently washed twice with PBS. $1.25 \times 10^4$ Hep3B tumor cells per well were plated and allowed to adhere overnight at 37° C. in a humidified 5% $CO_2$ atmosphere. The Hep3B cells had before been grown in culture under standard conditions, detached using Accutase and resuspended in culture media.

On the next day, tumor cells were treated 2 hours at 37° C. with mitomycin C (Sigma Aldrich) at the concentration of 10μg/ml in order to block their proliferation. Plates were washed twice with PBS, and 100 μL of the T-cell suspension (corresponding to $5 \times 10^4$ T cells) and the fusion polypeptides of SEQ ID NO: 44 and SEQ ID NO: 45 at a concentration of 1 μg/mL, 0.1 μg/mL, 0.01 μg/mL, 0.001 μg/mL were added in the presence or absence of an excess of SEQ ID NO: 10 (1 mg/mL). Plates were covered with a gas permeable seal (4titude) and incubated at 37° C. in a humidified 5% $CO_2$ atmosphere for 3 days. Subsequently, IL-2 concentration in the supernatant was determined by ELISA using the human IL-2 ELISA set by BD Bioscience according to the manufacturer's instructions.

The result of the experiment is depicted in FIGS. 21A-D. For the two fusion polypeptides of SEQ ID NOs: 44 (FIG. 21A) and SEQ ID NO: 45 (FIG. 21C), there is a clear induction of IL-2 production by the employed T-cells which increases with rising concentration. In contrast, IL-2 production induction is abolished in the presence of an excess of SEQ ID NO: 10, which inhibits the binding of the bispecifics SEQ ID NOs: 44 and SEQ ID NOs: 45 to the Hep3B cells. This shows that the fusion polypeptides of the disclosure are capable of co-stimulating T-cell activation in a target-dependent manner.

Notably, the amount of IL-2 induced is higher for SEQ ID NOs: 44 compared to SEQ ID NO: 45, indicating that the geometry of a bispecific GPC3/CD137 fusion plays an important role in determining the strength of T cell activation.

Example 22: Functional T-Cell Activation Assay Tumor Cells with High and Low GPC3 Levels We employed a target-cell dependent T-cell activation assay, similar to the experiment described in Example 20, to assess the ability of the fusion polypeptides of SEQ ID NO: 44 and SEQ ID NO: 45 to co-stimulate T-cell responses in dependence of the GPC3 level of the employed cell line. As a negative control, we employed the HER2-binding antibody trastuzumab. For comparison, we investigated the behavior of reference anti-CD137 monoclonal antibody of SEQ ID NOs: 74 and 75. In the experiment, an anti-human CD3 antibody (OKT3, eBioscience) was coated on plastic culture dishes, and subsequently HepG2, SKBR3 or MCF7 cells were separately cultured on the dishes overnight. The next day, purified T-cells were incubated on the coated surface in the presence of various concentrations of the fusion polypeptide of SEQ ID NO: 44, SEQ ID NO: 45, the reference antibody SEQ ID NOs: 74 and 75, and the negative controls trastuzumab and vehicle (i.e. no addition of test article). As readout, we measured supernatant interleukin 2 (IL-2) levels. In the following, the experiment is described in detail.

Human peripheral blood mononuclear cells (PBMC) from healthy volunteer donors were isolated from buffy coats by centrifugation through a Polysucrose density gradient (Biocoll® 1.077 g/mL from Biochrom), following Biochrom's protocols. The T lymphocytes were isolated from the resulting PBMC using a Pan T-cell purification Kit (Miltenyi Biotec GmbH) and the manufacturer's protocols. Purified T-cells were resuspended in a buffer consisting of 90% FCS and 10% DMSO, immediately frozen down using liquid nitrogen and stored in liquid nitrogen until further use. For the assay, T cells were thawed for 16 h and cultivated in culture media (RPMI 1640, Life Technologies) supplemented with 10% FCS and 1% Penicillin-Streptomycin (Life Technologies).

The following procedure was performed using triplicates for each experimental condition. Flat-bottom tissue culture plates were pre-coated for 1 h at 37° C. using 200 μL of 0.25 μg/mL anti-CD3 antibody. The plates were subsequently washed twice with PBS. $5 \times 10^4$ target tumor cells per well were plated and allowed to adhere overnight at 37° C. in a humidified 5% $CO_2$ atmosphere. The target cells had before been grown in culture under standard conditions, detached using Accutase and resuspended in culture media.

On the next day, tumor cells were treated 2 hours at 37° C. with mitomycin C (Sigma Aldrich) at a concentration of 30 μg/ml in order to block their proliferation. Plates were washed twice with PBS, and 100 μL of the T-cell suspension (corresponding to $5 \times 10^4$ T cells) were added to each well, together with the test articles SEQ ID NO: 44, SEQ ID NO: 45, the reference antibody SEQ ID NOs: 74 and 75, and the negative control trastuzumab, at concentrations ranging from 0.05 nM to 5 nM. Plates were covered with a gas permeable seal (4titude) and incubated at 37° C. in a humidified 5% $CO_2$ atmosphere for 3 days. Subsequently, the IL-2 concentration in the supernatant was assessed as described below.

Human IL-2 levels in the cell culture supernatants were quantified using the IL-2 DuoSet kit from R&D Systems. The procedure is carried out and described in the following. In the first step, a 384 well plate was coated at room temperature for 2 h with 1 μg/mL "Human IL-2 Capture Antibody" (R&D System) diluted in PBS. Subsequently, wells were washed 5 times with 80 μl PBS-T (PBS containing 0.05% Tween20) using a Biotek EL405 select CW washer (Biotek). After 1 h blocking in PBS-T additionally containing 1% casein (w/w), pooled supernatant and a concentration series of an IL-2 standard diluted in culture medium were incubated in the 384-well plate overnight at 4° C. To allow for detection and quantitation of captured IL-2, a mixture of 100 ng/mL biotinylated goat anti-hIL-2-Bio detection antibody (R&D System) and 1 μg/mL Sulfotag-labelled streptavidin (Mesoscale Discovery) were added in PBS-T containing 0.5% casein and incubated at room temperature for 1 h. After washing, 25 μL reading buffer was added to each well and the electrochemiluminescence (ECL) signal of every well was read using a Mesoscale Discovery reader. Analysis and quantification were performed using Mesoscale Discovery software.

The result of a representative experiment is depicted in FIGS. 22A-B. In these Figures, values are plotted relative to the background IL-2 production in the absence of test article, and therefore represent the fold change compared to background. While the negative control trastuzumab (FIG. 22A, triangles) does not lead to IL-2 induction on T-cells with any of the three cell lines, rising concentrations of the bispecific fusion polypeptide SEQ ID NO: 44 (FIG. 22A, circles) and SEQ ID NO: 45 (FIG. 22A, squares) induce T-cells to produce IL-2 in the presence of the GPC3-expressing HepG2 cells. However, no IL-2 increase due to SEQ ID NO: 44 and SEQ ID NO: 45 is apparent for the GPC3 negative SKBR3 and MCF7 cells (FIGS. 22A-B). This behavior is markedly different to the anti-CD137 antibody SEQ ID NOs: 74 and 75, which induces IL-2 on T-cells in the presence of all three cell lines (FIG. 22B).

The experiment clearly demonstrates that SEQ ID NO: 44 and SEQ ID NO: 45 activate T-cells in a manner that is dependent on presence of GPC3 on the target cells. While the GPC3-positive HepG2 cell line shows a clear T-cell activation as measured by IL-2 production, this effect does not occur with SKBR3 and MCF7 cells, which do not express detectable levels of GPC3. That this effect is attributable to the presence of GPC3 and not due to the GPC3 negative cell lines under study potentially rendering CD137 signaling ineffective becomes apparent by the fact that the anti-CD137 antibody SEQ ID NOs: 74 and 75 is capable of activating T cells via CD137 signaling with all three cell types.

Example 23: Ex Vivo T Cell Immunogenicity Assessment of Fusion Polypeptides

To investigate the risk of the formation of anti-drug antibodies in man, an in vitro T cell immunogenicity assessment of the bispecific fusion polypeptides SEQ ID NO: 44 and SEQ ID NO: 45, the control antibody trastuzumab and the positive control keyhole limpet hemocyanine (KLH) was performed. To perform the experiment, PBMC from 32 donors selected to cover HLA allotypes reflective of the distribution in a global population were thawed, washed and seeded onto 96-well plates at a density of $3 \times 10^5$ cells per well. Test articles, diluted in assay media, were added to the cells at a concentration of 30 μg/mL. Assay medium alone was used as a blank, and keyhole limpet hemocyanine (KLH) was used as a nave positive control. PBMC were incubated for 7 days in a humidified atmosphere at 37° C. and 5% $CO_2$. On day 7, PBMCs were labelled for surface phenotypic CD3+ and CD4+ markers and for DNA-incorporated EdU (5-ethynyl-2'deoxyuridine), used as a cell proliferation marker. The percentage of CD3+CD4+EdU+ proliferating cells was measured using a Guava easyCyte 8HT flow cytometer and analyzed using GuavaSoft InCyte software.

FIG. 23 provides the results of this assay for all 32 donors and all test molecules under study. In FIG. 23A, the stimulation index was plotted, which was obtained by the ratio of proliferation in the presence vs. absence of test article. The threshold that defines a responding donor (stimulation index>2) is indicated as a dotted line. In FIG. 23B, the number of responding donors as defined by this threshold was plotted. Evidently, the number of donors responding to the reference trastuzumab lies at one and is therefore small, while all 32 donors respond to the positive control KLH with strong proliferation above the threshold. For the bispecific fusion polypeptides SEQ ID NO: 44 and SEQ ID NO: 45, the number of responding donors also lies at one in both cases.

The experiment therefore demonstrates that the bispecific fusion polypeptides induce little response in the in vitro T cell immunogenicity assessment, which indicates that the risk of inducing immunogenic responses is low.

Example 24: Affinity to Fc-Gamma Receptors hFcγ RI/CD64 and hFcγ RIIIA/CD16a

To measure the binding affinities of polypeptide fusions with an engineered, IgG4-based backbone (SEQ ID NO: 44 and SEQ ID NO: 45) to Fc-gamma receptors hFcγ RI/CD64 (R&D Systems) and hFcγ RIIIA/CD16a (R&D Systems), a surface plasmon resonance (SPR) based assay was employed. Trastuzumab served as a control of a monospecific antibody with an IgG1 backbone. In the SPR affinity assay, polypeptide fusions were biotinylated and captured on a sensor chip CAP using the Biotin CAPture Kit (GE Healthcare). The sensor Chip CAP was pre-immobilized with an ssDNA oligonucleotide. Undiluted Biotin CAPture Reagent (streptavidin conjugated with the complementary ss-DNA oligonucleotide) was applied at a flow rate of 2 μL/min for 300 s. Subsequently, 10 μg/mL of biotinylated polypeptide fusion was applied for 300 s at a flow rate of 5 μL/min. Trastuzumab and the polypeptide fusions were biotinylated by incubation with EZ-Link® NHS-PEG4-Biotin (Thermo Scientific) for two hours at room temperature. The excess of non-reacted biotin reagent was removed by loading the reaction mixture onto a Zeba™ Spin Desalting Plate (Thermo Scientific). The reference channel was loaded with Biotin CAPture Reagent only.

To determine the affinity, four dilutions of hFcγ RI/CD64 (at 100, 25 and 6.25 and 1.6 nM) or four to five dilutions of hFcγ RIIIA/CD16a (at 1000, 333, 111, 37 and 12 nM) were prepared in running buffer (10 mM HEPES, 150 mM NaCl, 0.05% v/v Surfactant P20, 3 mM EDTA, pH 7.4 (GE Healthcare)) and applied to the chip surface. Applying a flow rate of 30 μL/min, the sample contact time was 180 s and dissociation time was 1800/2700 s for hFcγ RI/CD64 or 300 s hFcγ RIIIA/CD16a. All measurements were performed at 25° C. Regeneration of the Sensor Chip CAP surface was achieved with an injection of 6 M Gua-HCl with 0.25 M NaOH followed by an extra wash with running buffer and a stabilization period of 120 s. Prior to the protein measurements three regeneration cycles were performed for conditioning purposes. Data were evaluated with Biacore T200 Evaluation software (V 2.0). Double referencing was used. For hFcγ RI/CD64 the 1:1 binding model was used to fit the raw data. For hFcγ RIIIA/CD16a the Steady State Affinity model was used to fit the raw data.

Table 17 shows the results of the fit of the data for hFcγ RI/CD64. The IgG1-based test article Trastuzumab displayed an affinity of 0.3 nM. The polypeptide fusions SEQ ID NO: 44 and SEQ ID NO: 45 showed no significant binding to hFcγ RI/CD64. These data demonstrate that binding to hFcγ RI/CD64 can be reduced to insignificant levels by switching the isotype from IgG1 to engineered IgG4.

TABLE 17

| Clone name | KD [nM] |
| --- | --- |
| Trastuzumab | 0.3 |
| SEQ ID NO: 44 | not determinable |
| SEQ ID NO: 45 | not determinable |

Table 18 shows the results of the fit of the data for hFcγ RIIIA/CD16a. The resulting binding affinity to hFcγ RIIIA/CD16a of the IgG1-based test articles Trastuzumab was around 350 nM whereas the polypeptide fusions SEQ ID NO: 44 and SEQ ID NO: 45 showed no significant binding to hFcγ RIIIA/CD16a. These data demonstrate that binding to hFcγ RI/CD64 can be reduced to insignificant levels by switching the isotype from IgG1 to engineered IgG4.

TABLE 18

| Name | KD [nM] |
| --- | --- |
| Trastuzumab | 335 ± 64 |
| SEQ ID NO: 44 | not determinable |
| SEQ ID NO: 45 | not determinable |

Example 25: Affinity to Neonatal Fc Receptor

To measure the binding affinities of polypeptide fusions with an engineered, IgG4-based backbone (SEQ ID NO: 44 and SEQ ID NO: 45) to the neonatal Fc receptor (FcRn, Sino Biologicals, #CT009-H08H), a Surface Plasmon Resonance (SPR) based assay was employed. Trastuzumab served as a control of a monospecific antibody with an IgG1 backbone. In the SPR affinity assay, FcRn was covalently immobilized on a CM5 sensor chip (GE Healthcare) according to the manufacturer's instructions. Briefly, after activating the carboxyl groups of the dextran matrix with 1-ethyl-3-(3-dimethylaminopropyl)-carbodiimide (EDC) and N-hydroxysuccinimide (NHS), the primary amines of the FcRn protein were allowed to react with the NHS ester on the surface until a signal of ~200 RU was reached. Finally, non-reacted NHS-esters were blocked by passing a solution of 1M ethanolamine across the surface. The flow rate throughout the immobilization procedure was 10 µl/min.

To determine their affinity, six dilutions (1000 nM, 333 nM, 111 nM, 37 nM, 12 nM and 4 nM) of all constructs were prepared in running buffer (10 mM HEPES, 150 mM NaCl, 0.05% v/v Surfactant P20, 3 mM EDTA, pH 6.0) and applied to the chip surface. Applying a flow rate of 30 µL/min, the sample contact time was 180 s and dissociation time was 30 s. All measurements were performed at 25° C. Regeneration of the Sensor Chip CAP surface was achieved with an injection of 10 mM glycine pH 3.0. Prior to the protein measurements three regeneration cycles are performed for conditioning purposes. Data were evaluated with Biacore T200 Evaluation software (V 2.0) with double referencing. The Steady State Affinity model was used to fit the raw data.

Reflected in Table 19, the resulting binding affinities of all polypeptide fusions to FcRn were around 2 µM which demonstrates that switching the isotype from IgG1 to an engineered IgG4 backbone has no detectable impact on FcRn binding.

TABLE 19

| Name | KD [µM] |
| --- | --- |
| Trastuzumab | 2.0 |
| SEQ ID NO: 44 | 2.1 |
| SEQ ID NO: 45 | 1.9 |

Example 26: Pharmacokinetics of Fusion Polypeptides in Mice

An analysis of the pharmacokinetics of fusion polypeptides defined by SEQ ID NO: 44 and SEQ ID NO: 45 was performed in mice. Male CD-1 mice approximately 5 weeks of age (3 mice per time point; Charles River Laboratories, Research Models and Services, Germany GmbH) were injected into a tail vein with a fusion polypeptide at a dose of 10 mg/kg. The test articles were administered as a bolus using a volume of 5 mL/kg. Plasma samples from the mice were obtained at the time points of 5 min, 1 h, 2 h, 4 h, 8 h, 24 h, 48 h, 4 d, 8 d and 14 d. Sufficient whole blood—taken under isoflurane anesthesia—was collected to obtain at least 100 µL Li-Heparin plasma per animal and time. Drug levels were detected using a Sandwich ELISA detecting the full bispecific construct via the targets GPC3 and CD137. The data were fitted using a two-compartmental model using Prism GraphPad 5 software.

FIG. 25 shows plots of the plasma concentration over time for the constructs SEQ ID NO: 44 and SEQ ID NO: 45, with the insert showing the same data in a semilogarithmic plot. The pharmacokinetics looked similar in both cases. Starting from a plasma concentration of around 150 µg/mL, plasma levels fell to background levels within around 100 hours. The bi-exponential decay of a two-compartmental model was successfully applied to accurately describe the data, and a fit of the data (FIG. 25) using this model resulted in terminal half-lives of 13.7 h for SEQ ID NO: 44 and 10.0 h for SEQ ID NO: 45.

The data demonstrate that the bispecific fusions have half-lives that are in intermediate range of what may be expected for Fc fusion proteins.

Example 27: Pharmacokinetics of Fusion Polypeptides in Cynomolgus Monkey

An analysis of the pharmacokinetics of fusion polypeptides defined by SEQ ID NO: 44 and SEQ ID NO: 45 was performed in cynomolgus monkeys. Male cynomolgus monkeys received an intravenous infusion over 60 minutes, with a dose of 3 mg/kg test article. Plasma samples from the cynomolgus monkeys were obtained at the time points of 15 min, 2 h, 4 h, 8 h, 24 h, 48 h, 3 d, 4 d, 5 d, 6 d, 7 d, 9 d, 11 d, 14 d, 18 d, and 24 d. Drug levels were detected using a Sandwich ELISA detecting the full bispecific construct via the targets HER2 and CD137. Trastuzumab plasma levels were determined using a Sandwich ELISA with targets HER2 and human Fc. The data were fitted using a two-compartmental model using Prism GraphPad 5 software.

FIG. 26 shows plots of the plasma concentration over time for the constructs SEQ ID NO: 44 and SEQ ID NO: 45, with the insert showing the same data in a semi-logarithmic plot. The pharmacokinetics looked similar in both cases, with SEQ ID NO: 44 displaying an apparently longer half-life. Starting from a plasma concentration of around 70 µg/mL, plasma levels fall to levels close to zero over the time course of 200 h. The bi-exponential decay of a two-compartmental model was successfully applied to accurately describe the data, and a fit of the data (FIG. 26) using this model resulted in terminal half-lives of 39 h (SEQ ID NO: 44) and 24.1 h (SEQ ID NO: 45), respectively.

The data therefore demonstrate that the bispecific fusions have terminal half-lives in cynomolgus monkeys that increased compared to the half-life in mice, and in a reasonable range for a biologic therapeutic.

Embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of this invention. All patents, patent applications, textbooks and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and sub-generic groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group. Further embodiments will become apparent from the following claims.

Equivalents: Those skilled in the art will recognize, or be able to ascertain using no more than routine experimentation, many equivalents to the specific embodiments of the invention described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference.

The invention claimed is:

1. A fusion polypeptide that is capable of binding both CD137 and glypican-3 (GPC3), wherein the fusion polypeptide comprises at least two subunits in any order, wherein the first subunit is specific for CD137 and the second subunit is specific for GPC3 and wherein the second subunit comprises an amino acid sequence of a GPC3-specific lipocalin mutein comprising at least one of the following mutated amino acid residues in comparison with the linear polypeptide sequence of mature human lipocalin 2 (hNGAL) (SEQ ID NO: 2):

Leu 36→Val or Arg; Ala 40→Leu, Val or Gly; Ile 41→Leu, Arg, Met, Gly or Ala; Gln 49→Pro or Leu; Tyr 52→Arg or Trp; Asn 65→Asp; Ser 68→Val, Gly, Asn or Ala; Leu 70→Arg, Ser, Ala or Val; Arg 72→Asp, Trp, Ala, or Gly; Lys 73→Gly, Arg, Asn, Glu or Ser; Cys 76→Val or Ile; Asp 77→His, Met, Val, Leu,

Thr or Lys; Trp 79→Lys, Ser or Thr; Arg 81→Gly; Cys 87→Ser; Asn 96→Arg, Asp, Gln or Pro; Tyr 100→Gly, Glu, Pro or Gln; Leu 103→Glu, Gln, Asn, Gly, Ser or Tyr; Ser 105→Ala; Tyr 106→Asn, Ser or Thr; Lys 125→Glu; Ser 127→Arg or Tyr; Tyr 132→Trp or Ile; Lys 134→Ala or Phe; Thr 136→Ile; and Cys 175→Ala.

2. The fusion polypeptide of claim 1, wherein with respect to the amino acid sequence of the GPC3-specific lipocalin mutein, the natural N-glycosylation site Asn at position 65 of the linear polypeptide sequence of mature hNGAL (SEQ ID NO: 2) is removed at the corresponding sequence position of said mutein.

3. The fusion polypeptide of claim 1, wherein the amino acid sequence of the GPC3-specific lipocalin mutein comprises one of the following sets of amino acid substitutions:

(a) Leu 36→Val; Ile 41→Leu; Gln 49→Leu; Tyr 52 Arg; Asn 65→Asp; Ser 68→Val; Leu 70→Ser; Arg 72→Trp; Lys 73→Arg; Asp 77→His; Trp 79→Lys; Arg 81→Gly; Cys 87→Ser; Asn 96→Asp; Tyr 100→Gly; Leu 103→Gln; Tyr 106→Asn; Lys 125→Glu; Ser 127→Arg; Tyr 132→Trp; Lys 134→Ala;

(b) Leu 36→Val; Ala 40→Val; Ile 41→Arg; Gln 49→Pro; Tyr 52 Arg; Asn 65→Asp; Ser 68→Gly; Leu 70→Ser; Lys 73→Gly; Asp 77→His; Trp 79→Lys; Arg 81→Gly; Cys 87→Ser; Asn 96→Asp; Tyr 100→Gly; Leu 103→Glu; Tyr 106→Asn; Lys 125→Glu; Ser 127→Arg; Tyr 132→Trp; Lys 134→Phe;

(c) Leu 36→Val; Ala 40→Gly; Ile 41→Met; Gln 49→Leu; Tyr 52→Arg; Asn 65→Asp; Leu 70→Ala; Lys 73→Asn; Asp 77→His; Trp 79→Lys; Arg 81→Gly; Cys 87→Ser; Asn 96→Gln; Tyr 100→Gly; Leu 103→Glu; Tyr 106→Asn; Lys 125→Glu; Ser 127→Arg; Tyr 132→Trp; Lys 134→Phe;

(d) Leu 36→Arg; Ala 40→Val; Ile 41→Gly; Gln 49→Pro; Tyr 52→Trp; Asn 65→Asp; Ser 68→Asn; Leu 70→Arg; Arg 72→Ala; Lys 73→Arg; Asp 77→Leu; Trp 79→Ser; Arg 81→Gly; Cys 87→Ser; Asn 96→Gln; Tyr 100→Glu; Leu 103→Asn; Ser 105→Ala; Tyr 106→Asn; Lys 125→Glu; Ser 127→Tyr; Tyr 132→Ile; Lys 134→Phe; Thr 136→Ile;

(e) Leu 36→Arg; Ala 40→Val; Ile 41→Gly; Gln 49→Pro; Tyr 52→Trp; Asn 65→Asp; Ser 68→Asn; Leu 70→Arg; Arg 72→Ala; Lys 73→Arg; Asp 77→Thr; Trp 79→Ser; Arg 81→Gly; Cys 87→Ser; Asn 96→Gln; Tyr 100→Glu; Leu 103→Gly; Ser 105→Ala; Tyr 106→Asn; Lys 125→Glu; Ser 127→Tyr; Tyr 132→Ile; Lys 134→Phe; Thr 136→Ile;

(f) Leu 36→Arg; Ala 40→Gly; Ile 41→Ala; Gln 49→Pro; Tyr 52→Trp; Asn 65→Asp; Ser 68→Asn; Leu 70→Arg; Arg 72→Ala; Lys 73→Arg; Asp 77→Val; Trp 79→Ser; Arg 81→Gly; Cys 87→Ser; Asn 96→Pro; Tyr 100→Glu; Leu 103→Asn; Ser 105→Ala; Tyr 106→Ser; Lys 125→Glu; Ser 127→Tyr; Tyr 132→Ile; Lys 134→Phe; Thr 136→Ile;

(g) Leu 36→Arg; Ala 40→Val; Ile 41→Ala; Gln 49→Pro; Tyr 52→Arg; Asn 65→Asp; Ser 68→Ala; Leu 70→Arg; Arg 72→Ala; Lys 73→Arg; Asp 77→Leu; Trp 79→Ser; Arg 81→Gly; Cys 87→Ser; Asn 96→Arg; Tyr 100→Glu; Leu 103→Tyr; Ser 105→Ala; Tyr 106→Asn; Lys 125→Glu; Ser 127→Tyr; Tyr 132→Ile; Lys 134→Phe; Thr 136→Ile;

(h) Leu 36→Arg; Ala 40→Val; Ile 41→Ala; Gln 49→Pro; Tyr 52→Arg; Asn 65→Asp; Ser 68→Asn; Leu 70→Val; Arg 72→Ala; Lys 73→Gly; Asp 77→Lys; Trp 79→Ser; Arg 81→Gly; Cys 87→Ser; Asn 96→Arg; Tyr 100→Pro; Leu 103→Asn; Ser 105→Ala; Tyr 106→Asn; Lys 125→Glu; Ser 127→Tyr; Tyr 132→Ile; Lys 134→Phe; Thr 136→Ile;

(i) Leu 36→Arg; Ala 40→Leu; Ile 41→Gly; Gln 49→Pro; Tyr 52→Trp; Asn 65→Asp; Ser 68→Asn; Leu 70→Arg; Arg 72→Ala; Lys 73→Arg; Asp 77→Met; Trp 79→Ser; Arg 81→Gly; Cys 87→Ser; Asn 96→Gln; Tyr 100→Glu; Leu 103→Ser; Ser 105→Ala; Tyr 106→Asn; Lys 125→Glu; Ser 127→Tyr; Tyr 132→Ile; Lys 134→Phe;

(j) Leu 36→Arg; Ala 40→Val; Ile 41→Gly; Gln 49→Pro; Tyr 52→Trp; Asn 65→Asp; Ser 68→Asn; Leu 70→Arg; Arg 72→Ala; Lys 73→Gly; Cys 76→Val; Asp 77→Lys; Trp 79→Thr; Arg 81→Gly; Cys 87→Ser; Asn 96→Gln; Tyr 100→Glu; Leu 103→Asn; Ser 105→Ala; Tyr 106→Thr; Lys 125→Glu; Ser 127→Tyr; Tyr 132→Ile; Lys 134→Phe; Cys 175→Ala;

(k) Leu 36→Arg; Ala 40→Val; Ile 41→Gly; Gln 49→Pro; Tyr 52→Arg; Asn 65→Asp; Ser 68→Gly; Leu 70→Arg; Arg 72→Gly; Lys 73→Glu; Cys 76→Ile; Asp 77→Lys; Trp 79→Ser; Arg 81→Gly; Cys 87→Ser; Asn 96→Gln; Tyr 100→Gln; Leu 103→Asp; Ser 105→Ala; Tyr 106→Thr; Lys 125→Glu; Ser 127→Tyr; Tyr 132→Ile; Lys 134→Phe; Thr 136→Ile; Cys 175→Ala; and (l) Leu 36→Arg; Ala 40→Val; Ile 41→Gly; Gln 49→Pro; Tyr 52→Arg; Asn 65→Asp; Ser 68→Gly; Leu 70→Arg; Arg 72→Asp; Lys 73→Ser; Cys 76→Val; Asp 77→Thr; Trp 79→Ser; Arg 81→Gly; Cys 87→Ser; Asn 96→Gln; Tyr 100→Glu; Leu 103→Asn; Ser 105→Ala; Tyr 106→Thr; Lys 125→Glu; Ser 127→Tyr; Tyr 132→Ile; Lys 134→Phe; Thr 136→Ile; Cys 175→Ala.

4. The fusion polypeptide of claim 1, wherein the GPC3-specific lipocalin mutein does not have an N-glycosylation site.

5. The fusion polypeptide of claim 1, wherein the GPC3-specific lipocalin mutein comprises an amino acid sequence selected from the group consisting of SEQ ID NOs: 4-17.

6. The fusion polypeptide of claim 1, wherein the fusion polypeptide comprises the amino acid sequences shown in SEQ ID NOs: 36 and 37, or the amino acid sequences shown in SEQ ID NOs: 38 and 39, or the amino acid sequences shown in SEQ ID NOs: 40 and 41, or the amino acid sequences shown in SEQ ID NOs: 42 and 43, the amino acid sequence shown in SEQ ID NO: 44, the amino acid sequence shown in SEQ ID NO: 45, the amino acid sequence shown in SEQ ID NO: 46, the amino acid sequences shown in SEQ ID NO: 47, or the amino acid sequences shown in SEQ ID NOs: 53 and 54.

* * * * *

SEQUENCE LISTING

```
<160> NUMBER OF SEQ ID NOS: 75

<210> SEQ ID NO 1
<211> LENGTH: 156
<212> TYPE: PRT
<213> ORGANISM: artificial
<220> FEATURE:
<223> OTHER INFORMATION: wildtype Tlc

<400> SEQUENCE: 1

His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
            20                  25                  30

Leu Glu Ser Val Thr Pro Met Thr Leu Thr Thr Leu Glu Gly Gly Asn
        35                  40                  45

Leu Glu Ala Lys Val Thr Met Leu Ile Ser Gly Arg Cys Gln Glu Val
    50                  55                  60

Lys Ala Val Leu Glu Lys Thr Asp Glu Pro Gly Lys Tyr Thr Ala Asp
65                  70                  75                  80

Gly Gly Lys His Val Ala Tyr Ile Ile Arg Ser His Val Lys Asp His
                85                  90                  95

Tyr Ile Phe Tyr Cys Glu Gly Glu Leu His Gly Lys Pro Val Arg Gly
            100                 105                 110

Val Lys Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly
145                 150                 155

<210> SEQ ID NO 2
```

```
<211> LENGTH: 178
<212> TYPE: PRT
<213> ORGANISM: artificial
<220> FEATURE:
<223> OTHER INFORMATION: Wildtype NGAL

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 3
<211> LENGTH: 178
<212> TYPE: PRT
<213> ORGANISM: artificial
<220> FEATURE:
<223> OTHER INFORMATION: NGAL98 control

<400> SEQUENCE: 3

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140
```

```
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 4
<211> LENGTH: 178
<212> TYPE: PRT
<213> ORGANISM: artificial
<220> FEATURE:
<223> OTHER INFORMATION: Lipocalin mutein

<400> SEQUENCE: 4

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Ala Met Leu Arg Glu Asp Lys Asp Pro
            35                  40                  45

Leu Lys Met Arg Ala Thr Ile Tyr Glu Leu Lys Glu Asp Lys Ser Tyr
    50                  55                  60

Asn Val Thr Gly Val Ser Phe Trp Arg Lys Lys Cys His Tyr Lys Ile
65                  70                  75                  80

Gly Thr Phe Val Pro Gly Ser Gln Pro Gly Glu Phe Thr Leu Gly Asp
                85                  90                  95

Ile Lys Ser Gly Pro Gly Gln Thr Ser Asn Leu Val Arg Val Val Ser
            100                 105                 110

Thr Asn Tyr Asn Gln His Ala Met Val Phe Phe Lys Glu Val Arg Gln
        115                 120                 125

Asn Arg Glu Trp Phe Ala Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 5
<211> LENGTH: 178
<212> TYPE: PRT
<213> ORGANISM: artificial
<220> FEATURE:
<223> OTHER INFORMATION: Lipocalin mutein

<400> SEQUENCE: 5

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Arg Ala Gly Asn Val Ala Leu Arg Glu Asp Lys Asp Pro
            35                  40                  45

Pro Lys Met Arg Ala Thr Ile Tyr Glu Leu Lys Glu Asp Lys Ser Tyr
    50                  55                  60

Asn Val Thr Asn Val Arg Phe Ala Met Lys Lys Cys Met Tyr Ser Ile
65                  70                  75                  80
```

```
Gly Thr Phe Val Pro Gly Ser Gln Pro Gly Glu Phe Thr Leu Gly Gln
                85                  90                  95

Ile Lys Ser Glu Pro Gly Asn Thr Ser Asn Leu Val Arg Val Val Ser
            100                 105                 110

Thr Asn Tyr Asn Gln His Ala Met Val Phe Phe Lys Glu Val Tyr Gln
            115                 120                 125

Asn Arg Glu Ile Phe Phe Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 6
<211> LENGTH: 178
<212> TYPE: PRT
<213> ORGANISM: artificial
<220> FEATURE:
<223> OTHER INFORMATION: Lipocalin mutein

<400> SEQUENCE: 6

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Val Ala Gly Asn Ala Leu Leu Arg Glu Asp Lys Asp Pro
            35                  40                  45

Leu Lys Met Arg Ala Thr Ile Tyr Glu Leu Lys Glu Asp Lys Ser Tyr
        50                  55                  60

Asp Val Thr Val Val Ser Phe Trp Arg Lys Lys Cys His Tyr Lys Ile
65                  70                  75                  80

Gly Thr Phe Val Pro Gly Ser Gln Pro Gly Glu Phe Thr Leu Gly Asp
                85                  90                  95

Ile Lys Ser Gly Pro Gly Gln Thr Ser Asn Leu Val Arg Val Val Ser
            100                 105                 110

Thr Asn Tyr Asn Gln His Ala Met Val Phe Phe Lys Glu Val Arg Gln
            115                 120                 125

Asn Arg Glu Trp Phe Ala Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 7
<211> LENGTH: 178
<212> TYPE: PRT
<213> ORGANISM: artificial
<220> FEATURE:
<223> OTHER INFORMATION: Lipocalin mutein

<400> SEQUENCE: 7

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
```

```
            20                  25                  30
Val Val Gly Val Ala Gly Asn Val Arg Leu Arg Glu Asp Lys Asp Pro
            35                  40                  45

Pro Lys Met Arg Ala Thr Ile Tyr Glu Leu Lys Glu Asp Lys Ser Tyr
 50                  55                  60

Asp Val Thr Gly Val Ser Phe Arg Gly Lys Lys Cys His Tyr Lys Ile
 65                  70                  75                  80

Gly Thr Phe Val Pro Gly Ser Gln Pro Gly Glu Phe Thr Leu Gly Asp
                 85                  90                  95

Ile Lys Ser Gly Pro Gly Glu Thr Ser Asn Leu Val Arg Val Val Ser
                100                 105                 110

Thr Asn Tyr Asn Gln His Ala Met Val Phe Phe Lys Glu Val Arg Gln
                115                 120                 125

Asn Arg Glu Trp Phe Phe Ile Thr Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 8
<211> LENGTH: 178
<212> TYPE: PRT
<213> ORGANISM: artificial
<220> FEATURE:
<223> OTHER INFORMATION: Lipocalin mutein

<400> SEQUENCE: 8

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                 20                  25                  30

Val Val Gly Val Ala Gly Asn Gly Met Leu Arg Glu Asp Lys Asp Pro
            35                  40                  45

Leu Lys Met Arg Ala Thr Ile Tyr Glu Leu Lys Glu Asp Lys Ser Tyr
 50                  55                  60

Asp Val Thr Ser Val Ala Phe Arg Asn Lys Lys Cys His Tyr Lys Ile
 65                  70                  75                  80

Gly Thr Phe Val Pro Gly Ser Gln Pro Gly Glu Phe Thr Leu Gly Gln
                 85                  90                  95

Ile Lys Ser Gly Pro Gly Glu Thr Ser Asn Leu Val Arg Val Val Ser
                100                 105                 110

Thr Asn Tyr Asn Gln His Ala Met Val Phe Phe Lys Glu Val Arg Gln
                115                 120                 125

Asn Arg Glu Trp Phe Phe Ile Thr Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 9
<211> LENGTH: 178
```

```
<212> TYPE: PRT
<213> ORGANISM: artificial
<220> FEATURE:
<223> OTHER INFORMATION: Lipocalin mutein

<400> SEQUENCE: 9

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Val Gly Leu Arg Glu Asp Lys Asp Pro
        35                  40                  45

Pro Lys Met Trp Ala Thr Ile Tyr Glu Leu Lys Glu Asp Lys Ser Tyr
    50                  55                  60

Asp Val Thr Asn Val Arg Phe Ala Arg Lys Lys Cys Leu Tyr Ser Ile
65                  70                  75                  80

Gly Thr Phe Val Pro Gly Ser Gln Pro Gly Glu Phe Thr Leu Gly Gln
                85                  90                  95

Ile Lys Ser Glu Pro Gly Asn Thr Ala Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Ile Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 10
<211> LENGTH: 178
<212> TYPE: PRT
<213> ORGANISM: artificial
<220> FEATURE:
<223> OTHER INFORMATION: Lipocalin mutein

<400> SEQUENCE: 10

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Val Gly Leu Arg Glu Asp Lys Asp Pro
        35                  40                  45

Pro Lys Met Trp Ala Thr Ile Tyr Glu Leu Lys Glu Asp Lys Ser Tyr
    50                  55                  60

Asp Val Thr Asn Val Arg Phe Ala Arg Lys Lys Cys Thr Tyr Ser Ile
65                  70                  75                  80

Gly Thr Phe Val Pro Gly Ser Gln Pro Gly Glu Phe Thr Leu Gly Gln
                85                  90                  95

Ile Lys Ser Glu Pro Gly Gly Thr Ala Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Ile Leu Tyr Gly Arg Thr Lys Glu Leu
    130                 135                 140
```

-continued

```
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 11
<211> LENGTH: 178
<212> TYPE: PRT
<213> ORGANISM: artificial
<220> FEATURE:
<223> OTHER INFORMATION: Lipocalin mutein

<400> SEQUENCE: 11

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Arg Ala Gly Asn Gly Ala Leu Arg Glu Asp Lys Asp Pro
            35                  40                  45

Pro Lys Met Trp Ala Thr Ile Tyr Glu Leu Lys Glu Asp Lys Ser Tyr
        50                  55                  60

Asp Val Thr Asn Val Arg Phe Ala Arg Lys Lys Cys Val Tyr Ser Ile
65                  70                  75                  80

Gly Thr Phe Val Pro Gly Ser Gln Pro Gly Glu Phe Thr Leu Gly Pro
                85                  90                  95

Ile Lys Ser Glu Pro Gly Asn Thr Ala Ser Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Ile Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 12
<211> LENGTH: 178
<212> TYPE: PRT
<213> ORGANISM: artificial
<220> FEATURE:
<223> OTHER INFORMATION: Lipocalin mutein

<400> SEQUENCE: 12

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Arg Ala Gly Asn Val Ala Leu Arg Glu Asp Lys Asp Pro
            35                  40                  45

Pro Lys Met Arg Ala Thr Ile Tyr Glu Leu Lys Glu Asp Lys Ser Tyr
        50                  55                  60

Asp Val Thr Ala Val Arg Phe Ala Arg Lys Lys Cys Leu Tyr Ser Ile
65                  70                  75                  80

Gly Thr Phe Val Pro Gly Ser Gln Pro Gly Glu Phe Thr Leu Gly Arg
```

```
                85                  90                  95
Ile Lys Ser Glu Pro Gly Tyr Thr Ala Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Ile Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 13
<211> LENGTH: 178
<212> TYPE: PRT
<213> ORGANISM: artificial
<220> FEATURE:
<223> OTHER INFORMATION: Lipocalin mutein

<400> SEQUENCE: 13

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Val Ala Leu Arg Glu Asp Lys Asp Pro
        35                  40                  45

Pro Lys Met Arg Ala Thr Ile Tyr Glu Leu Lys Glu Asp Lys Ser Tyr
    50                  55                  60

Asp Val Thr Asn Val Val Phe Ala Gly Lys Lys Cys Lys Tyr Ser Ile
65                  70                  75                  80

Gly Thr Phe Val Pro Gly Ser Gln Pro Gly Glu Phe Thr Leu Gly Arg
                85                  90                  95

Ile Lys Ser Pro Pro Gly Asn Thr Ala Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Ile Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 14
<211> LENGTH: 178
<212> TYPE: PRT
<213> ORGANISM: artificial
<220> FEATURE:
<223> OTHER INFORMATION: Lipocalin mutein

<400> SEQUENCE: 14

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30
```

-continued

```
Val Val Gly Arg Ala Gly Asn Leu Gly Leu Arg Glu Asp Lys Asp Pro
            35                  40                  45

Pro Lys Met Trp Ala Thr Ile Tyr Glu Leu Lys Glu Asp Lys Ser Tyr
 50                  55                  60

Asp Val Thr Asn Val Arg Phe Ala Arg Lys Lys Cys Met Tyr Ser Ile
 65                  70                  75                  80

Gly Thr Phe Val Pro Gly Ser Gln Pro Gly Glu Phe Thr Leu Gly Gln
                 85                  90                  95

Ile Lys Ser Glu Pro Gly Ser Thr Ala Asn Leu Val Arg Val Val Ser
            100                 105                 110

Thr Asn Tyr Asn Gln His Ala Met Val Phe Phe Lys Glu Val Tyr Gln
            115                 120                 125

Asn Arg Glu Ile Phe Phe Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 15
<211> LENGTH: 178
<212> TYPE: PRT
<213> ORGANISM: artificial
<220> FEATURE:
<223> OTHER INFORMATION: Lipocalin mutein

<400> SEQUENCE: 15

Gln Asp Ser Thr Ser Asp Leu Ile Pro Ala Pro Pro Leu Ser Lys Val
 1                   5                  10                  15

Pro Leu Gln Gln Asn Phe Gln Asp Asn Gln Phe Gln Gly Lys Trp Tyr
                 20                  25                  30

Val Val Gly Arg Ala Gly Asn Val Gly Leu Arg Glu Asp Lys Asp Pro
            35                  40                  45

Pro Lys Met Trp Ala Thr Ile Tyr Glu Leu Lys Glu Asp Lys Ser Tyr
 50                  55                  60

Asp Val Thr Asn Val Arg Phe Ala Gly Lys Lys Val Lys Tyr Thr Ile
 65                  70                  75                  80

Gly Thr Phe Val Pro Gly Ser Gln Pro Gly Glu Phe Thr Leu Gly Gln
                 85                  90                  95

Ile Lys Ser Glu Pro Gly Asn Thr Ala Thr Leu Val Arg Val Val Ser
            100                 105                 110

Thr Asn Tyr Asn Gln His Ala Met Val Phe Phe Lys Glu Val Tyr Gln
            115                 120                 125

Asn Arg Glu Ile Phe Phe Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ala Ile
                165                 170                 175

Asp Gly

<210> SEQ ID NO 16
<211> LENGTH: 178
<212> TYPE: PRT
```

```
<213> ORGANISM: artificial
<220> FEATURE:
<223> OTHER INFORMATION: Lipocalin mutein

<400> SEQUENCE: 16

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Val Gly Leu Arg Glu Asp Lys Asp Pro
        35                  40                  45

Pro Lys Met Arg Ala Thr Ile Tyr Glu Leu Lys Glu Asp Lys Ser Tyr
    50                  55                  60

Asp Val Thr Gly Val Arg Phe Gly Glu Lys Lys Ile Lys Tyr Ser Ile
65                  70                  75                  80

Gly Thr Phe Val Pro Gly Ser Gln Pro Gly Glu Phe Thr Leu Gly Gln
                85                  90                  95

Ile Lys Ser Gln Pro Gly Asp Thr Ala Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Ile Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Ala Ile
                165                 170                 175

Asp Gly

<210> SEQ ID NO 17
<211> LENGTH: 178
<212> TYPE: PRT
<213> ORGANISM: artificial
<220> FEATURE:
<223> OTHER INFORMATION: Lipocalin mutein

<400> SEQUENCE: 17

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Val Gly Leu Arg Glu Asp Lys Asp Pro
        35                  40                  45

Pro Lys Met Arg Ala Thr Ile Tyr Glu Leu Lys Glu Asp Lys Ser Tyr
    50                  55                  60

Asp Val Thr Gly Val Arg Phe Asp Ser Lys Lys Val Thr Tyr Ser Ile
65                  70                  75                  80

Gly Thr Phe Val Pro Gly Ser Gln Pro Gly Glu Phe Thr Leu Gly Gln
                85                  90                  95

Ile Lys Ser Glu Pro Gly Asn Thr Ala Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Ile Leu Tyr Gly Arg Thr Lys Glu Leu
    130                 135                 140

Thr Ser Glu Leu Lys Glu Asn Phe Ile Arg Phe Ser Lys Ser Leu Gly
```

-continued

```
            145                 150                 155                 160
Leu Pro Glu Asn His Ile Val Phe Pro Val Pro Ile Asp Gln Ala Ile
                165                 170                 175
Asp Gly

<210> SEQ ID NO 18
<211> LENGTH: 152
<212> TYPE: PRT
<213> ORGANISM: artificial
<220> FEATURE:
<223> OTHER INFORMATION: lipocalin mutein

<400> SEQUENCE: 18

Ala Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
                20                  25                  30

Thr Pro Met Thr Leu Thr Thr Leu Glu Gly Gly Asn Leu Glu Ala Lys
            35                  40                  45

Val Thr Met Ala Ile Asp Gly Pro Ala Gln Glu Val Lys Ala Val Leu
        50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Val Cys Asp Gly Ser Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 19
<211> LENGTH: 152
<212> TYPE: PRT
<213> ORGANISM: artificial
<220> FEATURE:
<223> OTHER INFORMATION: lipocalin mutein

<400> SEQUENCE: 19

Thr Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
                20                  25                  30

Thr Pro Met Thr Leu Thr Thr Leu Glu Gly Gly Asn Leu Glu Ala Lys
            35                  40                  45

Val Thr Met Ala Ile Asp Gly Pro Ala Gln Glu Val Arg Ala Val Leu
        50                  55                  60

Glu Lys Thr Asp Glu Pro Gly Lys Tyr Thr Ala Asp Gly Gly Lys His
65                  70                  75                  80

Asp Ala Tyr Ile Ile Arg Ser His Val Lys Asp His Tyr Ile Phe Tyr
                85                  90                  95

Ser Glu Gly Val Cys Asp Gly Ser Pro Val Pro Gly Val Trp Leu Val
            100                 105                 110

Gly Arg Asp Pro Glu Asn Asn Leu Glu Ala Leu Glu Asp Phe Glu Lys
```

```
                   115                 120                 125
Thr Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 20
<211> LENGTH: 152
<212> TYPE: PRT
<213> ORGANISM: artificial
<220> FEATURE:
<223> OTHER INFORMATION: lipocalin mutein

<400> SEQUENCE: 20

Ala Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
            20                  25                  30

Thr Pro Met Thr Leu Thr Leu Glu Gly Gly Asn Leu Glu Ala Lys
        35                  40                  45

Val Thr Met Ala Ile Asp Gly Pro Ala Gln Glu Val Asn Ala Val Leu
    50                  55                  60

Glu Lys Thr Asp Glu Pro Gly Lys Tyr Thr Ala Asp Gly Lys His
65                  70                  75                  80

Val Ala Tyr Ile Ile Arg Ser His Val Arg Asp His Tyr Ile Phe Tyr
                85                  90                  95

Ser Glu Gly Val Cys Asp Gly Ser Pro Val Pro Gly Val Trp Leu Val
            100                 105                 110

Gly Arg Asp Pro Glu Asn Asn Leu Glu Ala Leu Glu Asp Phe Glu Lys
        115                 120                 125

Thr Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 21
<211> LENGTH: 152
<212> TYPE: PRT
<213> ORGANISM: artificial
<220> FEATURE:
<223> OTHER INFORMATION: lipocalin mutein

<400> SEQUENCE: 21

Val Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
            20                  25                  30

Thr Pro Met Thr Leu Thr Leu Glu Gly Gly Asn Leu Glu Ala Lys
        35                  40                  45

Val Thr Met Ala Ile Asp Gly Pro Ala Gln Glu Val Arg Ala Val Leu
    50                  55                  60

Glu Lys Thr Asp Glu Pro Gly Lys Tyr Thr Ala Asp Gly Lys His
65                  70                  75                  80

Val Ala Tyr Ile Ile Arg Ser His Val Glu Asp His Tyr Ile Phe Tyr
                85                  90                  95

Ser Glu Gly Val Cys Asp Gly Ser Pro Val Pro Gly Val Trp Leu Val
            100                 105                 110
```

Gly Arg Asp Pro Glu Asn Asn Leu Glu Ala Leu Glu Asp Phe Glu Lys
            115                 120                 125

Thr Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 22
<211> LENGTH: 152
<212> TYPE: PRT
<213> ORGANISM: artificial
<220> FEATURE:
<223> OTHER INFORMATION: lipocalin mutein

<400> SEQUENCE: 22

Ala Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
            20                  25                  30

Thr Pro Met Thr Leu Ser Thr Leu Glu Gly Gly Asn Leu Glu Ala Lys
        35                  40                  45

Val Thr Met Ala Ile Asp Gly Pro Ala Gln Glu Val Lys Ala Val Leu
 50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Val Cys Asp Gly Ser Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
    130                 135                 140

Gln Ile Glu Thr Ser Ser Pro Gly
145                 150

<210> SEQ ID NO 23
<211> LENGTH: 152
<212> TYPE: PRT
<213> ORGANISM: artificial
<220> FEATURE:
<223> OTHER INFORMATION: lipocalin mutein

<400> SEQUENCE: 23

Ala Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
            20                  25                  30

Thr Pro Met Thr Leu Thr Thr Leu Glu Gly Gly Asn Leu Glu Ala Glu
        35                  40                  45

Val Thr Met Ala Ile Asp Gly Pro Ala Gln Glu Val Lys Ala Val Leu
 50                  55                  60

Glu Lys Ala Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Val Cys Asp Gly Ser Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Thr Ala Gly Ala Arg Gly Leu Ser Thr Glu Ser Ile Leu Ile Pro Ser
        130                 135                 140

Gln Ile Glu Thr Ser Ser Pro Gly
145                 150

<210> SEQ ID NO 24
<211> LENGTH: 152
<212> TYPE: PRT
<213> ORGANISM: artificial
<220> FEATURE:
<223> OTHER INFORMATION: lipocalin mutein

<400> SEQUENCE: 24

Thr Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
            20                  25                  30

Thr Pro Met Thr Leu Thr Thr Leu Glu Asp Gly Asn Leu Glu Ala Lys
        35                  40                  45

Val Thr Met Ala Ile Asp Gly Pro Ala Gln Glu Val Lys Ala Val Leu
    50                  55                  60

Glu Lys Ala Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Val Cys Asp Gly Ser Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ile Glu Thr Ser Ser Pro Gly
145                 150

<210> SEQ ID NO 25
<211> LENGTH: 178
<212> TYPE: PRT
<213> ORGANISM: artificial
<220> FEATURE:
<223> OTHER INFORMATION: lipocalin mutein

<400> SEQUENCE: 25

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
        35                  40                  45

Asn Lys Met Met Ala Thr Ile Tyr Glu Leu Lys Glu Asp Lys Ser Tyr
    50                  55                  60

Asn Val Thr Gly Val Thr Phe Asp Asp Lys Lys Cys Thr Tyr Ala Ile
65                  70                  75                  80

Ser Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser

```
                100                 105                 110
Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 26
<211> LENGTH: 178
<212> TYPE: PRT
<213> ORGANISM: artificial
<220> FEATURE:
<223> OTHER INFORMATION: lipocalin mutein

<400> SEQUENCE: 26

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
        35                  40                  45

Ile Lys Met Met Ala Thr Ile Tyr Glu Leu Lys Glu Asp Lys Ser Tyr
    50                  55                  60

Asp Val Thr Met Val Lys Phe Asp Lys Lys Cys Met Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 27
<211> LENGTH: 178
<212> TYPE: PRT
<213> ORGANISM: artificial
<220> FEATURE:
<223> OTHER INFORMATION: lipocalin mutein

<400> SEQUENCE: 27

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
        35                  40                  45
```

Asn Lys Met Met Ala Thr Ile Tyr Glu Leu Lys Glu Asp Lys Ser Tyr
            50                  55                  60

Asp Val Thr Ala Val Ala Phe Asp Asp Lys Lys Cys Thr Tyr Asp Ile
65                  70                  75                  80

Trp Thr Phe Val Pro Gly Ser Gln Pro Gly Glu Phe Thr Leu Gly Lys
                    85                  90                  95

Ile Lys Ser Phe Pro Gly His Thr Ser Ser Leu Val Arg Val Val Ser
                    100                 105                 110

Thr Asn Tyr Asn Gln His Ala Met Val Phe Phe Lys Phe Val Phe Gln
                    115                 120                 125

Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 28
<211> LENGTH: 178
<212> TYPE: PRT
<213> ORGANISM: artificial
<220> FEATURE:
<223> OTHER INFORMATION: lipocalin muein

<400> SEQUENCE: 28

Gln Asp Ser Thr Ser Asp Leu Ile Pro Ala Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Ile Lys Leu Arg Glu Asp Lys Asp Pro
            35                  40                  45

Asn Lys Met Met Ala Thr Ile Tyr Glu Leu Lys Glu Asp Lys Ser Tyr
            50                  55                  60

Asp Val Thr Ala Val Ala Phe Asp Asp Lys Lys Cys Thr Tyr Asp Ile
65                  70                  75                  80

Trp Thr Phe Val Pro Gly Ser Gln Pro Gly Glu Phe Thr Leu Gly Lys
                    85                  90                  95

Ile Lys Ser Phe Pro Gly His Thr Ser Ser Leu Val Arg Val Val Ser
                    100                 105                 110

Thr Asn Tyr Asn Gln His Ala Met Val Phe Phe Lys Phe Val Phe Gln
                    115                 120                 125

Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 29
<211> LENGTH: 175
<212> TYPE: PRT
<213> ORGANISM: artificial
<220> FEATURE:
<223> OTHER INFORMATION: lipocalin mutein

<400> SEQUENCE: 29

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Gln Ala Gly Asn Ile Lys Leu Arg Glu Asp Ser Lys Met
        35                  40                  45
Met Ala Thr Ile Tyr Glu Leu Lys Glu Asp Lys Ser Tyr Asp Val Thr
50                  55                  60
Gly Val Ser Phe Asp Asp Lys Lys Cys Thr Tyr Ala Ile Met Thr Phe
65                  70                  75                  80
Val Pro Gly Ser Gln Pro Gly Glu Phe Thr Leu Gly Lys Ile Lys Ser
            85                  90                  95
Phe Pro Gly His Thr Ser Ser Leu Val Arg Val Ser Thr Asn Tyr
            100                 105                 110
Asn Gln His Ala Met Val Phe Phe Lys Phe Val Phe Gln Asn Arg Glu
            115                 120                 125
Glu Phe Tyr Ile Thr Leu Tyr Gly Arg Thr Lys Glu Leu Thr Ser Glu
    130                 135                 140
Leu Lys Glu Asn Phe Ile Arg Phe Ser Lys Ser Leu Gly Leu Pro Glu
145                 150                 155                 160
Asn His Ile Val Phe Pro Val Pro Ile Asp Gln Cys Ile Asp Gly
                165                 170                 175
```

<210> SEQ ID NO 30
<211> LENGTH: 178
<212> TYPE: PRT
<213> ORGANISM: artificial
<220> FEATURE:
<223> OTHER INFORMATION: lipocalin mutein

<400> SEQUENCE: 30

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Gln Ala Gly Asn Ile Lys Leu Arg Glu Asp Lys Asp Pro
        35                  40                  45
Val Lys Met Met Ala Thr Ile Tyr Glu Leu Lys Glu Asp Lys Ser Tyr
50                  55                  60
Asp Val Thr Gly Val Thr Phe Asp Asp Lys Lys Cys Arg Tyr Asp Ile
65                  70                  75                  80
Ser Thr Phe Val Pro Gly Ser Gln Pro Gly Glu Phe Thr Phe Gly Lys
            85                  90                  95
Ile Lys Ser Phe Pro Gly His Thr Ser Ser Leu Val Arg Val Val Ser
            100                 105                 110
Thr Asn Tyr Asn Gln His Ala Met Val Phe Phe Lys Phe Val Phe Gln
            115                 120                 125
Asn Arg Glu Glu Phe Tyr Ile Thr Leu Tyr Gly Arg Thr Lys Glu Leu
    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
```

Asp Gly

<210> SEQ ID NO 31
<211> LENGTH: 178
<212> TYPE: PRT
<213> ORGANISM: artificial
<220> FEATURE:
<223> OTHER INFORMATION: lipocalin mutein

<400> SEQUENCE: 31

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Gln Ala Gly Asn Ile Arg Leu Arg Glu Asp Lys Asp Pro
        35                  40                  45
His Lys Met Met Ala Thr Ile Tyr Glu Leu Lys Glu Asp Lys Ser Tyr
    50                  55                  60
Asp Val Thr Gly Val Thr Phe Asp Asp Lys Lys Cys Thr Tyr Ala Ile
65                  70                  75                  80
Ser Thr Phe Val Pro Gly Ser Gln Pro Gly Glu Phe Thr Leu Gly Lys
                85                  90                  95
Ile Lys Ser Phe Pro Gly His Thr Ser Ser Leu Val Arg Val Val Ser
            100                 105                 110
Thr Asn Tyr Asn Gln His Ala Met Val Phe Phe Lys Phe Val Phe Gln
        115                 120                 125
Asn Arg Glu Glu Phe Tyr Ile Thr Leu Tyr Gly Arg Thr Lys Glu Leu
    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 32
<211> LENGTH: 178
<212> TYPE: PRT
<213> ORGANISM: artificial
<220> FEATURE:
<223> OTHER INFORMATION: lipocalin mutein

<400> SEQUENCE: 32

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Gln Ala Gly Asn Ile Lys Leu Arg Glu Asp Lys Asp Pro
        35                  40                  45
Asn Lys Met Met Ala Thr Ile Tyr Glu Leu Lys Glu Asp Lys Ser Tyr
    50                  55                  60
Asp Val Thr Gly Val Thr Phe Asp Asp Lys Lys Cys Thr Tyr Ala Ile
65                  70                  75                  80
Ser Thr Leu Val Pro Gly Ser Gln Pro Gly Glu Phe Thr Phe Gly Lys
                85                  90                  95
Ile Lys Ser Phe Pro Gly His Thr Ser Ser Leu Val Arg Val Val Ser
            100                 105                 110
Thr Asn Tyr Asn Gln His Ala Met Val Phe Phe Lys Phe Val Phe Gln
```

115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 33
<211> LENGTH: 178
<212> TYPE: PRT
<213> ORGANISM: artificial
<220> FEATURE:
<223> OTHER INFORMATION: lipocalin mutein

<400> SEQUENCE: 33

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Ile Arg Leu Arg Glu Asp Lys Asp Pro
            35                  40                  45

Ser Lys Met Met Ala Thr Ile Tyr Glu Leu Lys Glu Asp Lys Ser Tyr
50                  55                  60

Asp Val Thr Ala Val Thr Phe Asp Asp Lys Lys Cys Asn Tyr Ala Ile
65                  70                  75                  80

Ser Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 34
<211> LENGTH: 448
<212> TYPE: PRT
<213> ORGANISM: artificial
<220> FEATURE:
<223> OTHER INFORMATION: antibody heavy chain

<400> SEQUENCE: 34

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Ser Pro Glu Lys Gly Leu Glu Trp Ile
            35                  40                  45

Gly Glu Ile Asn His Gly Gly Tyr Val Thr Tyr Asn Pro Ser Leu Glu
50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
             85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 35
<211> LENGTH: 216
<212> TYPE: PRT
<213> ORGANISM: artificial
<220> FEATURE:

<223> OTHER INFORMATION: antibody polypeptide chain

<400> SEQUENCE: 35

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 36
<211> LENGTH: 641
<212> TYPE: PRT
<213> ORGANISM: artificial
<220> FEATURE:
<223> OTHER INFORMATION: fusion polypeptide heavy chain

<400> SEQUENCE: 36

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

```
Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
        435                 440                 445

Gly Gly Gly Gly Ser Gly Gly Gly Ser Gly Gly Gly Gly Ser Gln
450                 455                 460

Asp Ser Thr Ser Asp Leu Ile Pro Ala Pro Pro Leu Ser Lys Val Pro
465                 470                 475                 480

Leu Gln Gln Asn Phe Gln Asp Asn Gln Phe Gln Gly Lys Trp Tyr Val
                485                 490                 495

Val Gly Arg Ala Gly Asn Val Gly Leu Arg Glu Asp Lys Asp Pro Pro
                500                 505                 510

Lys Met Trp Ala Thr Ile Tyr Glu Leu Lys Glu Asp Lys Ser Tyr Asp
    515                 520                 525

Val Thr Asn Val Arg Phe Ala Arg Lys Lys Cys Thr Tyr Ser Ile Gly
530                 535                 540
```

-continued

```
Thr Phe Val Pro Gly Ser Gln Pro Gly Glu Phe Thr Leu Gly Gln Ile
545                 550                 555                 560

Lys Ser Glu Pro Gly Gly Thr Ala Asn Leu Val Arg Val Val Ser Thr
                565                 570                 575

Asn Tyr Asn Gln His Ala Met Val Phe Phe Lys Glu Val Tyr Gln Asn
            580                 585                 590

Arg Glu Ile Phe Phe Ile Ile Leu Tyr Gly Arg Thr Lys Glu Leu Thr
        595                 600                 605

Ser Glu Leu Lys Glu Asn Phe Ile Arg Phe Ser Lys Ser Leu Gly Leu
610                 615                 620

Pro Glu Asn His Ile Val Phe Pro Val Pro Ile Asp Gln Cys Ile Asp
625                 630                 635                 640

Gly

<210> SEQ ID NO 37
<211> LENGTH: 216
<212> TYPE: PRT
<213> ORGANISM: artificial
<220> FEATURE:
<223> OTHER INFORMATION: fusion polypeptide light chain

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 38
<211> LENGTH: 641
<212> TYPE: PRT
<213> ORGANISM: artificial
<220> FEATURE:
<223> OTHER INFORMATION: fusion polypeptide heavy chain
```

<400> SEQUENCE: 38

```
Gln Asp Ser Thr Ser Asp Leu Ile Pro Ala Pro Leu Ser Lys Val
 1               5                  10                  15
Pro Leu Gln Gln Asn Phe Gln Asp Asn Gln Phe Gln Gly Lys Trp Tyr
            20                  25                  30
Val Val Gly Arg Ala Gly Asn Val Gly Leu Arg Glu Asp Lys Asp Pro
        35                  40                  45
Pro Lys Met Trp Ala Thr Ile Tyr Glu Leu Lys Glu Asp Lys Ser Tyr
 50                  55                  60
Asp Val Thr Asn Val Arg Phe Ala Arg Lys Lys Cys Thr Tyr Ser Ile
 65                  70                  75                  80
Gly Thr Phe Val Pro Gly Ser Gln Pro Gly Glu Phe Thr Leu Gly Gln
                85                  90                  95
Ile Lys Ser Glu Pro Gly Gly Thr Ala Asn Leu Val Arg Val Val Ser
            100                 105                 110
Thr Asn Tyr Asn Gln His Ala Met Val Phe Phe Lys Glu Val Tyr Gln
        115                 120                 125
Asn Arg Glu Ile Phe Phe Ile Ile Leu Tyr Gly Arg Thr Lys Glu Leu
    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly Gly Gly Gly Ser Gly Gly Gly Ser Gly Gly Gly Gly
            180                 185                 190
Ser Gln Val Gln Leu Gln Gln Trp Gly Ala Gly Leu Leu Lys Pro Ser
        195                 200                 205
Glu Thr Leu Ser Leu Thr Cys Ala Val Tyr Gly Gly Ser Phe Ser Gly
210                 215                 220
Tyr Tyr Trp Ser Trp Ile Arg Gln Ser Pro Glu Lys Gly Leu Glu Trp
225                 230                 235                 240
Ile Gly Glu Ile Asn His Gly Gly Tyr Val Thr Tyr Asn Pro Ser Leu
                245                 250                 255
Glu Ser Arg Val Thr Ile Ser Val Asp Thr Ser Lys Asn Gln Phe Ser
            260                 265                 270
Leu Lys Leu Ser Ser Val Thr Ala Ala Asp Thr Ala Val Tyr Tyr Cys
        275                 280                 285
Ala Arg Asp Tyr Gly Pro Gly Asn Tyr Asp Trp Tyr Phe Asp Leu Trp
    290                 295                 300
Gly Arg Gly Thr Leu Val Thr Val Ser Ser Ala Ser Thr Lys Gly Pro
305                 310                 315                 320
Ser Val Phe Pro Leu Ala Pro Cys Ser Arg Ser Thr Ser Glu Ser Thr
                325                 330                 335
Ala Ala Leu Gly Cys Leu Val Lys Asp Tyr Phe Pro Glu Pro Val Thr
            340                 345                 350
Val Ser Trp Asn Ser Gly Ala Leu Thr Ser Gly Val His Thr Phe Pro
        355                 360                 365
Ala Val Leu Gln Ser Ser Gly Leu Tyr Ser Leu Ser Ser Val Val Thr
    370                 375                 380
Val Pro Ser Ser Leu Gly Thr Lys Thr Tyr Thr Cys Asn Val Asp
385                 390                 395                 400
His Lys Pro Ser Asn Thr Lys Val Asp Lys Arg Val Glu Ser Lys Tyr
```

```
                    405                 410                 415
Gly Pro Pro Cys Pro Cys Pro Ala Pro Glu Phe Leu Gly Gly Pro
                420                 425                 430

Ser Val Phe Leu Phe Pro Pro Lys Pro Lys Asp Thr Leu Met Ile Ser
            435                 440                 445

Arg Thr Pro Glu Val Thr Cys Val Val Val Asp Val Ser Gln Glu Asp
        450                 455                 460

Pro Glu Val Gln Phe Asn Trp Tyr Val Asp Gly Val Glu Val His Asn
465                 470                 475                 480

Ala Lys Thr Lys Pro Arg Glu Glu Gln Phe Asn Ser Thr Tyr Arg Val
                485                 490                 495

Val Ser Val Leu Thr Val Leu His Gln Asp Trp Leu Asn Gly Lys Glu
            500                 505                 510

Tyr Lys Cys Lys Val Ser Asn Lys Gly Leu Pro Ser Ser Ile Glu Lys
        515                 520                 525

Thr Ile Ser Lys Ala Lys Gly Gln Pro Arg Glu Pro Gln Val Tyr Thr
    530                 535                 540

Leu Pro Pro Ser Gln Glu Glu Met Thr Lys Asn Gln Val Ser Leu Thr
545                 550                 555                 560

Cys Leu Val Lys Gly Phe Tyr Pro Ser Asp Ile Ala Val Glu Trp Glu
                565                 570                 575

Ser Asn Gly Gln Pro Glu Asn Asn Tyr Lys Thr Thr Pro Pro Val Leu
            580                 585                 590

Asp Ser Asp Gly Ser Phe Phe Leu Tyr Ser Arg Leu Thr Val Asp Lys
        595                 600                 605

Ser Arg Trp Gln Glu Gly Asn Val Phe Ser Cys Ser Val Met His Glu
    610                 615                 620

Ala Leu His Asn His Tyr Thr Gln Lys Ser Leu Ser Leu Ser Leu Gly
625                 630                 635                 640

Lys

<210> SEQ ID NO 39
<211> LENGTH: 216
<212> TYPE: PRT
<213> ORGANISM: artificial
<220> FEATURE:
<223> OTHER INFORMATION: fusion polypeptide light chain

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125
```

```
Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 40
<211> LENGTH: 448
<212> TYPE: PRT
<213> ORGANISM: artificial
<220> FEATURE:
<223> OTHER INFORMATION: fusion polypeptide heavy chain

<400> SEQUENCE: 40

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270
```

```
Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 41
<211> LENGTH: 409
<212> TYPE: PRT
<213> ORGANISM: artificial
<220> FEATURE:
<223> OTHER INFORMATION: fusion polypeptide light chain

<400> SEQUENCE: 41

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Val Gly Leu Arg Glu Asp Lys Asp Pro
        35                  40                  45

Pro Lys Met Trp Ala Thr Ile Tyr Glu Leu Lys Glu Asp Lys Ser Tyr
    50                  55                  60

Asp Val Thr Asn Val Arg Phe Ala Arg Lys Lys Cys Thr Tyr Ser Ile
65                  70                  75                  80

Gly Thr Phe Val Pro Gly Ser Gln Pro Gly Glu Phe Thr Leu Gly Gln
                85                  90                  95

Ile Lys Ser Glu Pro Gly Gly Thr Ala Asn Leu Val Arg Val Val Ser
            100                 105                 110

Thr Asn Tyr Asn Gln His Ala Met Val Phe Lys Glu Val Tyr Gln
        115                 120                 125

Asn Arg Glu Ile Phe Phe Ile Ile Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
            180                 185                 190
```

```
Ser Glu Ile Val Leu Thr Gln Ser Pro Ala Thr Leu Ser Leu Ser Pro
            195                 200                 205

Gly Glu Arg Ala Thr Leu Ser Cys Arg Ala Ser Gln Ser Val Ser Ser
        210                 215                 220

Tyr Leu Ala Trp Tyr Gln Gln Lys Pro Gly Gln Ala Pro Arg Leu Leu
225                 230                 235                 240

Ile Tyr Asp Ala Ser Asn Arg Ala Thr Gly Ile Pro Ala Arg Phe Ser
                245                 250                 255

Gly Ser Gly Ser Gly Thr Asp Phe Thr Leu Thr Ile Ser Ser Leu Glu
            260                 265                 270

Pro Glu Asp Phe Ala Val Tyr Tyr Cys Gln Gln Arg Ser Asn Trp Pro
        275                 280                 285

Pro Ala Leu Thr Phe Gly Gly Gly Thr Lys Val Glu Ile Lys Arg Thr
        290                 295                 300

Val Ala Ala Pro Ser Val Phe Ile Phe Pro Pro Ser Asp Glu Gln Leu
305                 310                 315                 320

Lys Ser Gly Thr Ala Ser Val Val Cys Leu Leu Asn Asn Phe Tyr Pro
                325                 330                 335

Arg Glu Ala Lys Val Gln Trp Lys Val Asp Asn Ala Leu Gln Ser Gly
            340                 345                 350

Asn Ser Gln Glu Ser Val Thr Glu Gln Asp Ser Lys Asp Ser Thr Tyr
        355                 360                 365

Ser Leu Ser Ser Thr Leu Thr Leu Ser Lys Ala Asp Tyr Glu Lys His
        370                 375                 380

Lys Val Tyr Ala Cys Glu Val Thr His Gln Gly Leu Ser Ser Pro Val
385                 390                 395                 400

Thr Lys Ser Phe Asn Arg Gly Glu Cys
                405

<210> SEQ ID NO 42
<211> LENGTH: 448
<212> TYPE: PRT
<213> ORGANISM: artificial
<220> FEATURE:
<223> OTHER INFORMATION: fusion polypeptide heavy chain

<400> SEQUENCE: 42

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Thr Val
        180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
            435                 440                 445

<210> SEQ ID NO 43
<211> LENGTH: 408
<212> TYPE: PRT
<213> ORGANISM: artificial
<220> FEATURE:
<223> OTHER INFORMATION: fusion polypeptide light chain

<400> SEQUENCE: 43

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60
```

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Gly Gly Ser Gly Gly Gly
210                 215                 220

Gly Ser Gly Gly Gly Ser Gln Asp Ser Thr Ser Asp Leu Ile Pro
225                 230                 235                 240

Ala Pro Pro Leu Ser Lys Val Pro Leu Gln Gln Asn Phe Gln Asp Asn
            245                 250                 255

Gln Phe Gln Gly Lys Trp Tyr Val Gly Arg Ala Gly Asn Val Gly
                260                 265                 270

Leu Arg Glu Asp Lys Asp Pro Pro Lys Met Trp Ala Thr Ile Tyr Glu
        275                 280                 285

Leu Lys Glu Asp Lys Ser Tyr Asp Val Thr Asn Val Arg Phe Ala Arg
290                 295                 300

Lys Lys Cys Thr Tyr Ser Ile Gly Thr Phe Val Pro Gly Ser Gln Pro
305                 310                 315                 320

Gly Glu Phe Thr Leu Gly Gln Ile Lys Ser Pro Gly Gly Thr Ala
            325                 330                 335

Asn Leu Val Arg Val Val Ser Thr Asn Tyr Asn Gln His Ala Met Val
        340                 345                 350

Phe Phe Lys Glu Val Tyr Gln Asn Arg Glu Ile Phe Phe Ile Ile Leu
            355                 360                 365

Tyr Gly Arg Thr Lys Glu Leu Thr Ser Glu Leu Lys Glu Asn Phe Ile
        370                 375                 380

Arg Phe Ser Lys Ser Leu Gly Leu Pro Glu Asn His Ile Val Phe Pro
385                 390                 395                 400

Val Pro Ile Asp Gln Cys Ile Asp
                405

<210> SEQ ID NO 44
<211> LENGTH: 615
<212> TYPE: PRT
<213> ORGANISM: artificial
<220> FEATURE:
<223> OTHER INFORMATION: fusion polypeptide

<400> SEQUENCE: 44

Gln Asp Ser Thr Ser Asp Leu Ile Pro Ala Pro Pro Leu Ser Lys Val
1               5                   10                  15

```
Pro Leu Gln Gln Asn Phe Gln Asp Asn Gln Phe Gln Gly Lys Trp Tyr
            20                  25                  30
Val Val Gly Arg Ala Gly Asn Val Gly Leu Arg Glu Asp Lys Asp Pro
            35                  40                  45
Pro Lys Met Trp Ala Thr Ile Tyr Glu Leu Lys Glu Asp Lys Ser Tyr
 50                  55                  60
Asp Val Thr Asn Val Arg Phe Ala Arg Lys Lys Cys Thr Tyr Ser Ile
 65                  70                  75                  80
Gly Thr Phe Val Pro Gly Ser Gln Pro Gly Glu Phe Thr Leu Gly Gln
            85                  90                  95
Ile Lys Ser Glu Pro Gly Gly Thr Ala Asn Leu Val Arg Val Val Ser
            100                 105                 110
Thr Asn Tyr Asn Gln His Ala Met Val Phe Phe Lys Glu Val Tyr Gln
            115                 120                 125
Asn Arg Glu Ile Phe Phe Ile Ile Leu Tyr Gly Arg Thr Lys Glu Leu
            130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
            165                 170                 175
Asp Gly Gly Gly Gly Ser Gly Gly Gly Ser Gly Gly Gly Gly
            180                 185                 190
Ser Glu Ser Lys Tyr Gly Pro Pro Cys Pro Pro Cys Pro Ala Pro Glu
            195                 200                 205
Ala Ala Gly Gly Pro Ser Val Phe Leu Phe Pro Pro Lys Pro Lys Asp
            210                 215                 220
Thr Leu Met Ile Ser Arg Thr Pro Glu Val Thr Cys Val Val Val Asp
225                 230                 235                 240
Val Ser Gln Glu Asp Pro Glu Val Gln Phe Asn Trp Tyr Val Asp Gly
            245                 250                 255
Val Glu Val His Asn Ala Lys Thr Lys Pro Arg Glu Glu Gln Phe Asn
            260                 265                 270
Ser Thr Tyr Arg Val Val Ser Val Leu Thr Val Leu His Gln Asp Trp
            275                 280                 285
Leu Asn Gly Lys Glu Tyr Lys Cys Lys Val Ser Asn Lys Gly Leu Pro
            290                 295                 300
Ser Ser Ile Glu Lys Thr Ile Ser Lys Ala Lys Gly Gln Pro Arg Glu
305                 310                 315                 320
Pro Gln Val Tyr Thr Leu Pro Pro Ser Gln Glu Met Thr Lys Asn
            325                 330                 335
Gln Val Ser Leu Thr Cys Leu Val Lys Gly Phe Tyr Pro Ser Asp Ile
            340                 345                 350
Ala Val Glu Trp Glu Ser Asn Gly Gln Pro Glu Asn Asn Tyr Lys Thr
            355                 360                 365
Thr Pro Pro Val Leu Asp Ser Asp Gly Ser Phe Phe Leu Tyr Ser Arg
            370                 375                 380
Leu Thr Val Asp Lys Ser Arg Trp Gln Glu Gly Asn Val Phe Ser Cys
385                 390                 395                 400
Ser Val Met His Glu Ala Leu His Asn His Tyr Thr Gln Lys Ser Leu
            405                 410                 415
Ser Leu Ser Leu Gly Lys Gly Gly Gly Gly Ser Gly Gly Gly Gly Ser
            420                 425                 430
```

-continued

```
Gly Gly Gly Gly Ser Gln Asp Ser Thr Ser Asp Leu Ile Pro Ala Pro
            435                 440                 445

Pro Leu Ser Lys Val Pro Leu Gln Gln Asn Phe Gln Asp Asn Gln Phe
    450                 455                 460

His Gly Lys Trp Tyr Val Val Gly Gln Ala Gly Asn Ile Arg Leu Arg
465                 470                 475                 480

Glu Asp Lys Asp Pro Ile Lys Met Met Ala Thr Ile Tyr Glu Leu Lys
                485                 490                 495

Glu Asp Lys Ser Tyr Asp Val Thr Met Val Lys Phe Asp Lys Lys
            500                 505                 510

Cys Met Tyr Asp Ile Trp Thr Phe Val Pro Gly Ser Gln Pro Gly Glu
            515                 520                 525

Phe Thr Leu Gly Lys Ile Lys Ser Phe Pro Gly His Thr Ser Ser Leu
        530                 535                 540

Val Arg Val Val Ser Thr Asn Tyr Asn Gln His Ala Met Val Phe Phe
545                 550                 555                 560

Lys Phe Val Phe Gln Asn Arg Glu Glu Phe Tyr Ile Thr Leu Tyr Gly
                565                 570                 575

Arg Thr Lys Glu Leu Thr Ser Glu Leu Lys Glu Asn Phe Ile Arg Phe
            580                 585                 590

Ser Lys Ser Leu Gly Leu Pro Glu Asn His Ile Val Phe Pro Val Pro
        595                 600                 605

Ile Asp Gln Cys Ile Asp Gly
    610                 615

<210> SEQ ID NO 45
<211> LENGTH: 610
<212> TYPE: PRT
<213> ORGANISM: artificial
<220> FEATURE:
<223> OTHER INFORMATION: fusion polypeptide

<400> SEQUENCE: 45

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Arg Ala Gly Asn Val Gly Leu Arg Glu Asp Lys Asp Pro
        35                  40                  45

Pro Lys Met Trp Ala Thr Ile Tyr Glu Leu Lys Glu Asp Lys Ser Tyr
    50                  55                  60

Asp Val Thr Asn Val Arg Phe Ala Arg Lys Lys Cys Thr Tyr Ser Ile
65                  70                  75                  80

Gly Thr Phe Val Pro Gly Ser Gln Pro Gly Glu Phe Thr Leu Gly Gln
                85                  90                  95

Ile Lys Ser Glu Pro Gly Gly Thr Ala Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Ile Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

```
Asp Gly Gly Gly Gly Ser Gly Gly Gly Ser Gln Asp Ser Thr
            180             185             190

Ser Asp Leu Ile Pro Ala Pro Leu Ser Lys Val Pro Leu Gln Gln
        195             200             205

Asn Phe Gln Asp Asn Gln Phe His Gly Lys Trp Tyr Val Val Gly Gln
    210             215             220

Ala Gly Asn Ile Arg Leu Arg Glu Asp Lys Asp Pro Ile Lys Met Met
225             230             235             240

Ala Thr Ile Tyr Glu Leu Lys Glu Asp Lys Ser Tyr Asp Val Thr Met
            245             250             255

Val Lys Phe Asp Asp Lys Lys Cys Met Tyr Asp Ile Trp Thr Phe Val
        260             265             270

Pro Gly Ser Gln Pro Gly Glu Phe Thr Leu Gly Lys Ile Lys Ser Phe
    275             280             285

Pro Gly His Thr Ser Ser Leu Val Arg Val Val Ser Thr Asn Tyr Asn
    290             295             300

Gln His Ala Met Val Phe Phe Lys Phe Val Phe Gln Asn Arg Glu Glu
305             310             315             320

Phe Tyr Ile Thr Leu Tyr Gly Arg Thr Lys Glu Leu Thr Ser Glu Leu
            325             330             335

Lys Glu Asn Phe Ile Arg Phe Ser Lys Ser Leu Gly Leu Pro Glu Asn
        340             345             350

His Ile Val Phe Pro Val Pro Ile Asp Gln Cys Ile Asp Gly Gly Gly
    355             360             365

Gly Gly Ser Gly Gly Gly Ser Gly Gly Gly Ser Glu Ser Lys
    370             375             380

Tyr Gly Pro Pro Cys Pro Pro Cys Pro Ala Pro Glu Ala Ala Gly Gly
385             390             395             400

Pro Ser Val Phe Leu Phe Pro Pro Lys Pro Lys Asp Thr Leu Met Ile
            405             410             415

Ser Arg Thr Pro Glu Val Thr Cys Val Val Val Asp Val Ser Gln Glu
        420             425             430

Asp Pro Glu Val Gln Phe Asn Trp Tyr Val Asp Gly Val Glu Val His
    435             440             445

Asn Ala Lys Thr Lys Pro Arg Glu Glu Gln Phe Asn Ser Thr Tyr Arg
450             455             460

Val Val Ser Val Leu Thr Val Leu His Gln Asp Trp Leu Asn Gly Lys
465             470             475             480

Glu Tyr Lys Cys Lys Val Ser Asn Lys Gly Leu Pro Ser Ser Ile Glu
            485             490             495

Lys Thr Ile Ser Lys Ala Lys Gly Gln Pro Arg Glu Pro Gln Val Tyr
        500             505             510

Thr Leu Pro Pro Ser Gln Glu Glu Met Thr Lys Asn Gln Val Ser Leu
    515             520             525

Thr Cys Leu Val Lys Gly Phe Tyr Pro Ser Asp Ile Ala Val Glu Trp
    530             535             540

Glu Ser Asn Gly Gln Pro Glu Asn Asn Tyr Lys Thr Thr Pro Pro Val
545             550             555             560

Leu Asp Ser Asp Gly Ser Phe Phe Leu Tyr Ser Arg Leu Thr Val Asp
            565             570             575

Lys Ser Arg Trp Gln Glu Gly Asn Val Phe Ser Cys Ser Val Met His
        580             585             590

Glu Ala Leu His Asn His Tyr Thr Gln Lys Ser Leu Ser Leu Ser Leu
```

```
                    595                 600                 605

Gly Lys
    610

<210> SEQ ID NO 46
<211> LENGTH: 366
<212> TYPE: PRT
<213> ORGANISM: artificial
<220> FEATURE:
<223> OTHER INFORMATION: fusion polypeptide

<400> SEQUENCE: 46

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Val Ala Gly Asn Gly Met Leu Arg Glu Asp Lys Asp Pro
        35                  40                  45

Leu Lys Met Arg Ala Thr Ile Tyr Glu Leu Lys Glu Asp Lys Ser Tyr
50                  55                  60

Asp Val Thr Ser Val Ala Phe Arg Asn Lys Lys Cys His Tyr Lys Ile
65                  70                  75                  80

Gly Thr Phe Val Pro Gly Ser Gln Pro Gly Glu Phe Thr Leu Gly Gln
                85                  90                  95

Ile Lys Ser Gly Pro Gly Glu Thr Ser Asn Leu Val Arg Val Val Ser
            100                 105                 110

Thr Asn Tyr Asn Gln His Ala Met Val Phe Phe Lys Glu Val Arg Gln
        115                 120                 125

Asn Arg Glu Trp Phe Phe Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gln Asp Ser Thr
            180                 185                 190

Ser Asp Leu Ile Pro Ala Pro Pro Leu Ser Lys Val Pro Leu Gln Gln
        195                 200                 205

Asn Phe Gln Asp Asn Gln Phe His Gly Lys Trp Tyr Val Val Gly Gln
210                 215                 220

Ala Gly Asn Ile Arg Leu Arg Glu Asp Lys Asp Pro Ile Lys Met Met
225                 230                 235                 240

Ala Thr Ile Tyr Glu Leu Lys Glu Asp Lys Ser Tyr Asp Val Thr Met
                245                 250                 255

Val Lys Phe Asp Asp Lys Lys Cys Met Tyr Asp Ile Trp Thr Phe Val
            260                 265                 270

Pro Gly Ser Gln Pro Gly Glu Phe Thr Leu Gly Lys Ile Lys Ser Phe
        275                 280                 285

Pro Gly His Thr Ser Ser Leu Val Arg Val Val Ser Thr Asn Tyr Asn
290                 295                 300

Gln His Ala Met Val Phe Phe Lys Phe Val Gln Asn Arg Glu Glu
305                 310                 315                 320

Phe Tyr Ile Thr Leu Tyr Gly Arg Thr Lys Glu Leu Thr Ser Glu Leu
                325                 330                 335

Lys Glu Asn Phe Ile Arg Phe Ser Lys Ser Leu Gly Leu Pro Glu Asn
```

His Ile Val Phe Pro Val Pro Ile Asp Gln Cys Ile Asp Gly
                340                 345                 350
        355                 360                 365

<210> SEQ ID NO 47
<211> LENGTH: 554
<212> TYPE: PRT
<213> ORGANISM: artificial
<220> FEATURE:
<223> OTHER INFORMATION: fusion polypeptide

<400> SEQUENCE: 47

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Val Ala Gly Asn Gly Met Leu Arg Glu Asp Lys Asp Pro
        35                  40                  45

Leu Lys Met Arg Ala Thr Ile Tyr Glu Leu Lys Glu Asp Lys Ser Tyr
    50                  55                  60

Asp Val Thr Ser Val Ala Phe Arg Asn Lys Lys Cys His Tyr Lys Ile
65                  70                  75                  80

Gly Thr Phe Val Pro Gly Ser Gln Pro Gly Glu Phe Thr Leu Gly Gln
                85                  90                  95

Ile Lys Ser Gly Pro Gly Glu Thr Ser Asn Leu Val Arg Val Val Ser
            100                 105                 110

Thr Asn Tyr Asn Gln His Ala Met Val Phe Phe Lys Glu Val Arg Gln
        115                 120                 125

Asn Arg Glu Trp Phe Phe Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Gly Ser Gly Gly Gly Gly Ser Gln Asp Ser Thr
            180                 185                 190

Ser Asp Leu Ile Pro Ala Pro Pro Leu Ser Lys Val Pro Leu Gln Gln
        195                 200                 205

Asn Phe Gln Asp Asn Gln Phe His Gly Lys Trp Tyr Val Val Gly Gln
    210                 215                 220

Ala Gly Asn Ile Arg Leu Arg Glu Asp Lys Asp Pro Ile Lys Met Met
225                 230                 235                 240

Ala Thr Ile Tyr Glu Leu Lys Glu Asp Lys Ser Tyr Asp Val Thr Met
                245                 250                 255

Val Lys Phe Asp Asp Lys Lys Cys Met Tyr Asp Ile Trp Thr Phe Val
            260                 265                 270

Pro Gly Ser Gln Pro Gly Glu Phe Thr Leu Gly Lys Ile Lys Ser Phe
        275                 280                 285

Pro Gly His Thr Ser Ser Leu Val Arg Val Val Ser Thr Asn Tyr Asn
    290                 295                 300

Gln His Ala Met Val Phe Phe Lys Phe Val Gln Asn Arg Glu Glu
305                 310                 315                 320

Phe Tyr Ile Thr Leu Tyr Gly Arg Thr Lys Glu Leu Thr Ser Glu Leu
                325                 330                 335

Lys Glu Asn Phe Ile Arg Phe Ser Lys Ser Leu Gly Leu Pro Glu Asn

-continued

```
                340                 345                 350
His Ile Val Phe Pro Val Pro Ile Asp Gln Cys Ile Asp Gly Gly Gly
                355                 360                 365

Gly Gly Ser Gly Gly Gly Gly Ser Gln Asp Ser Thr Ser Asp Leu Ile
        370                 375                 380

Pro Ala Pro Pro Leu Ser Lys Val Pro Leu Gln Gln Asn Phe Gln Asp
385                 390                 395                 400

Asn Gln Phe His Gly Lys Trp Tyr Val Val Gly Gln Ala Gly Asn Ile
                405                 410                 415

Arg Leu Arg Glu Asp Lys Asp Pro Ile Lys Met Met Ala Thr Ile Tyr
            420                 425                 430

Glu Leu Lys Glu Asp Lys Ser Tyr Asp Val Thr Met Val Lys Phe Asp
        435                 440                 445

Asp Lys Lys Cys Met Tyr Asp Ile Trp Thr Phe Val Pro Gly Ser Gln
    450                 455                 460

Pro Gly Glu Phe Thr Leu Gly Lys Ile Lys Ser Phe Pro Gly His Thr
465                 470                 475                 480

Ser Ser Leu Val Arg Val Val Ser Thr Asn Tyr Asn Gln His Ala Met
                485                 490                 495

Val Phe Phe Lys Phe Val Phe Gln Asn Arg Glu Glu Phe Tyr Ile Thr
            500                 505                 510

Leu Tyr Gly Arg Thr Lys Glu Leu Thr Ser Glu Leu Lys Glu Asn Phe
        515                 520                 525

Ile Arg Phe Ser Lys Ser Leu Gly Leu Pro Glu Asn His Ile Val Phe
    530                 535                 540

Pro Val Pro Ile Asp Gln Cys Ile Asp Gly
545                 550
```

<210> SEQ ID NO 48
<211> LENGTH: 11
<212> TYPE: PRT
<213> ORGANISM: artificial
<220> FEATURE:
<223> OTHER INFORMATION: peptide linker

<400> SEQUENCE: 48

```
Gly Gly Gly Gly Ser Gly Gly Gly Gly Ser
1               5                   10
```

<210> SEQ ID NO 49
<211> LENGTH: 15
<212> TYPE: PRT
<213> ORGANISM: artificial
<220> FEATURE:
<223> OTHER INFORMATION: peptide linker

<400> SEQUENCE: 49

```
Gly Gly Gly Gly Ser Gly Gly Gly Gly Ser Gly Gly Gly Gly Ser
1               5                   10                  15
```

<210> SEQ ID NO 50
<211> LENGTH: 10
<212> TYPE: PRT
<213> ORGANISM: artificial
<220> FEATURE:
<223> OTHER INFORMATION: Strep tag

<400> SEQUENCE: 50

```
Ser Ala Trp Ser His Pro Gln Phe Glu Lys
1               5                   10
```

```
<210> SEQ ID NO 51
<211> LENGTH: 442
<212> TYPE: PRT
<213> ORGANISM: artificial
<220> FEATURE:
<223> OTHER INFORMATION: antibody heavy chain

<400> SEQUENCE: 51
```

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly Lys
                435                 440

<210> SEQ ID NO 52
<211> LENGTH: 214
<212> TYPE: PRT
<213> ORGANISM: artificial
<220> FEATURE:
<223> OTHER INFORMATION: antibody light chain

<400> SEQUENCE: 52

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
                20                  25                  30

His Trp Tyr Gln Gln Lys Pro Gly Gln Ser Pro Val Leu Val Ile Tyr
            35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 53
<211> LENGTH: 635
<212> TYPE: PRT
<213> ORGANISM: artificial
<220> FEATURE:
<223> OTHER INFORMATION: fusion polypeptide heavy chain

<400> SEQUENCE: 53

Glu Val Gln Leu Val Gln Ser Gly Ala Glu Val Lys Lys Pro Gly Glu

-continued

```
1               5                   10                  15
Ser Leu Arg Ile Ser Cys Lys Gly Ser Gly Tyr Ser Phe Ser Thr Tyr
            20                  25                  30
Trp Ile Ser Trp Val Arg Gln Met Pro Gly Lys Gly Leu Glu Trp Met
            35                  40                  45
Gly Lys Ile Tyr Pro Gly Asp Ser Tyr Thr Asn Tyr Ser Pro Ser Phe
            50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Gly Tyr Gly Ile Phe Asp Tyr Trp Gly Gln Gly Thr Leu Val
                100                 105                 110
Thr Val Ser Ser Ala Ser Thr Lys Gly Pro Ser Val Phe Pro Leu Ala
                115                 120                 125
Pro Cys Ser Arg Ser Thr Ser Glu Ser Thr Ala Ala Leu Gly Cys Leu
            130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Asn Phe
                180                 185                 190
Gly Thr Gln Thr Tyr Thr Cys Asn Val Asp His Lys Pro Ser Asn Thr
                195                 200                 205
Lys Val Asp Lys Thr Val Glu Arg Lys Cys Cys Val Glu Cys Pro Pro
210                 215                 220
Cys Pro Ala Pro Pro Val Ala Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser His Glu Asp Pro Glu Val Gln Phe Asn Trp
                260                 265                 270
Tyr Val Asp Gly Val Glu Val His Asn Ala Lys Thr Lys Pro Arg Glu
                275                 280                 285
Glu Gln Phe Asn Ser Thr Phe Arg Val Val Ser Val Leu Thr Val Val
            290                 295                 300
His Gln Asp Trp Leu Asn Gly Lys Glu Tyr Lys Cys Lys Val Ser Asn
305                 310                 315                 320
Lys Gly Leu Pro Ala Pro Ile Glu Lys Thr Ile Ser Lys Thr Lys Gly
                325                 330                 335
Gln Pro Arg Glu Pro Gln Val Tyr Thr Leu Pro Pro Ser Arg Glu Glu
                340                 345                 350
Met Thr Lys Asn Gln Val Ser Leu Thr Cys Leu Val Lys Gly Phe Tyr
            355                 360                 365
Pro Ser Asp Ile Ala Val Glu Trp Glu Ser Asn Gly Gln Pro Glu Asn
            370                 375                 380
Asn Tyr Lys Thr Thr Pro Pro Met Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
                420                 425                 430
```

```
Gln Lys Ser Leu Ser Leu Ser Pro Gly Lys Gly Gly Gly Ser Gly
            435                 440                 445

Gly Gly Gly Ser Gly Gly Gly Ser Gln Asp Ser Thr Ser Asp Leu
450                 455                 460

Ile Pro Ala Pro Pro Leu Ser Lys Val Pro Leu Gln Gln Asn Phe Gln
465                 470                 475                 480

Asp Asn Gln Phe Gln Gly Lys Trp Tyr Val Val Gly Arg Ala Gly Asn
                485                 490                 495

Val Gly Leu Arg Glu Asp Lys Asp Pro Pro Lys Met Trp Ala Thr Ile
            500                 505                 510

Tyr Glu Leu Lys Glu Asp Lys Ser Tyr Asp Val Thr Asn Val Arg Phe
            515                 520                 525

Ala Arg Lys Lys Cys Thr Tyr Ser Ile Gly Thr Phe Val Pro Gly Ser
            530                 535                 540

Gln Pro Gly Glu Phe Thr Leu Gly Gln Ile Lys Ser Glu Pro Gly Gly
545                 550                 555                 560

Thr Ala Asn Leu Val Arg Val Ser Thr Asn Tyr Asn Gln His Ala
                565                 570                 575

Met Val Phe Phe Lys Glu Val Tyr Gln Asn Arg Glu Ile Phe Phe Ile
                580                 585                 590

Ile Leu Tyr Gly Arg Thr Lys Glu Leu Thr Ser Glu Leu Lys Glu Asn
                595                 600                 605

Phe Ile Arg Phe Ser Lys Ser Leu Gly Leu Pro Glu Asn His Ile Val
            610                 615                 620

Phe Pro Val Pro Ile Asp Gln Cys Ile Asp Gly
625                 630                 635

<210> SEQ ID NO 54
<211> LENGTH: 214
<212> TYPE: PRT
<213> ORGANISM: artificial
<220> FEATURE:
<223> OTHER INFORMATION: fusion polypeptide light chain

<400> SEQUENCE: 54

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160
```

Val Glu Thr Thr Thr Pro Ser Lys Gln Ser Asn Asn Lys Tyr Ala Ala
            165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
    210

<210> SEQ ID NO 55
<211> LENGTH: 1344
<212> TYPE: DNA
<213> ORGANISM: artificial
<220> FEATURE:
<223> OTHER INFORMATION: antibody heavy chain

<400> SEQUENCE: 55

| | | | | | |
|---|---|---|---|---|---|
| caggtccagc | tgcagcagtg | gggggctggt | ctgctgaagc | caagtgaaac | tctgtcactg | 60 |
| acctgcgctg | tgtacggcgg | atcattctcc | ggctactatt | ggtcttggat | cagacagagt | 120 |
| cccgagaaag | gcctggaatg | gatcggagag | attaaccacg | ggggttacgt | gacctataat | 180 |
| cctagcctgg | agtctagggt | gaccatttcc | gtcgacacaa | gcaagaacca | gttctctctg | 240 |
| aaactgtcca | gcgtgacagc | cgctgacact | gcagtctact | attgtgccag | ggattatggc | 300 |
| cccggaaatt | acgactggta | ttttgatctg | tgggggcggg | gtaccctggt | gacagtctcg | 360 |
| agcgctagca | ccaagggccc | ctccgtgttc | cccctggccc | cttgctcccg | gtccacctcc | 420 |
| gagtctaccg | ccgctctggg | ctgcctggtg | aaagactact | ccccgagcc | tgtgaccgtg | 480 |
| agctggaact | ctggcgccct | gacctccggc | gtgcacacct | ccctgccgt | gctgcaatcc | 540 |
| tccggcctgt | actccctgtc | ctccgtggtg | acagtgccct | cctccagcct | gggcaccaag | 600 |
| acctacacct | gtaacgtgga | ccacaagccc | tccaacacca | aggtggacaa | gcgggtggaa | 660 |
| tctaaatacg | gccctcccctg | ccccccctgc | cctgcccctg | aatttctggg | cggaccttcc | 720 |
| gtgtttctgt | tccccccaaa | gcccaaggac | accctgatga | tctcccggac | ccccgaagtg | 780 |
| acctgcgtgg | tggtggacgt | gtcccaggaa | gatccagagg | tgcagttcaa | ctggtatgtt | 840 |
| gacggcgtgg | aagtgcacaa | cgccaagacc | aagcccagag | aggaacagtt | caactccacc | 900 |
| taccgggtgg | tgtccgtgct | gaccgtgctg | caccaggact | ggctgaacgg | caaagagtac | 960 |
| aagtgcaagg | tgtccaacaa | gggcctgccc | tccagcatcg | aaaagaccat | ctccaaggcc | 1020 |
| aagggccagc | cccgcgagcc | ccaggtgtac | accctgcccc | ctagccagga | agagatgacc | 1080 |
| aagaaccagg | tgtccctgac | ctgtctggtg | aaaggcttct | acccctccga | cattgccgtg | 1140 |
| gaatgggagt | ccaacggcca | gcccgagaac | aactacaaga | ccaccccccc | tgtgctggac | 1200 |
| tccgacggct | ccttcttcct | gtactctcgg | ctgacagtgg | ataagtcccg | gtggcaggaa | 1260 |
| ggcaacgtgt | tctcctgcag | cgtgatgcac | gaggccctgc | acaaccacta | cacccagaag | 1320 |
| tccctgtccc | tgagcctggg | caag | | | | 1344 |

<210> SEQ ID NO 56
<211> LENGTH: 648
<212> TYPE: DNA
<213> ORGANISM: artificial
<220> FEATURE:
<223> OTHER INFORMATION: antibody light chain

<400> SEQUENCE: 56

```
gagattgtcc tgacccagtc ccccgcaaca ctgtcactgt ccccggcga gagggctact      60 ctgagttgcc gggcaagcca gtctgtgtcc agctacctgg cctggtatca gcagaagcca    120
gggcaggctc ccagactgct gatctacgac gcatctaaca gagccaccgg aattcctgcc    180
cgcttctcgg gttcaggctc cggaacagac tttaccctga caatctctag tctggagcca    240
gaagatttcg cagtctacta ttgtcagcag cgaagcaatt ggcccctgc tctgactttt    300 ggcggaggga ccaaggtgga gatcaagcgt acggtcgcgg cgccttctgt gttcattttc    360 ccccatctg atgaacagct gaaatctggc actgcttctg tggtctgtct gctgaacaac    420
ttctacccta gagaggccaa agtccagtgg aaagtggaca atgctctgca gagtgggaat    480
tcccaggaat ctgtcactga gcaggactct aaggatagca catactccct gtcctctact    540
ctgacactga gcaaggctga ttacgagaaa cacaaagtgt acgcctgtga agtcacacat    600
caggggctgt ctagtcctgt gaccaaatcc ttcaataggg gagagtgc                 648

<210> SEQ ID NO 57
<211> LENGTH: 1923
<212> TYPE: DNA
<213> ORGANISM: artificial
<220> FEATURE:
<223> OTHER INFORMATION: fusion polypeptide heavy chain

<400> SEQUENCE: 57
caggtccagc tgcagcagtg gggggctggt ctgctgaagc caagtgaaac tctgtcactg      60
acctgcgctg tgtacggcgg atcattctcc ggctactatt ggtcttggat cagacagagt    120
cccgagaaag gcctggaatg gatcggagag attaaccacg ggggttacgt gacctataat    180
cctagcctgg agtctagggt gaccatttcc gtcgacacaa gcaagaacca gttctctctg    240
aaactgtcca gcgtgacagc cgctgacact gcagtctact attgtgccag ggattatggc    300
cccggaaatt acgactggta ttttgatctg tggggcggg gtaccctggt gacagtctcg    360
agcgctagca ccaagggccc ctccgtgttc cccctggccc cttgctcccg gtccacctcc    420
gagtctaccg ccgctctggg ctgcctggtg aaagactact cccccgagcc tgtgaccgtg    480
agctggaact ctggcgccct gacctccggc gtgcacacct ccctgccgt gctgcaatcc    540 tccggcctgt actccctgtc ctccgtggtg acagtgccct cctccagcct gggcaccaag    600
acctacacct gtaacgtgga ccacaagccc tccaacacca aggtggacaa gcgggtggaa    660
tctaaatacg gcctcccctg ccccccctgc cctgcccctg aatttctggg cggaccttcc    720
gtgtttctgt tcccccaaa gcccaaggac ccctgatga tctcccggac ccccgaagtg    780
acctgcgtgg tggtggacgt gtcccaggaa gatccagagg tgcagttcaa ctggtatgtt    840
gacggcgtga agtgcacaa cgccaagacc aagcccagag aggaacagtt caactccacc    900
taccgggtgg tgtccgtgct gaccgtgctg caccaggact ggctgaacgg caaagagtac    960
aagtgcaagg tgtccaacaa gggcctgccc tccagcatcg aaaagaccat ctccaaggcc    1020
aagggccagc ccgcgagcc ccaggtgtac accctgcccc ctagccagga agagatgacc    1080
aagaaccagg tgtccctgac ctgtctggtg aaaggcttct accctcccga cattgccgtg    1140
gaatgggagt ccaacggcca gcccgagaac aactacaaga ccaccccccc tgtgctggac    1200
tccgacggct ccttcttcct gtactctcgg ctgacagtgg ataagtcccg gtggcaggaa    1260
ggcaacgtgt tctcctgcag cgtgatgcac gaggccctgc acaaccacta cccagaag    1320 tccctgtccc tgagcctggg caaggcggt ggaggatccg gggtgggg aagcggcgga    1380 ggaggtagcc aggactccac tagcgatctg atcccggctc cccctctgag taaggtgccc    1440
```

| | |
|---|---|
| ctgcaacaaa acttccaaga caatcagttt cagggcaaat ggtacgtggt cgggagagct | 1500 |
| ggtaacgtgg gactgcgaga ggacaaggac cccccaaaa tgtgggccac catctacgag | 1560 |
| ctgaaggaag acaaaagcta tgatgtgaca aatgtcaggt tcgcacggaa gaaatgcact | 1620 |
| tactcaatcg gcaccttcgt gcccggctcc cagcctgggg agtttacact gggccagatt | 1680 |
| aagagcgaac ctggcggaac agccaacctg gtgcgggtgg tctctactaa ctataatcag | 1740 |
| cacgctatgt gttctttaa agaggtctac cagaaccgag aaatcttctt tatcatcctg | 1800 |
| tacggccgta ccaaggagct gacatccgag ctgaagaaa acttcatccg ctttctaag | 1860 |
| agtctgggac tgccagaaaa tcatattgtg tttcctgtcc caatcgacca gtgtattgat | 1920 |
| ggg | 1923 |

<210> SEQ ID NO 58
<211> LENGTH: 648
<212> TYPE: DNA
<213> ORGANISM: artificial
<220> FEATURE:
<223> OTHER INFORMATION: fusion polypeptide light chain

<400> SEQUENCE: 58

| | |
|---|---|
| gagattgtcc tgacccagtc ccccgcaaca ctgtcactgt cccccggcga gagggctact | 60 |
| ctgagttgcc gggcaagcca gtctgtgtcc agctacctgg cctggtatca gcagaagcca | 120 |
| gggcaggctc ccagactgct gatctacgac gcatctaaca gagccaccgg aattcctgcc | 180 |
| cgcttctcgg gttcaggctc cggaacagac tttacccctga caatctctag tctggagcca | 240 |
| gaagatttcg cagtctacta ttgtcagcag cgaagcaatt ggccccctgc tctgactttt | 300 |
| ggcggaggga ccaaggtgga gatcaagcgt acggtcgcgg cgccttctgt gttcattttc | 360 |
| cccccatctg atgaacagct gaaatctggc actgcttctg tggtctgtct gctgaacaac | 420 |
| ttctacccta gagaggccaa agtccagtgg aaagtggaca atgctctgca gagtgggaat | 480 |
| tcccaggaat ctgtcactga gcaggactct aaggatagca catactccct gtcctctact | 540 |
| ctgacactga gcaaggctga ttacgagaaa cacaaagtgt acgcctgtga agtcacacat | 600 |
| caggggctgt ctagtcctgt gaccaaatcc ttcaataggg gagagtgc | 648 |

<210> SEQ ID NO 59
<211> LENGTH: 1923
<212> TYPE: DNA
<213> ORGANISM: artificial
<220> FEATURE:
<223> OTHER INFORMATION: fusion polypeptide heavy chain

<400> SEQUENCE: 59

| | |
|---|---|
| caggactcca ctagcgatct gatcccggct cccctctga gtaaggtgcc cctgcaacaa | 60 |
| aacttccaag acaatcagtt tcagggcaaa tggtacgtgg tcgggagagc tggtaacgtg | 120 |
| ggactgcgag aggacaagga ccccccaaa atgtgggcca ccatctacga gctgaaggaa | 180 |
| gacaaaagct atgatgtgac aaatgtcagg ttcgcacgga gaaatgcac ttactcaatc | 240 |
| ggcaccttcg tgcccggctc ccagcctggg gagtttacac tgggccagat taagagcgaa | 300 |
| cctggcggaa cagccaacct ggtgcgggtg gtctctacta actataatca gcacgctatg | 360 |
| gtgttctta agaggtcta ccagaaccga gaaatcttct ttatcatcct gtacggccgt | 420 |
| accaaggagc tgacatccga gctgaagaaa aacttcatcc gctttctaa gagtctggga | 480 |
| ctgccagaaa atcatattgt gtttcctgtc ccaatcgacc agtgtattga tgggggcggt | 540 |

```
ggaggatccg ggggtggggg aagcggcgga ggaggtagcc aggtgcaact gcaacaatgg      600
ggcgcaggct tgttgaagcc ctctgagaca ctgagtctta cctgtgctgt gtacggtggc      660
agcttttccg gatactattg gtcctggatt cggcagtctc cagagaaagg actggaatgg      720
atcggggaga tcaatcatgg aggctacgtt acttacaatc cctccctgga gagtcgagtg      780
acgatctctg tggatacatc taaaaaccag ttttctctca agctgagttc tgttacagcg      840
gctgacaccg ccgtatacta ttgtgcgcgg gactatggcc ctggcaacta cgactggtac      900
tttgacctgt gggggagagg cacgctggtg acagtctcga gcgctagcac caagggcccc      960
tccgtgttcc ccctggcccc ttgctcccgg tccacctccg agtctaccgc cgctctgggc     1020
tgcctggtga aagactactt ccccgagcct gtgaccgtga gctggaactc tggcgccctg     1080
acctccggcg tgcacacctt ccctgccgtg ctgcaatcct ccggcctgta ctccctgtcc     1140
tccgtggtga cagtgccctc ctccagcctg gcaccaagac cctacacctg taacgtggac     1200
cacaagccct ccaacaccaa ggtggacaag cgggtggaat ctaaatacgg ccctcccctgc    1260
cccccctgcc ctgcccctga atttctgggc ggaccttccg tgtttctgtt ccccccaaag    1320
cccaaggaca ccctgatgat ctcccggacc cccgaagtga cctgcgtggt ggtggacgtg    1380
tcccaggaag atccagaggt gcagttcaac tggtatgttg acggcgtgga agtgcacaac    1440
gccaagacca gcccagaga ggaacagttc aactccacct accgggtggt gtccgtgctg     1500
accgtgctgc accaggactg gctgaacggc aaagagtaca gtgcaaggt gtccaacaag    1560
ggcctgccct ccagcatcga aaagaccatc tccaaggcca agggccagcc ccgcgagccc    1620
caggtgtaca ccctgccccc tagccaggaa gagatgacca gaaccaggt gtccctgacc    1680
tgtctggtga aaggcttcta cccctccgac attgccgtgg aatgggagtc caacggccag    1740
cccgagaaca actacaagac cacccccct gtgctggact ccgacggctc cttcttcctg    1800
tactctcggc tgacagtgga taagtcccgg tggcaggaag caacgtgtt ctcctgcagc    1860
gtgatgcacg aggccctgca caaccactat acccagaagt ccctgtccct gagcctgggc    1920
aag                                                                 1923
```

<210> SEQ ID NO 60
<211> LENGTH: 648
<212> TYPE: DNA
<213> ORGANISM: artificial
<220> FEATURE:
<223> OTHER INFORMATION: fusion polypeptide light chain

<400> SEQUENCE: 60

```
gagattgtcc tgacccagtc ccccgcaaca ctgtcactgt ccccggcga gagggctact       60
ctgagttgcc gggcaagcca gtctgtgtcc agctacctgg cctggtatca gcagaagcca     120
gggcaggctc ccagactgct gatctacgac gcatctaaca gagccaccgg aattcctgcc     180
cgcttctcgg gttcaggctc cggaacagac tttaccctga caatctctag tctgagcca     240
gaagatttcg cagtctacta ttgtcagcag cgaagcaatt ggccccctgc tctgactttt     300
ggcggaggga ccaaggtgga gatcaagcgt acggtcgcgg cgccttctgt gttcattttc     360
cccccatctg atgaacagct gaaatctggc actgcttctg tggtctgtct gctgaacaac     420
ttctacccta gagaggccaa agtccagtgg aaagtggaca atgctctgca gagtgggaat     480
tcccaggaat ctgtcactga gcaggactct aaggatagca catactccct gtcctctact     540
ctgacactga gcaaggctga ttacgagaaa cacaaagtgt acgcctgtga agtcacacat     600
cagggggctgt ctagtcctgt gaccaaatcc ttcaataggg gagagtgc                 648
```

<210> SEQ ID NO 61
<211> LENGTH: 1344
<212> TYPE: DNA
<213> ORGANISM: artificial
<220> FEATURE:
<223> OTHER INFORMATION: fusion polypeptide heavy chain

<400> SEQUENCE: 61

| | | | | | |
|---|---|---|---|---|---|
| caggtccagc | tgcagcagtg | ggggctggt | ctgctgaagc | caagtgaaac | tctgtcactg | 60 |
| acctgcgctg | tgtacggcgg | atcattctcc | ggctactatt | ggtcttggat | cagacagagt | 120 |
| cccgagaaag | gcctggaatg | gatcggagag | attaaccacg | ggggttacgt | gacctataat | 180 |
| cctagcctgg | agtctagggt | gaccatttcc | gtcgacacaa | gcaagaacca | gttctctctg | 240 |
| aaactgtcca | gcgtgacagc | cgctgacact | gcagtctact | attgtgccag | ggattatggc | 300 |
| cccggaaatt | acgactggta | ttttgatctg | tggggcggg | gtaccctggt | gacagtctcg | 360 |
| agcgctagca | ccaagggccc | ctccgtgttc | cccctggccc | cttgctcccg | gtccacctcc | 420 |
| gagtctaccg | ccgctctggg | ctgcctggtg | aaagactact | tccccgagcc | tgtgaccgtg | 480 |
| agctggaact | ctggcgccct | gacctccggc | gtgcacacct | ccctgccgt | gctgcaatcc | 540 |
| tccggcctgt | actccctgtc | ctccgtggtg | acagtgccct | cctccagcct | gggcaccaag | 600 |
| acctacacct | gtaacgtgga | ccacaagccc | tccaacacca | aggtggacaa | gcgggtggaa | 660 |
| tctaaatacg | gccctccctg | ccccccctgc | cctgcccctg | aatttctggg | cggaccttcc | 720 |
| gtgtttctgt | tccccccaaa | gcccaaggac | accctgatga | tctcccggac | ccccgaagtg | 780 |
| acctgcgtgg | tggtggacgt | gtcccaggaa | gatccagagg | tgcagttcaa | ctggtatgtt | 840 |
| gacggcgtgg | aagtgcacaa | cgccaagacc | aagcccagag | aggaacagtt | caactccacc | 900 |
| taccgggtgg | tgtccgtgct | gaccgtgctg | caccaggact | ggctgaacgg | caaagagtac | 960 |
| aagtgcaagg | tgtccaacaa | gggcctgccc | tccagcatcg | aaaagaccat | ctccaaggcc | 1020 |
| aagggccagc | cccgcgagcc | ccaggtgtac | accctgcccc | ctagccagga | agagatgacc | 1080 |
| aagaaccagg | tgtccctgac | ctgtctggtg | aaaggcttct | accctccga | cattgccgtg | 1140 |
| gaatgggagt | ccaacggcca | gcccgagaac | aactacaaga | ccacccccc | tgtgctggac | 1200 |
| tccgacggct | ccttcttcct | gtactctcgg | ctgacagtgg | ataagtcccg | gtggcaggaa | 1260 |
| ggcaacgtgt | tctcctgcag | cgtgatgcac | gaggccctgc | acaaccacta | tacccagaag | 1320 |
| tccctgtccc | tgagcctggg | caag | | | | 1344 |

<210> SEQ ID NO 62
<211> LENGTH: 1227
<212> TYPE: DNA
<213> ORGANISM: artificial
<220> FEATURE:
<223> OTHER INFORMATION: fusion polypeptide light chain

<400> SEQUENCE: 62

| | | | | | |
|---|---|---|---|---|---|
| caggactcca | ctagcgatct | gatcccggct | ccccctctga | gtaaggtgcc | cctgcaacaa | 60 |
| aacttccaag | acaatcagtt | tcagggcaaa | tggtacgtgg | tcgggagagc | tggtaacgtg | 120 |
| ggactgcgag | aggacaagga | ccccccaaa | atgtgggcca | ccatctacga | gctgaaggaa | 180 |
| gacaaaagct | atgatgtgac | aaatgtcagg | ttcgcacgga | agaaatgcac | ttactcaatc | 240 |
| ggcaccttcg | tgcccggctc | ccagcctggg | gagtttacac | tggccagat | taagagcgaa | 300 |
| cctggcggaa | cagccaacct | ggtgcgggtg | gtctctacta | actataatca | gcacgctatg | 360 |

| | |
|---|---|
| gtgttcttta aagaggtcta ccagaaccga gaaatcttct ttatcatcct gtacggccgt | 420 |
| accaaggagc tgacatccga gctgaaagaa aacttcatcc gcttttctaa gagtctggga | 480 |
| ctgccagaaa atcatattgt gtttcctgtc ccaatcgacc agtgtattga tggggcggt | 540 |
| ggaggatccg ggggtggggg aagcggcgga ggaggtagcg agattgtcct tacacagtca | 600 |
| ccagccaccc tgtccttgtc acccggtgag cgcgccacac tgtcctgccg ggcatcacaa | 660 |
| agcgttagct cctacttggc atggtaccag cagaagcctg gacaggcccc aaggctgctg | 720 |
| atctatgatg ctagcaacag ggccaccggc attcccgccc gtttctctgg tagtgggagc | 780 |
| ggcactgact ttacattgac aatctcttca ttggagcccg aggactttgc tgtgtactac | 840 |
| tgtcagcagc ggagcaactg gcctcccgcc ctgaccttcg gcggggggcac aaaggtggag | 900 |
| attaagcgta cggtcgcggc gccttctgtg ttcattttcc ccccatctga tgaacagctg | 960 |
| aaatctggca ctgcttctgt ggtctgtctg ctgaacaact tctaccctag agaggccaaa | 1020 |
| gtccagtgga agtggacaa tgctctgcag agtgggaatt cccaggaatc tgtcactgag | 1080 |
| caggactcta aggatagcac atactccctg tcctctactc tgacactgag caaggctgat | 1140 |
| tacgagaaac acaaagtgta cgcctgtgaa gtcacacatc aggggctgtc tagtcctgtg | 1200 |
| accaaatcct tcaatagggg agagtgc | 1227 |

<210> SEQ ID NO 63
<211> LENGTH: 1029
<212> TYPE: DNA
<213> ORGANISM: artificial
<220> FEATURE:
<223> OTHER INFORMATION: fusion polypeptide heavy chain

<400> SEQUENCE: 63

| | |
|---|---|
| tggtattttg atctgtgggg gcggggtacc ctggtgacag tctcgagcgc tagcaccaag | 60 |
| ggcccctccg tgttcccct ggccccttgc tcccggtcca cctccgagtc taccgccgct | 120 |
| ctgggctgcc tggtgaaaga ctacttcccc gagcctgtga ccgtgagctg gaactctggc | 180 |
| gccctgacct ccggcgtgca caccttccct gccgtgctgc aatcctccgg cctgtactcc | 240 |
| ctgtcctccg tggtgacagt gccctcctcc agcctgggca ccaagaccta cacctgtaac | 300 |
| gtggaccaca agccctccaa caccaaggtg gacaagcggg tggaatctaa atacggccct | 360 |
| ccctgccccc cctgccctgc ccctgaattt ctgggcggac cttccgtgtt tctgttcccc | 420 |
| ccaaagccca aggacaccct gatgatctcc cggacccccg aagtgacctg cgtggtggtg | 480 |
| gacgtgtccc aggaagatcc agaggtgcag ttcaactggt atgttgacgg cgtggaagtg | 540 |
| cacaacgcca agaccaagcc cagagaggaa cagttcaact ccacctaccg ggtggtgtcc | 600 |
| gtgctgaccg tgctgcacca ggactggctg aacggcaaag agtacaagtg caaggtgtcc | 660 |
| aacaagggcc tgcctccag catcgaaaag accatctcca aggccaaggg ccagccccgc | 720 |
| gagccccagg tgtacaccct gccccctagc caggaagaga tgaccaagaa ccaggtgtcc | 780 |
| ctgacctgtc tggtgaaagg cttctacccc tccgacattg ccgtggaatg ggagtccaac | 840 |
| ggccagcccg agaacaacta caagaccacc cccctgtgc tggactccga cggctccttc | 900 |
| ttcctgtact ccggctgac agtggataag tccggtggc aggaaggcaa cgtgttctcc | 960 |
| tgcagcgtga tgcacgaggc cctgcacaac cactataccc agaagtccct gtccctgagc | 1020 |
| ctgggcaag | 1029 |

<210> SEQ ID NO 64
<211> LENGTH: 1224

```
<212> TYPE: DNA
<213> ORGANISM: artificial
<220> FEATURE:
<223> OTHER INFORMATION: fusion polypeptide light chain

<400> SEQUENCE: 64
gagattgtcc tgacccagtc ccccgcaaca ctgtcactgt cccccggcga gagggctact      60
ctgagttgcc gggcaagcca gtctgtgtcc agctacctgg cctggtatca gcagaagcca     120
gggcaggctc ccagactgct gatctacgac gcatctaaca gagccaccgg aattcctgcc     180
cgcttctcgg gttcaggctc cggaacagac tttaccctga caatctctag tctggagcca     240
gaagatttcg cagtctacta ttgtcagcag cgaagcaatt ggccccctgc tctgactttt     300
ggcggaggga ccaaggtgga gatcaagcgt acggtcgcgg cgccttctgt gttcattttc     360
cccccatctg atgaacagct gaaatctggc actgcttctg tggtctgtct gctgaacaac     420
ttctacccta gagaggccaa agtccagtgg aaagtggaca atgctctgca gagtgggaat     480
tcccaggaat ctgtcactga gcaggactct aaggatagca catactccct gtcctctact     540
ctgacactga gcaaggctga ttacgagaaa cacaaagtgt acgcctgtga agtcacacat     600
caggggctgt ctagtcctgt gaccaaatcc ttcaataggg gagagtgcgg cggcggagga     660
tccggggtg ggggaagcgg cggaggaggt agccaggact ccactagcga tctgatcccg     720
gctccccctc tgagtaaggt gcccctgcaa caaaacttcc aagacaatca gtttcagggc     780
aaatggtacg tggtcgggag agctggtaac gtgggactgc gagaggacaa ggaccccccc     840
aaaatgtggg ccaccatcta cgagctgaag gaagacaaaa gctatgatgt gacaaatgtc     900
aggttcgcac ggaagaaatg cacttactca atcggcacct tcgtgcccgg ctcccagcct     960
ggggagttta cactgggcca gattaagagc gaacctggcg aacagccaaa cctggtgcgg    1020
gtggtctcta ctaactataa tcagcacgct atggtgttct taaagaggt ctaccagaac    1080
cgagaaatct tctttatcat cctgtacggc cgtaccaagg agctgacatc cgagctgaaa    1140
gaaaacttca tccgcttttc taagagtctg ggactgccag aaaatcatat tgtgtttcct    1200
gtcccaatcg accagtgtat tgat                                          1224

<210> SEQ ID NO 65
<211> LENGTH: 1845
<212> TYPE: DNA
<213> ORGANISM: artificial
<220> FEATURE:
<223> OTHER INFORMATION: fusion polypeptide

<400> SEQUENCE: 65
caggactcca ctagcgatct gatcccggct ccccctctga gtaaggtgcc cctgcaacaa      60
aacttccaag acaatcagtt tcagggcaaa tggtacgtgg tcgggagagc tggtaacgtg     120
ggactgcgag aggacaagga ccccccaaa atgtgggcca ccatctacga gctgaaggaa     180
gacaaaagct atgatgtgac aaatgtcagg ttcgcacgga gaaatgcac ttactcaatc     240
ggcaccttcg tgcccggctc ccagcctggg gagtttacac tgggccagat taagagcgaa     300
cctggcggaa cagccaacct ggtgcgggtg tctctacta actataatca gcacgctatg     360
gtgttctta aagaggtcta ccagaaccga gaaatcttct ttatcatcct gtacggccgt     420
accaaggagc tgacatccga gctgaaagaa aacttcatcc gcttttctaa gagtctggga     480
ctgccagaaa atcatattgt gtttcctgtc ccaatcgacc agtgtattga tggggcggt     540
ggaggatccg ggggtggggg aagcggcgga ggaggtagcg aatcgaaata cggccctccc     600
```

| | |
|---|---|
| tgccccccct gccctgcccc tgaagctgcg ggcggacctt ccgtgtttct gttcccccca | 660 |
| aagcccaagg acaccctgat gatctcccgg acccccgaag tgacctgcgt ggtggtggac | 720 |
| gtgtcccagg aagatccaga ggtgcagttc aactggtatg ttgacggcgt ggaagtgcac | 780 |
| aacgccaaga ccaagcccag agaggaacag ttcaactcca cctaccgggt ggtgtccgtg | 840 |
| ctgaccgtgc tgcaccagga ctggctgaac ggcaaagagt acaagtgcaa ggtgtccaac | 900 |
| aagggcctgc cctccagcat cgaaaagacc atctccaagg ccagggcca gccccgcgag | 960 |
| ccccaggtgt acaccctgcc ccctagccag gaagagatga ccaagaacca ggtgtccctg | 1020 |
| acctgtctgg tgaaaggctt ctacccctcc gacattgccg tggaatggga gtccaacggc | 1080 |
| cagcccgaga caactacaa gaccaccccc cctgtgctgg actccgacgg ctccttcttc | 1140 |
| ctgtactctc ggctgacagt ggataagtcc cggtggcagg aaggcaatgt gttctcctgc | 1200 |
| agcgtgatgc acgaggccct gcacaaccac tatacccaga gtccctgtc cctgagcctg | 1260 |
| ggcaagggcg gtggaggatc cggggtggg ggaagcggcg gaggaggtag ccaggactct | 1320 |
| actagtgatc tgatcccggc accgccactg tcaaaagtcc ctctgcaaca aaactttcaa | 1380 |
| gacaatcagt ttcacggcaa atggtatgtg tcggccagg ccggaaacat taggctgcgg | 1440 |
| gaggacaagg accccatcaa aatgatggct accatctacg agctgaagga agacaaatct | 1500 |
| tatgatgtga caatggtcaa gttcgacgat aagaaatgca tgtacgacat ctggaccttc | 1560 |
| gtgcccggct cccagccggg agagttcacc ctgggcaaga tcaagtcctt ccccggccac | 1620 |
| acttccagcc tggtccgcgt ggtctcgacc aactataatc agcatgctat ggtgttcttc | 1680 |
| aagttcgtct ttcagaatag agaggagttc tacatcacac tgtatggacg caccaaggag | 1740 |
| ctgacaagcg agctgaaaga aaacttcatc aggttttcaa agtccctggg gctgcccgaa | 1800 |
| aatcatatcg tgttcccagt ccccatcgac cagtgtattg atggt | 1845 |

<210> SEQ ID NO 66
<211> LENGTH: 1830
<212> TYPE: DNA
<213> ORGANISM: artificial
<220> FEATURE:
<223> OTHER INFORMATION: fusion polypeptide

<400> SEQUENCE: 66

| | |
|---|---|
| caggactcta ctagtgatct gattccagcc cctccactga gtaaggtgcc cctgcagcag | 60 |
| aacttccagg acaatcagtt tcagggcaag tggtatgtcg tgggaagagc aggaaacgtg | 120 |
| ggactgcgtg aggacaagga ccctccaaaa atgtgggcca ctatctacga gctgaaggaa | 180 |
| gacaaatcct atgatgtgac caatgtcaga ttcgctcgca agaaatgtac atactccatc | 240 |
| ggaactttcg tgcctggaag ccagccaggg gagtttaccc tggggcagat taagtcagaa | 300 |
| ccaggcggaa ccgccaacct ggtgcgagtg gtctccacaa actataatca gcacgctatg | 360 |
| gtgttcttta agaggtcta ccagaacagg gaaatcttct ttatcatcct gtacggccgg | 420 |
| accaaggagc tgacatccga gctgaaagaa aacttcatcc gtttttcaaa gtccctggga | 480 |
| ctgcccgaaa atcatatcgt gttccccgtc ctatcgaccc agtgcattga tgggggtggc | 540 |
| ggagggtccg gtggcggagg gagccaggac agcacatcgg atctgatccc ggcaccgcca | 600 |
| ctgtcgaaag tcccactgca acaaaatttt caagacaatc agtttcacgg caagtggtac | 660 |
| gtggtcggtc aggctggcaa cattaggctg cgggaggaca aggaccccat caagatgatg | 720 |
| gcaacaatct acgagctgaa ggaggacaaa tcttatgatg tgactattgg тcaagттcgac | 780 |
| gataagaaat gтаттgтacga catctggacc ttcgtgcccg gctcccagcc tggcgagttc | 840 |

```
acactgggca agatcaagtc cttccccggc cacacttcca gcctagtcag agtggtcagc      900
accaactata atcagcatgc tatggtgttc tttaagttcg tctttcagaa tagagaggag      960
ttctacatca ccctgtatgg ccgcactaag gagctgacct ctgagctgaa agagaatttc     1020
atccggttta gtaagtcact gggcctgcct gagaatcata tcgtgttccc agtccccatt     1080
gatcagtgca ttgatggtgg cggaggggga tccggggggtg ggggaagcgg cggaggaggt    1140
agcgaatcga aatacggccc tccctgcccc ccctgccctg ccctgaagc tgcgggcgga     1200 ccttccgtgt ttctgttccc cccaaagccc aaggacaccc tgatgatctc ccggacccc      1260 gaagtgacct gcgtggtggt ggacgtgtcc caggaagatc cagaggtgca gttcaactgg    1320
tatgttgacg gcgtggaagt gcacaacgcc aagaccaagc ccagagagga acagttcaac    1380
tccacctacc gggtggtgtc cgtgctgacc gtgctgcacc aggactggct gaacggcaaa    1440
gagtacaagt gcaaggtgtc caacaagggc ctgccctcca gcatcgaaaa gaccatctcc    1500
aaggccaagg ccagccccg cgagcccag gtgtacaccc tgccccctag ccaggaagag     1560
atgaccaaga accaggtgtc cctgacctgt ctggtgaaag gcttctaccc ctccgacatt    1620
gccgtggaat gggagtccaa cggccagccc gagaacaact acaagaccac ccccctgtg     1680 ctggactccg acggctcctt cttcctgtac tctcggctga cagtggataa gtcccggtgg    1740
caggaaggca atgtgttctc ctgcagcgtg atgcacgagg ccctgcacaa ccactatacc    1800
cagaagtccc tgtccctgag cctgggcaag                                       1830
```

<210> SEQ ID NO 67
<211> LENGTH: 1098
<212> TYPE: DNA
<213> ORGANISM: artificial
<220> FEATURE:
<223> OTHER INFORMATION: fusion polypeptide

<400> SEQUENCE: 67

```
caggactcca cctcagacct gatcccagcc ccacctctga gcaaggtccc tctgcagcag      60
aacttccagg acaaccaatt ccaagggaaa tggtatgtcg tgggcgttgc cggaaatggt     120
atgctgcgtg aggataagga tccgcttaaa atgagggcga ccatttacga gttgaaagaa    180
gataaatcat atgacgtcac cagtgtggct tttcggaata agaaatgcca ttacaagatt    240
gggacctttg tgccggggag ccagccgggc gagtttactt taggccagat taaaagtggg    300
ccgggcgaga catcaaattt ggtccgcgtc gtgagcacca actacaacca gcatgccatg    360
gtgttcttca aggaggtgag gcagaaccgc gagtggtttt ttatcacact gtacgggcgc    420
acgaaagaac tgacaagcga gctgaaggaa aattttatcc gcttttccaa atctctgggc    480
ctccctgaaa accacatcgt cttccctgtc caatcgacc agtgtatcga cggcggtggt      540
ggtggttctg gtggtggtgg atcgcaggac tccacctcag acctgatccc agccccacct    600
ctgagcaagg tccctctgca gcagaacttc aggacaacc aattccatgg gaaatggtac     660
gttgtcgggc aggccggaaa tattaggctg cgtgaggata aggatccgat taaaatgatg    720
gcgaccattt acgagttgaa agaagataaa tcatatgacg tcaccatggt gaagtttgat    780
gataagaaat gcatgtacga tatttggacc tttgtgccgg ggagccagcc gggcgagttt    840 acttttaggca agattaaaag ttttccgggc catacatcat cgttggtccg cgtcgtgagc   900
accaactaca accagcatgc catggtgttc ttcaagtttg tgtttcagaa ccgcgaggag    960
ttttatatca cactgtacgg gcgcacgaaa gaactgacaa gcgagctgaa ggaaaatttt   1020
```

```
atccgctttt ccaaatctct gggcctccct gaaaaccaca tcgtcttccc tgtcccaatc    1080
gaccagtgta tcgacggc                                                  1098

<210> SEQ ID NO 68
<211> LENGTH: 1662
<212> TYPE: DNA
<213> ORGANISM: artificial
<220> FEATURE:
<223> OTHER INFORMATION: fusion polypeptide

<400> SEQUENCE: 68
caggactcca cctcagacct gatcccagcc ccacctctga gcaaggtccc tctgcagcag      60
aacttccagg acaaccaatt ccaagggaaa tggtatgtcg tgggcgttgc cggaaatggt     120
atgctgcgtg aggataagga tccgcttaaa atgagggcga ccatttacga gttgaaagaa     180
gataaatcat atgacgtcac cagtgtggct tttcggaata gaaatgccca ttacaagatt     240
gggacctttg tgccggggag ccagccgggc gagtttactt taggccagat taaaagtggt     300
ccgggcgaga catcaaattt ggtccgcgtc gtgagcacca actacaacca gcatgccatg     360
gtgttcttca aggaggtgag gcagaaccgc gagtggtttt ttatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggcggtggt     540
ggtggttctg gtggtggtgg atcgcaggac tccacctcag acctgatccc agccccacct     600
ctgagcaagg tccctctgca gcagaacttc aggacaacc aattccatgg gaaatggtac     660
gttgtcgggc aggccggaaa tattaggctg cgtgaggata aggatccgat taaaatgatg     720
gcgaccattt acgagttgaa agaagataaa tcatatgacg tcaccatggt gaagtttgat     780
gataagaaat gcatgtacga tatttggacc tttgtgccgg ggagccagcc gggcgagttt     840
actttaggca agattaaaag ttttccgggc catacatcat cgttggtccg cgtcgtgagc     900
accaactaca accagcatgc catggtgttc ttcaagtttg tgtttcagaa ccgcgaggag     960
ttttatatca cactgtacgg cgcacgaaaa gaactgacaa gcgagctgaa ggaaaatttt    1020 atccgcttt ccaaatctct gggcctccct gaaaaccaca tcgtcttccc tgtcccaatc    1080
gaccagtgta tcgacggcgg cggaggtggc tcaggaggtg gcggatccca ggactccacc    1140
tcagacctga tccagccccc acctctgagc aaggtccctc tgcagcagaa cttccaggac    1200
aaccaattcc atgggaaatg gtacgttgtc gggcaggccg gaaatattag gctgcgtgag    1260
gataaggatc cgattaaaat gatggcgacc atttacgagt tgaaagaaga taaatcatat    1320
gacgtcacca tggtgaagtt tgatgataag aaatgcatgt acgatatttg gacctttgtg    1380
ccggggagcc agccgggcga gtttacttta ggcaagatta aaagtttttcc gggccataca    1440 tcatcgttgg tccgcgtcgt gagcaccaac tacaaccagc atgccatggt gttcttcaag    1500
tttgtgtttc agaaccgcga ggagttttat atcacactgt acgggcgcac gaaagaactg    1560
acaagcgagc tgaaggaaaa ttttatccgc ttttccaaat ctctgggcct ccctgaaaac    1620
cacatcgtct tccctgtccc aatcgaccag tgtatcgacg gc                      1662

<210> SEQ ID NO 69
<211> LENGTH: 1326
<212> TYPE: DNA
<213> ORGANISM: artificial
<220> FEATURE:
<223> OTHER INFORMATION: antibody heavy chain

<400> SEQUENCE: 69
```

```
gaggtccagc tggtgcagag cggtgccgaa gtcaagaagc ctggcgagag cctgcggatt      60
tcctgcaaag gaagcggata ctcattcagc acatactgga tctcttgggt caggcagatg     120
ccaggcaagg gactggagtg gatggggaaa atctaccccg agacagtta cactaactat     180 tctccgagtt tccaaggcca ggtcactatc agcgctgata agtcaatttc caccgcctac     240
ctgcaatggt ccagcctgaa agcctccgac accgctatgt actattgcgc tcggggtac     300 ggtatctttg attattgggg ccagggaacc ctggtgacag tctcgagcgc tagcaccaag     360 ggccctccg tgtttcctct ggccccttgc tccagatcca cctccgagtc taccgccgct     420
ctgggctgcc tcgtgaagga ctacttcccc gagcctgtga ccgtgtcctg gaactctggc     480
gctctgacct ctggcgtgca ccttcctt gctgtgctgc agtctagcgg cctgtactcc     540
ctgtcctccg tcgtgaccgt gccctcctct aacttcggca cccagaccta cacctgtaac     600
gtggaccaca gccctccaa caccaaggtg gacaagaccg tggaacggaa gtgctgcgtg     660
gaatgccccc cttgtcctgc ccctcctgtg gctggcccta gcgtgttcct gttcccccca     720
aagcccaagg acaccctgat gatctcccgg accccgaag tgacctgcgt ggtggtggat     780
gtgtcccacg aggaccccga ggtgcagttc aattggtacg tggacggcgt ggaagtgcac     840
aacgccaaga ccaagcccag agaggaacag ttcaactcca ccttccgggt ggtgtccgtg     900
ctgaccgtgg tgcatcagga ctggctgaac ggcaaagagt acaagtgcaa ggtgtccaac     960
aagggcctgc ctgccccat cgaaaagacc atctctaaga ccaagggaca gccccgcgag    1020
ccccaggtgt acacactgcc tccatcacgg gaagagatga ccaagaacca ggtgtccctg    1080
acctgtctcg tgaaaggctt ctaccctcc gatatcgccg tggaatggga gtccaacggc    1140
cagcccgaga caactacaa gaccacccc cccatgctgg actccgacgg ctcattcttc    1200
ctgtactcca agctgacagt ggacaagtcc cggtggcagc agggcaacgt gttctcctgc    1260
tccgtgatgc acgaggccct gcacaaccac tacacccaga gtccctgtc cctgagcccc    1320 gggaaa                                                                1326
```

<210> SEQ ID NO 70
<211> LENGTH: 642
<212> TYPE: DNA
<213> ORGANISM: artificial
<220> FEATURE:
<223> OTHER INFORMATION: antibody light chain

<400> SEQUENCE: 70

```
tcctatgaac tgacacagcc tccttccgtg agcgtgagcc ctggacagac tgcttctatt      60
acttgtagcg gggataacat cggggatcag tacgcccact ggtatcagca gaagcccgga     120
cagagtcctg tgctggtcat ctaccaggac aaaaacaggc catcaggcat cccgagcgg     180 ttctccggaa gcaactctgg gaataccgct acactgacta tctccggaac acaggcaatg     240
gacgaagccg attactattg cgctacctat acaggtttcg gctctctggc agtgtttggc     300
ggagggacta agctgaccgt cctgggccag cctaaagcgg cgccatccgt caccctgttc     360 cctcccctcat ccgaggaact gcaggccaat aaggctacac tggtctgtct gattagcgac     420 ttctacctg gggccgtgac tgtggcttgg aaagccgatt cttctcccgt gaaagctgga     480
gtggaaacaa ccaccccctc taaacagagc aacaacaaat acgctgcctc ttcataccctg     540 tccctgaccc ctgaacagtg gaaatctcac cggtcttact catgccaggt gacacacgag     600
ggatcaactg tggagaaaac cgtggctcct accgaatgtt ca                         642
```

<210> SEQ ID NO 71
<211> LENGTH: 1905
<212> TYPE: DNA
<213> ORGANISM: artificial
<220> FEATURE:
<223> OTHER INFORMATION: fusion polypeptide heavy chain

<400> SEQUENCE: 71

| | | | | | |
|---|---|---|---|---|---|
| gaggtccagc | tggtgcagag | cggtgccgaa | gtcaagaagc | tggcgagag | cctgcggatt | 60 |
| tcctgcaaag | gaagcggata | ctcattcagc | acatactgga | tctcttgggt | caggcagatg | 120 |
| ccaggcaagg | gactggagtg | gatggggaaa | atctaccccg | gagacagtta | cactaactat | 180 |
| tctccgagtt | tccaaggcca | ggtcactatc | agcgctgata | agtcaatttc | caccgcctac | 240 |
| ctgcaatggt | ccagcctgaa | agcctccgac | accgctatgt | actattgcgc | tcggggtac | 300 |
| ggtatctttg | attattgggg | ccagggaacc | ctggtgacag | tctcgagcgc | tagcaccaag | 360 |
| ggcccctccg | tgtttcctct | ggccccttgc | tccagatcca | cctccgagtc | taccgccgct | 420 |
| ctgggctgcc | tcgtgaagga | ctacttcccc | gagcctgtga | ccgtgtcctg | gaactctggc | 480 |
| gctctgacct | tggcgtgca | caccttccct | gctgtgctgc | agtctagcgg | cctgtactcc | 540 |
| ctgtcctccg | tcgtgaccgt | gccctcctct | aacttcggca | cccagaccta | cacctgtaac | 600 |
| gtggaccaca | agccctccaa | caccaaggtg | gacaagaccg | tggaacggaa | gtgctgcgtg | 660 |
| gaatgccccc | cttgtcctgc | ccctcctgtg | gctggcccta | gcgtgttcct | gttccccca | 720 |
| aagcccaagg | acaccctgat | gatctcccgg | acccccgaag | tgacctgcgt | ggtggtggat | 780 |
| gtgtcccacg | aggaccccga | ggtgcagttc | aattggtacg | tggacggcgt | ggaagtgcac | 840 |
| aacgccaaga | ccaagcccag | agaggaacag | ttcaactcca | ccttccgggt | ggtgtccgtg | 900 |
| ctgaccgtgg | tgcatcagga | ctggctgaac | ggcaaagagt | acaagtgcaa | ggtgtccaac | 960 |
| aagggcctgc | ctgcccccat | cgaaaagacc | atctctaaga | ccaagggaca | gccccgcgag | 1020 |
| ccccaggtgt | acacactgcc | tccatcacgg | gaagagatga | ccaagaacca | ggtgtccctg | 1080 |
| acctgtctcg | tgaaaggctt | ctacccctcc | gatatcgccg | tggaatggga | gtccaacggc | 1140 |
| cagcccgaga | acaactacaa | gaccaccccc | cccatgctgg | actccgacgg | ctcattcttc | 1200 |
| ctgtactcca | agctgacagt | ggacaagtcc | cggtggcagc | agggcaacgt | gttctcctgc | 1260 |
| tccgtgatgc | acgaggccct | gcacaaccac | tacacccaga | agtccctgtc | cctgagcccc | 1320 |
| gggaaaggcg | gcggaggatc | cggggtggg | ggaagcggcg | gaggaggtag | ccaggactcc | 1380 |
| actagcgatc | tgatcccggc | tccccctctg | agtaaggtgc | ccctgcaaca | aaacttccaa | 1440 |
| gacaatcagt | ttcagggcaa | atggtacgtg | gtcgggagag | ctggtaacgt | gggactgcga | 1500 |
| gaggacaagg | acccccccaa | aatgtgggcc | accatctacg | agctgaagga | agacaaaagc | 1560 |
| tatgatgtga | caaatgtcag | gttcgcacgg | aagaaatgca | cttactcaat | cggcaccttc | 1620 |
| gtgcccggct | cccagcctgg | ggagtttaca | ctgggccaga | ttaagagcga | acctggcgga | 1680 |
| acagccaacc | tggtgcgggt | ggtctctact | aactataatc | agcacgctat | ggtgttcttt | 1740 |
| aaagaggtct | accagaaccg | agaaatcttc | tttatcatcc | tgtacggccg | taccaaggag | 1800 |
| ctgacatccg | agctgaaaga | aaacttcatc | cgcttttcta | agagtctggg | actgccagaa | 1860 |
| aatcatattg | tgtttcctgt | cccaatcgac | cagtgtattg | atggg | | 1905 |

<210> SEQ ID NO 72
<211> LENGTH: 642
<212> TYPE: DNA
<213> ORGANISM: artificial

<220> FEATURE:
<223> OTHER INFORMATION: fusion polypeptide light chain

<400> SEQUENCE: 72

```
tcctatgaac tgacacagcc tccttccgtg agcgtgagcc ctggacagac tgcttctatt      60
acttgtagcg gggataacat cggggatcag tacgcccact ggtatcagca gaagcccgga     120
cagagtcctg tgctggtcat ctaccaggac aaaaacaggc catcaggcat tcccgagcgg     180
ttctccggaa gcaactctgg gaataccgct acactgacta tctccggaac acaggcaatg     240
gacgaagccg attactattg cgctacctat acaggtttcg gctctctggc agtgtttggc     300
ggagggacta gctgaccgt cctgggccag cctaaagcgg cgccatccgt caccctgttc     360
cctccctcat ccgaggaact gcaggccaat aaggctacac tggtctgtct gattagcgac     420
ttctaccctg gggccgtgac tgtggcttgg aaagccgatt cttctcccgt gaaagctgga     480
gtggaaacaa ccacccctc taaacagagc aacaacaaat acgctgcctc ttcatacctg     540
tccctgaccc ctgaacagtg gaaatctcac cggtcttact catgccaggt gacacacgag     600
ggatcaactg tggagaaaac cgtggctcct accgaatgtt ca                        642
```

<210> SEQ ID NO 73
<211> LENGTH: 229
<212> TYPE: PRT
<213> ORGANISM: artificial
<220> FEATURE:
<223> OTHER INFORMATION: IgG4-Fc with mutations

<400> SEQUENCE: 73

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220
```

Leu Ser Leu Gly Lys
225

<210> SEQ ID NO 74
<211> LENGTH: 448
<212> TYPE: PRT
<213> ORGANISM: artificial
<220> FEATURE:
<223> OTHER INFORMATION: reference antibody

<400> SEQUENCE: 74

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

```
Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 75
<211> LENGTH: 216
<212> TYPE: PRT
<213> ORGANISM: reference antibody

<400> SEQUENCE: 75

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```